US006875757B2

(12) United States Patent
Miller et al.

(10) Patent No.: US 6,875,757 B2
(45) Date of Patent: Apr. 5, 2005

(54) LPA RECEPTOR AGONISTS AND ANTAGONISTS AND METHODS OF USE

(75) Inventors: Duane D. Miller, Germantown, TN (US); Gabor Tigyi, Memphis, TN (US); James T. Dalton, Columbus, OH (US); Vineet M. Sardar, Memphis, TN (US); Don B. Elrod, College Station, TX (US); Huiping Xu, Memphis, TN (US); Daniel L. Baker, Memphis, TN (US); Dean Wang, Memphis, TN (US); Karoly Liliom, Budapest (HU); David J. Fischer, Cordova, TN (US); Tamas Virag, Memphis, TN (US); Nora Nusser, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 09/811,838

(22) Filed: Mar. 19, 2001

(65) Prior Publication Data

US 2003/0027800 A1 Feb. 6, 2003

Related U.S. Application Data

(60) Provisional application No. 60/190,370, filed on Mar. 17, 2000.

(51) Int. Cl.[7] .......................... A61K 31/661; C07F 9/06
(52) U.S. Cl. ....................................... 514/119; 558/170
(58) Field of Search ........................... 558/170; 514/119

(56) References Cited

U.S. PATENT DOCUMENTS

| | | | |
|---|---|---|---|
| 3,639,571 A | 2/1972 | Turesky et al. | |
| 5,480,877 A | 1/1996 | Mosher, Jr. et al. | |
| 5,565,439 A | 10/1996 | Piazza et al. | |
| 5,750,141 A | 5/1998 | Roberts et al. | |
| 5,837,845 A | 11/1998 | Hosokawa et al. | |
| 5,945,522 A | 8/1999 | Cohen et al. | |

FOREIGN PATENT DOCUMENTS

| | | |
|---|---|---|
| EP | 0 394 663 A1 | 10/1990 |
| EP | 0 425 680 A1 | 5/1991 |
| GB | 861463 | 2/1961 |
| WO | WO 98/09668 | 3/1998 |
| WO | WO 98/41213 | 2/1999 |
| WO | WO 99/08514 | 2/1999 |
| WO | WO 99/47101 | 9/1999 |

OTHER PUBLICATIONS

Noort et al., Bioorganic & Medicinal Chemistry Letters (Aug. 20, 1996), 6(16), pp. 2007–2012.*
Avaeva et al., CA 73:31861, 1970.*
Cherbuliez et al., Helv. Chim. Acta, 43:863–867 (1960), Beilstein Registry No. 1909896.
Cameron et al., Phosphorus, Sulfur Silicon Relat. Elem., 83(1–4):21–38 (1993), Beilstein Registry No. 1759257.
Avaeva et al., Moscow Univ. Chem. Bull., 26(5):87 (1971), Beilstein Registry No. 2124207.
Cherbuliez et al., Helv. Chim. Acta, 39:1455–1456 (1956), Beilstein Registry No. 1782157.
Vutz et al., Liebigs Ann. Chem., 8:1259–1270 (1980), Beilstein Registry No. 4500093.
Burger et al., J. Org. Chem., 20:1383–1385 (1955), Beilstein Registry No. 3711336.
Blickenstaff et al., Steroids, 46(4,5):889–902 (1985), Beilstein Registry No. 6258294.
Bigham et al., Heterocycles, 35(2):1289–1307 (1993) Beilstein Registry No. 6366843.
Valerio et al., Aust. J. Chem., 45(4):777–784 (1992), Beilstein Registry No. 5338529.
Piantadosi et al., J. Med. Chem., 34(4):1408–1414 (1991), Beilstein Registry No. 4331312.
Hosokawa et al., Chem. Pharm. Bull., 17:202–206 (1969), Beilstein Registry No. 6293905.
Helferich et al., Justus Liebigs Ann. Chem., 655:59–69 (1962), Beilstein Registry No. 2736669.
Chavane et al., Ann. Chim., 4:372–379 (1949), Beilstein Registry No. 1761550.
Snyder et al., Biochemistry, 11(9):1616–23 (1972) (abstract).
Geleji et al., J. Polymer Sci., 58:955–75 (1962) (abstract).
Galardy, Biochemistry, 21(3):5777–81 (1982) (abstract).
Kimizuka et al., Chem. Lett., 1:29–30 (1999), Beilstein Registry No. 8250411.
Hamachi et al., J. Amer. Chem. Soc., 119(39):9096–9102 (1997), Beilstein Registry No. 7849035.
Ichinose et al., Chem. Lett., 4:257–258 (1996) Beilstein Registry No. 7608508.
Kunitake et al., J. Chem. Soc. Perkin Trans., 2(6):885–890 (1991), Beilstein Registry No. 4776258.
Baker et al., J. Pharm. Sci., 54:845–847 (1965), Beilstein Registry No. 1154148.
Jeck et al., Justus Liebigs Ann. Chem., 531:533–34 (1973), Beilstein Registry No. 624232.
Scola–Negalschneider et al., Eur. J. Biochem., 66:567, 570–574 (1976), Beilstein Registry No. 1053625.
Savarese et al., Biochemical Pharmacology, 40(11):2465–71 (1990) (abstract).
Streichter et al., Chemica Scripta, 26(1):179–83 (1986) (abstract).

(Continued)

Primary Examiner—Laura L. Stockton
(74) Attorney, Agent, or Firm—Nixon Peabody LLP

(57) ABSTRACT

The present invention relates to compounds according to formula (I) as disclosed herein as well as pharmaceutical compositions which include those compounds. Also disclosed are methods of using such compounds, which have activity as agonists or as antagonists of LPA receptors; such methods including inhibiting LPA activity on an LPA receptor, modulating LPA receptor activity, treating cancer, enhancing cell proliferation, and treating a wound.

7 Claims, 26 Drawing Sheets

OTHER PUBLICATIONS

Campbell, *Biochim. Biophys. Acta,* 232:427 (1971), Beilstein Registry No. 1159691.

Holy, *Collect. Czech. Chem. Commun.,* 40:187, 209 (1975), Beilstein Registry No. 3995566.

Jeck et al., *Justus Liebigs Ann. Chem.,* 961:962, 967 (1973), Beilstein Registry No. 4066019.

Cherbuliez et al., *Helv. Chim, Acta,* 50:979–985 (1967), Beilstein Registry No. 3100496.

Cherbuliez et al., *Helv. Chim. Acta,* 49:2608–2615 (1966), Beilstein Registry No. 2753057.

Guibe–Jampel et al., *Bull. Soc. Chim. FR.,* 1308, 1312 (1971), Beilstein Registry No. 2372181.

Gefflaut et al., *Biorg. Med. Chem.,* 4(12):2043–2054 (1996), Beilstein Registry No. 7635283.

Gruen et al., *Chem. Ber.,* 45:3373 (1912), Beilstein Registry No. 1811344.

Patterson et al., *J. Biol. Chem.,* 264(14):8004–11 (1989) (abstract).

Kharchenko et al., "Thermal Stability and Antiseize Properties of Somes Phosphorus–Containing Lubricating Oil Additives," 1974:523954 *CAPLUS* 81:123954 (1974) (abstract).

Li et al., "Site–Specific Photomodification of DNA by Porphyrin–Oligonucleotide Conjugates Synthesized via Solid Phase H–Phosphonate Approach," 1997:164802 *CAPLUS* 126:141410 (1997) (abstract).

Gibbs, "The Synthesis of Phosphoramidates from Silyphosphites and Azides," 1977:453513 *CAPLUS* 87:53513 (1977) (abstract).

Blume et al., "The Influence of Charge on Bilayer Membranes Calorimetric Investigations of Phosphatidic Acid Bilayers," 1980:53762 *CAPLUS* 92:53762 (1980) (abstract).

Wei et al., "Study on New Amphoteric Surfactants of Phosphates I. Syntheses and Properties," 1998:750143 *CAPLUS* 130:126594 (1998) (abstract).

Badalassi et al., "A Versatile Periodate–Coupled Fluorogenic Assay for Hydrolytic Enzymes," 2000:859470 *CAPLUS* 134:174618 (2000) (abstract).

Bushnev et al., "Synthesis of Rac–3–benzoyl–1–deoxyceramide–1–phosphonic Acid," 1983:405425 *CAPLUS* 99:5425 (1983) (abstract).

Cates, "Phosphorus–nitrogen Compounds 12 Phosphamidase Studies 2 N–alkylphosphoramidic Acids," 1971:471703 *CAPLUS* 75:71703 (1971) (abstract).

Gasco et al., "Timolol in Liposheres," 1992:221452 *CAPLUS* 116:221452 (1992) (abstract).

Avaeva et al., "Hydrolysis of Phosphoric Ester Serine Derivatives Containing Free Amino or Carboxylic Groups," 1972:34548 *CAPLUS* 76:34548 (1972) (abstract).

Valerio et al., "Synthesis of the Simple Peptide Model Ac–Abu (PO3H2)–NHMe," 1992:236128 *CAPLUS* 116:236128 (1992) (abstract).

Ryan et al., "Synthesis, Structure–Activity Relationships, and the Effect of Polyethylene Glycol on Inhibitors of Phosphatidylinositol–Specific Phospholipase C from *Bacillus cereus,*" 1996:618920 *CAPLUS* 126:16188 (1996) (abstract).

Swarthout et al., "Lysophosphatidic Acid: Receptors, Signaling and Survival,"*CMLS, Cell. Mol. Life Sci.* 57:1978–1985 (2000).

Levine et al., "Lysophosphatidic Acid: A Novel Growth and Survival Factor for Renal Proximal Tubular Cells," The American Physiological Society, pp 575–585 (1997).

Steiner et al., "Lysophosphatidic Acid Induction of Neuronal Apoptosis and Necrosis," *Annals New York Academy of Sciences* pp 132–141, year not available.

Ediger et al., "Dual Effects of Lysophosphatidic Acid on Human Airway Smooth Muscle Cell Proliferation and Survival," *Biochimica et Biophysica Acta* 59–67 (2001).

Fang et al., "Lysophosphatidic Acid Prevents Apoptosis in Fibroblasts Via $G_1$–Protein–Mediated Activation of Mitogen–Activated Protein Kinase," *Biochem J.* 352:135–143 (2000).

Frankel et al., "Peptide and Lipid Growth Factors Decrease cis–Diamminedichloroplatinum–Induced Cell Death in Human Ovarian Cancer Cells," *Clinical Cancer Research* 2:1307–1313 (1996).

Furui et al., "Overexpression of Edg–2/vzg–1 Induces Apoptosis and Anoikis in Ovarian Cancer Cells in a Lysophosphatidic Acid–Independent Manner," *Clinical Cancer Research* 5:4308–4318 (1999).

Goetzl et al., "Distinctive Expression and Functions of the Type 4 Endothelial Differentiation Gene–Encoded G Protein–Coupled Receptor for Lysophosphatidic Acid in Ovarian Cancer," *Cancer Research* 59:5370–5375 (1999).

Goetzl et al., "Lysophosphatidic Acid and Sphingosine 1–Phosphate Protection of T Cells from Apoptosis in Association With Suppression of Bax," The American Association of Immunologists pp 2049–2056 (1999).

Koh et al., "Lysophosphatidic Acid Is a Major Serum Noncytokine Survival Factor for Murine Macrophages Which Acts Via The Phosphatidylinositol 3–Kinase Signaling Pathway," *J. Clin. Invest.* 716–727 (1998).

Holtsberg et al., "Lysophosphatidic Acid and Apoptosis of Nerve Growth Factor–Differentiated PC12 Cells," *Journal of Neuroscience Research* 53:685–696 (1998).

Holtsberg et al., "Lysophosphatidic Acid Induces Necrosis and Apoptosis in Hippocampal Neurons," *Journal of Neurochemistry* 66–76 (1998).

\* cited by examiner

| | |
|---|---|
| 26  R = (CH$_2$)$_9$CH$_3$ | 35  R = (CH$_2$)$_9$CH$_3$ |
| 27  R = (CH$_2$)$_{13}$CH$_3$ | 36  R = (CH$_2$)$_{13}$CH$_3$ |
| 28  R = (CH$_2$)$_{17}$CH$_3$ | 37  R = (CH$_2$)$_{17}$CH$_3$ |
| 29  R = p-C$_6$H$_4$O(CH$_2$)$_{13}$CH$_3$ | 38  R = p-C$_6$H$_4$O(CH$_2$)$_{13}$CH$_3$ |
| 30  R = p-C$_6$H$_4$OCH$_3$ | 39  R = p-C$_6$H$_4$OCH$_3$ |
| 31  R = m-C$_6$H$_4$O(CH$_2$)$_{13}$CH$_3$ | 40  R = m-C$_6$H$_4$O(CH$_2$)$_{13}$CH$_3$ |
| 32  R = m-C$_6$H$_4$OCH$_3$ | 41  R = m-C$_6$H$_4$OCH$_3$ |
| 33  R = o-C$_6$H$_4$O(CH$_2$)$_{13}$CH$_3$ | 42  R = o-C$_6$H$_4$O(CH$_2$)$_{13}$CH$_3$ |
| 34  R = o-C$_6$H$_4$OCH$_3$ | 43  R = o-C$_6$H$_4$OCH$_3$ |

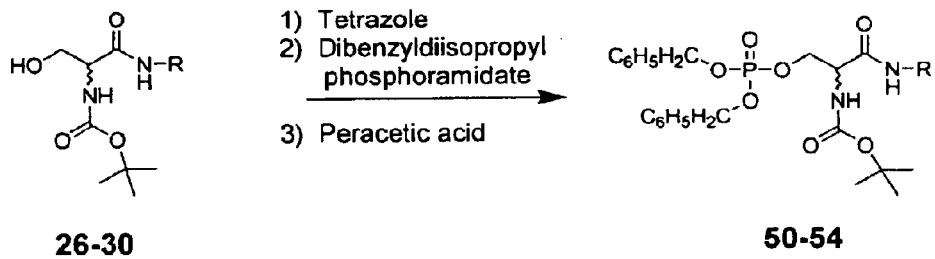
26-30
26 R = (CH₂)₉CH₃
27 R = (CH₂)₁₃CH₃
28 R = (CH₂)₁₇CH₃
29 R = p-C₆H₄O(CH₂)₁₃CH₃
30 R = p-C₆H₄OCH₃
50-54
50 R = (CH₂)₉CH₃
51 R = (CH₂)₁₃CH₃
52 R = (CH₂)₁₇CH₃
53 R = p-C₆H₄O(CH₂)₁₃CH₃
54 R = p-C₆H₄OCH₃
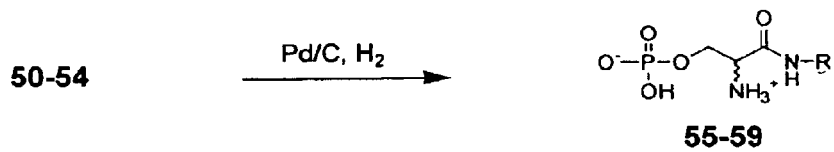
55-59
55 R = (CH₂)₉CH₃
56 R = (CH₂)₁₃CH₃
57 R = (CH₂)₁₇CH₃
58 R = p-C₆H₄O(CH₂)₁₃CH₃
59 R = p-C₆H₄OCH₃
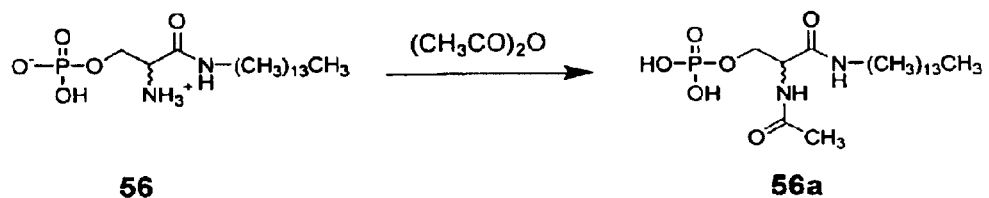
Figure 3

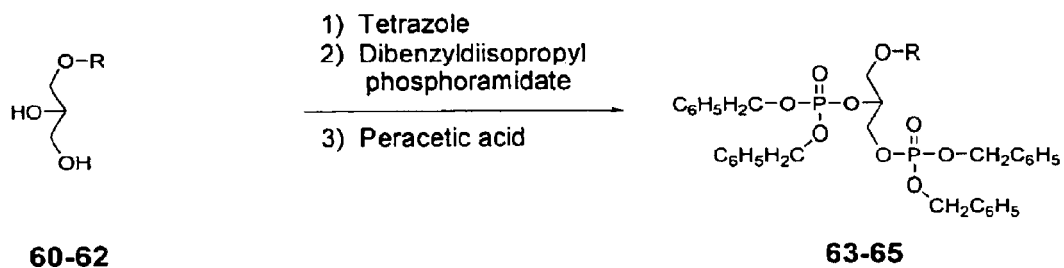
60-62
63-65
60 R = (CH₂)₁₇CH₃
61 R = (CH₂)₁₁CH₃
62 R = (CH₂)₁₅CH₃
63 R = (CH₂)₁₇CH₃
64 R = (CH₂)₁₁CH₃
65 R = (CH₂)₁₅CH₃
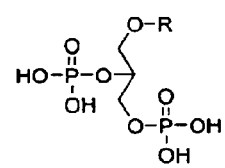
66-68
66 R = (CH₂)₁₇CH₃
67 R = (CH₂)₁₁CH₃
68 R = (CH₂)₁₅CH₃
Figure 4

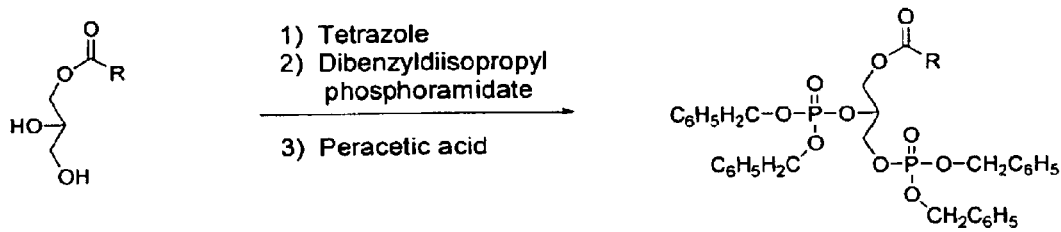
69-76
69 R = (CH₂)₁₂CH₃
70 R = (CH₂)₁₃CH₃
71 R = (CH₂)₁₄CH₃
72 R = (CH₂)₁₅CH₃
73 R = (CH₂)₁₆CH₃
74 R = (CH₂)₁₇CH₃
75 R = (CH₂)₁₈CH₃
76 R = (CH₂)₂₀CH₃
77-84
77 R = (CH₂)₁₂CH₃
78 R = (CH₂)₁₃CH₃
79 R = (CH₂)₁₄CH₃
80 R = (CH₂)₁₅CH₃
81 R = (CH₂)₁₆CH₃
82 R = (CH₂)₁₇CH₃
83 R = (CH₂)₁₈CH₃
84 R = (CH₂)₂₀CH₃
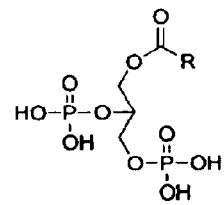
77-84 → Pd-C/H₂ →
85-92
85 R = (CH₂)₁₂CH₃
86 R = (CH₂)₁₃CH₃
87 R = (CH₂)₁₄CH₃
88 R = (CH₂)₁₅CH₃
89 R = (CH₂)₁₆CH₃
90 R = (CH₂)₁₇CH₃
91 R = (CH₂)₁₈CH₃
92 R = (CH₂)₂₀CH₃
Figure 5A

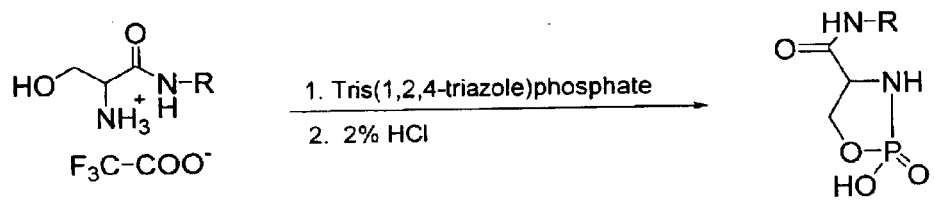
35-43
Figure 13
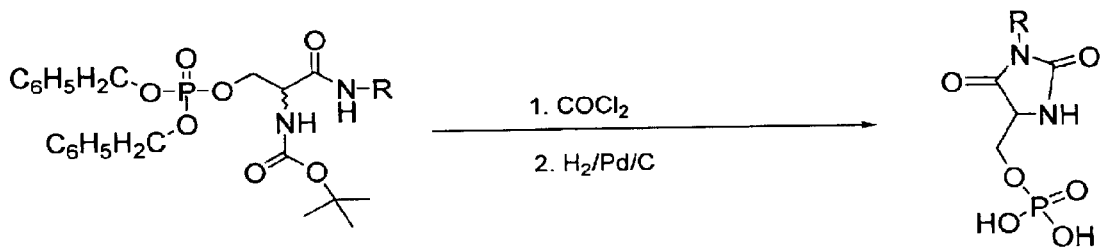
50-54
Figure 14
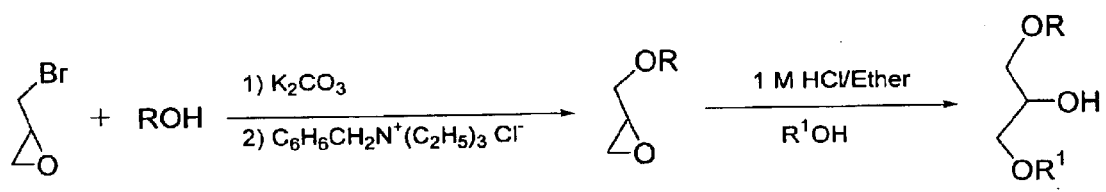
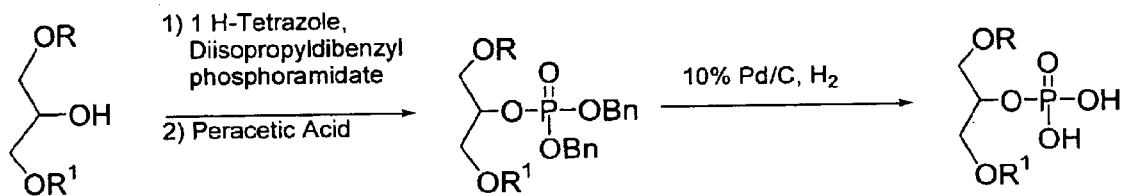
Figure 15

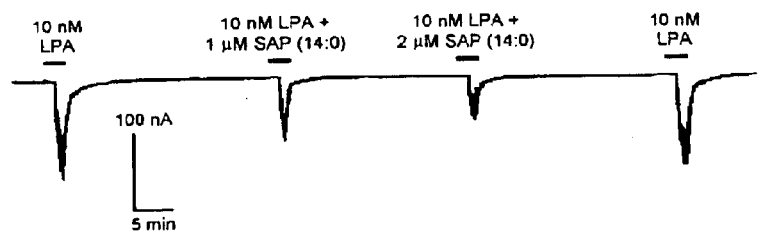
Figure 21
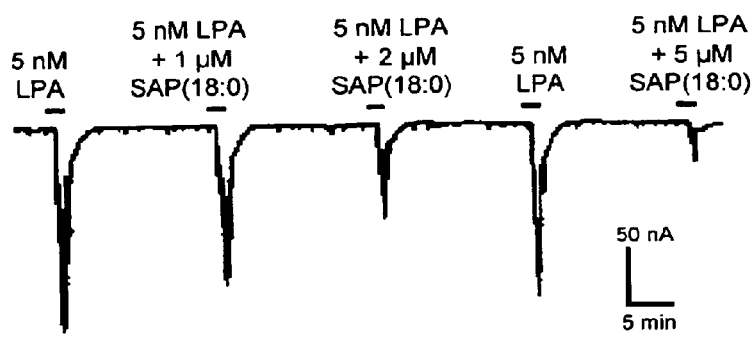
Figure 22
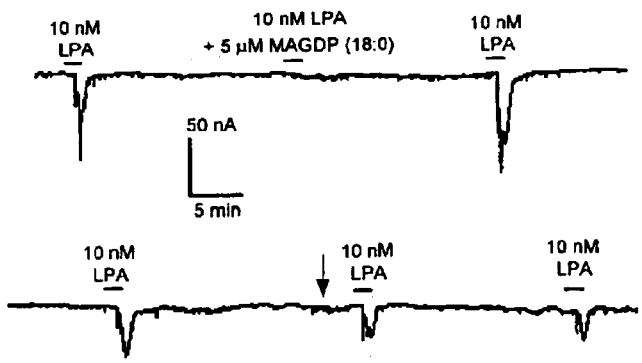
Figures 23A-B

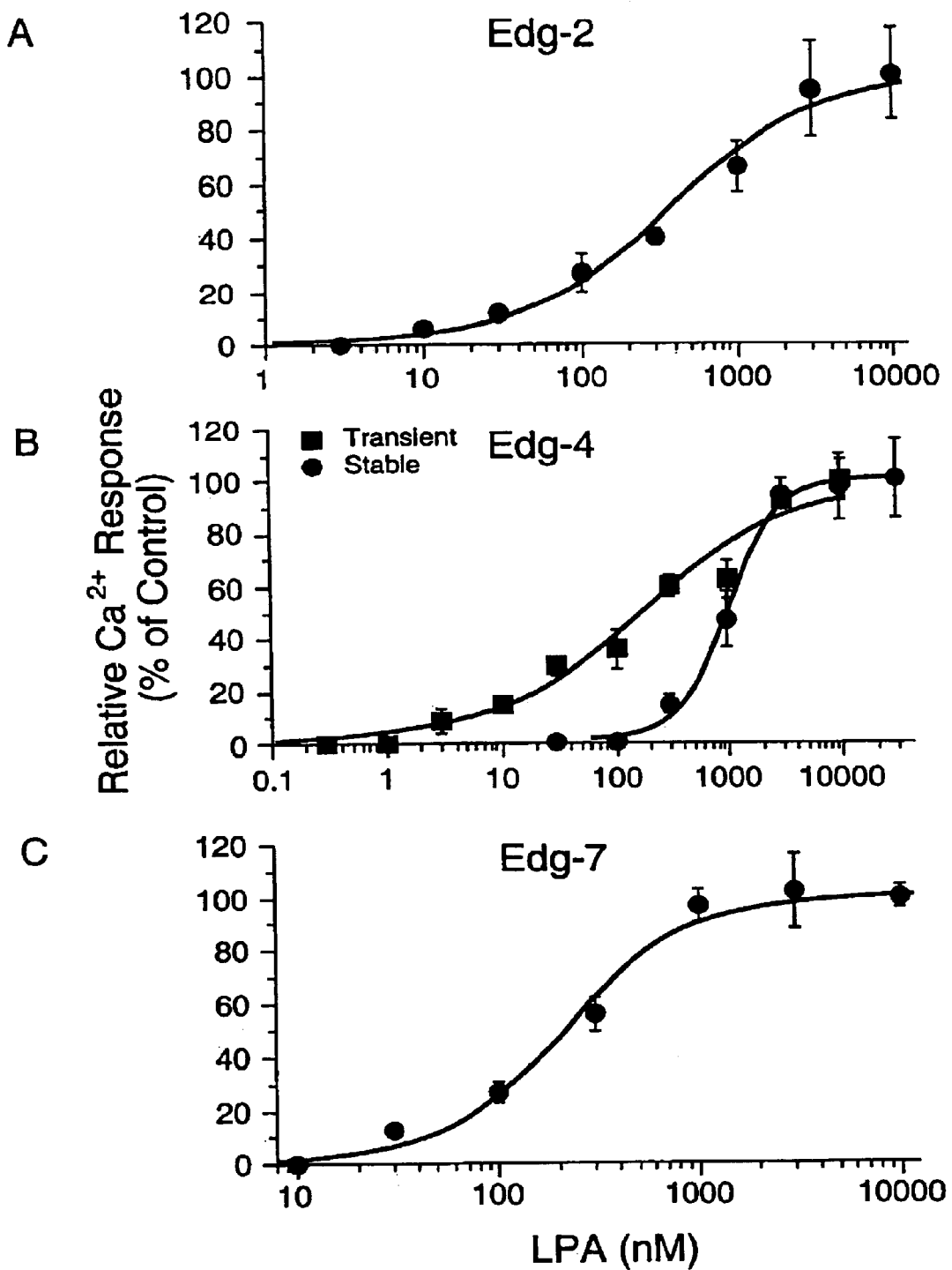
Figures 28A-C

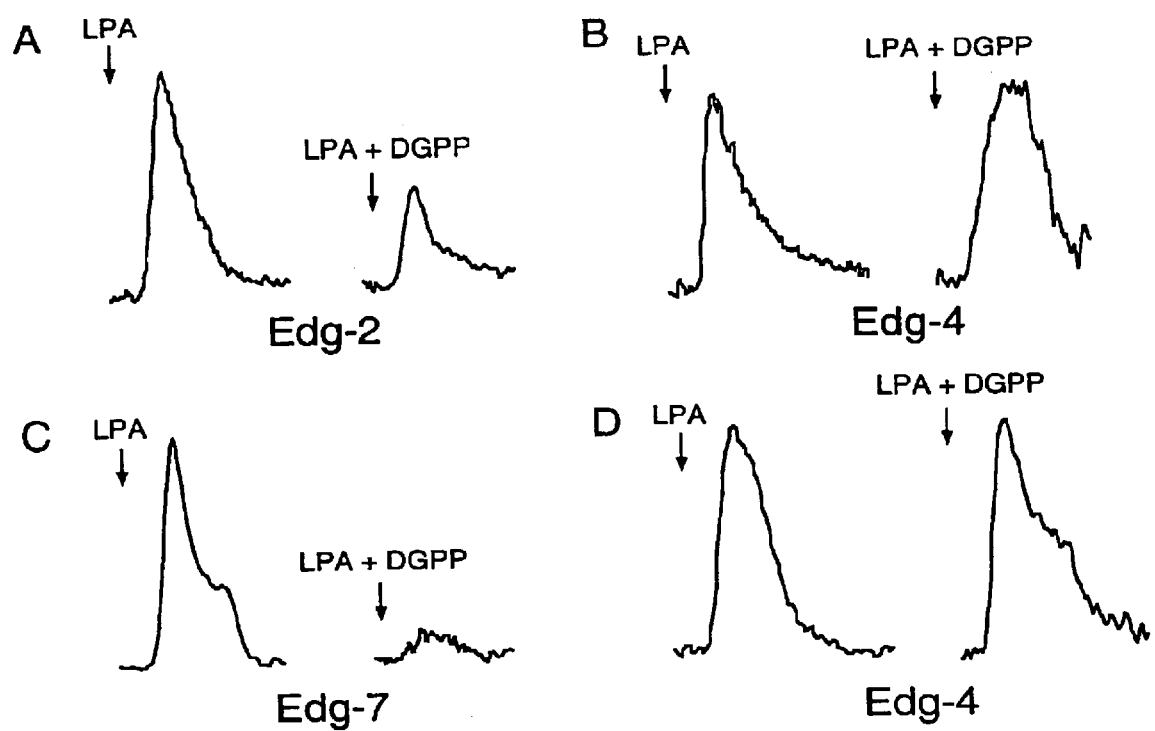
Figures 29A-D

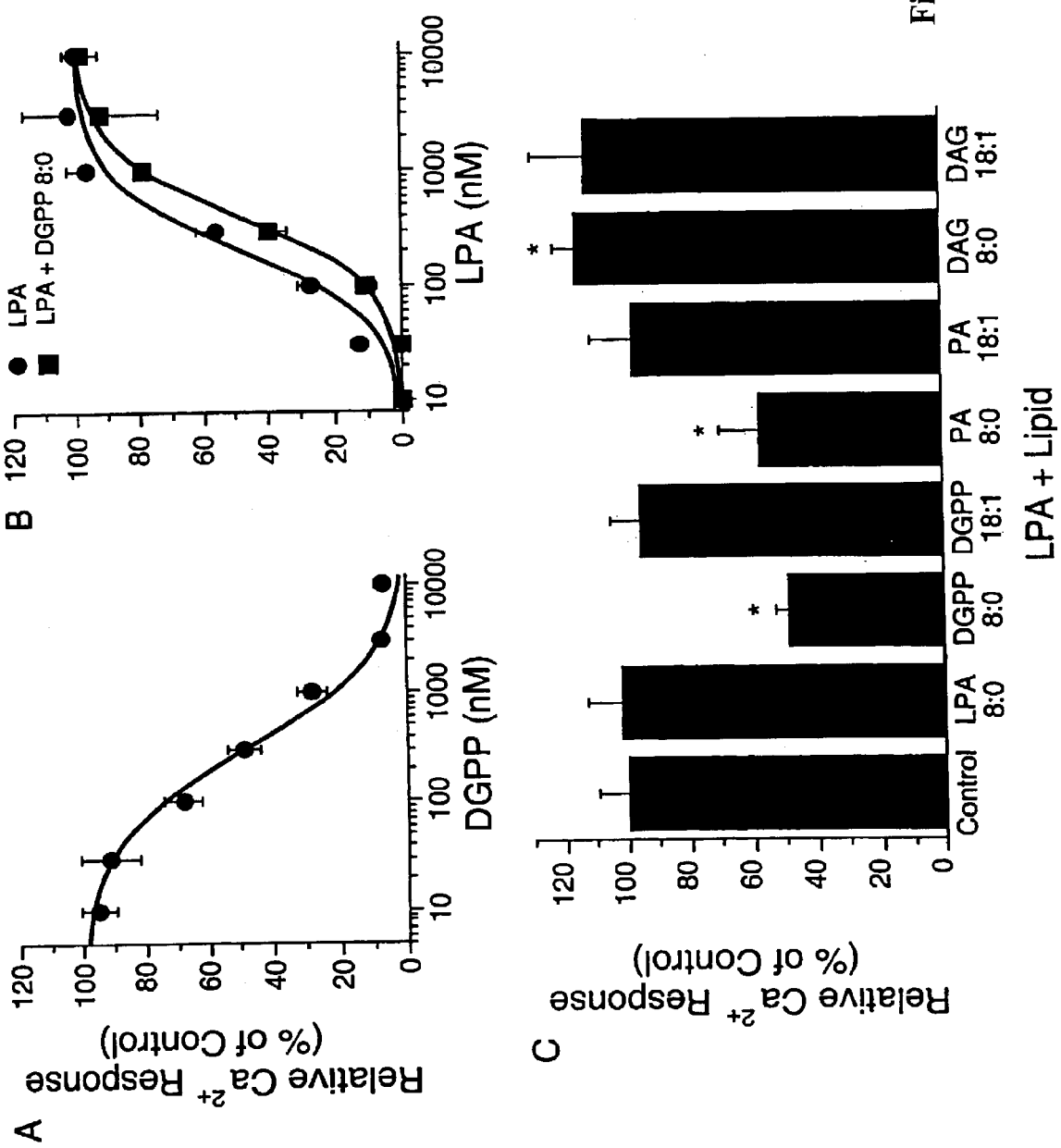
Figures 30A-C

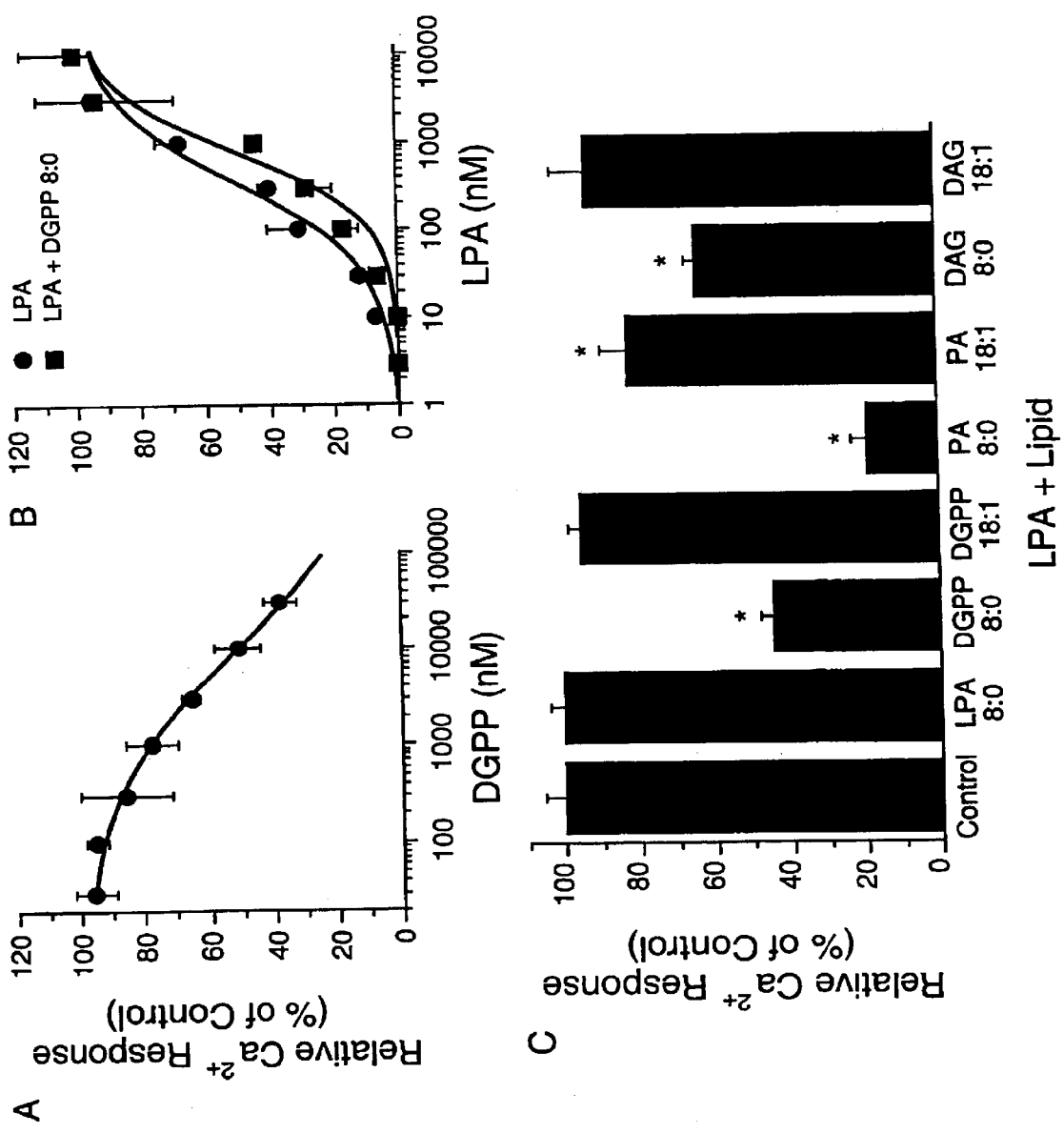
Figures 31A-C

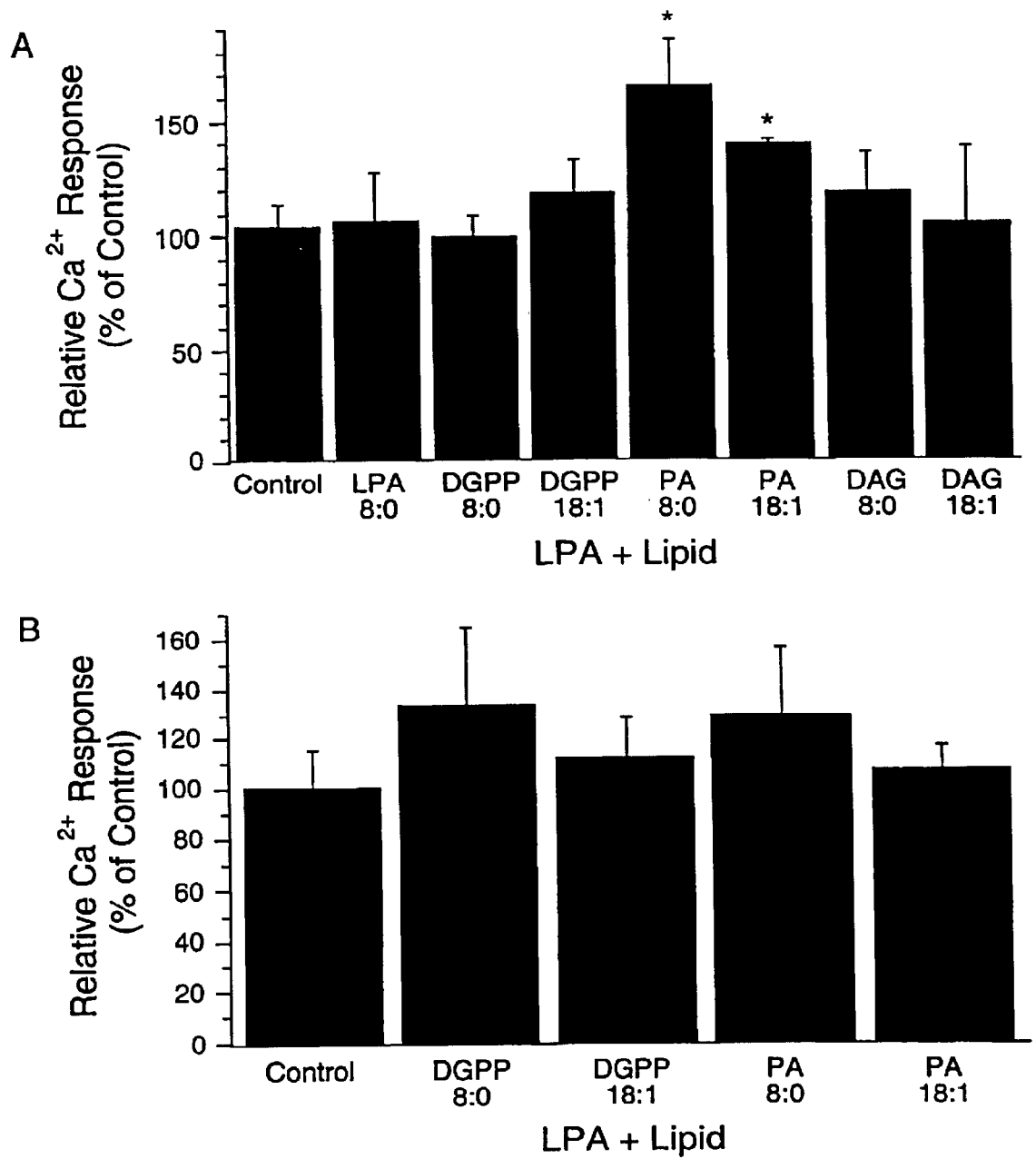
Figures 32A-B

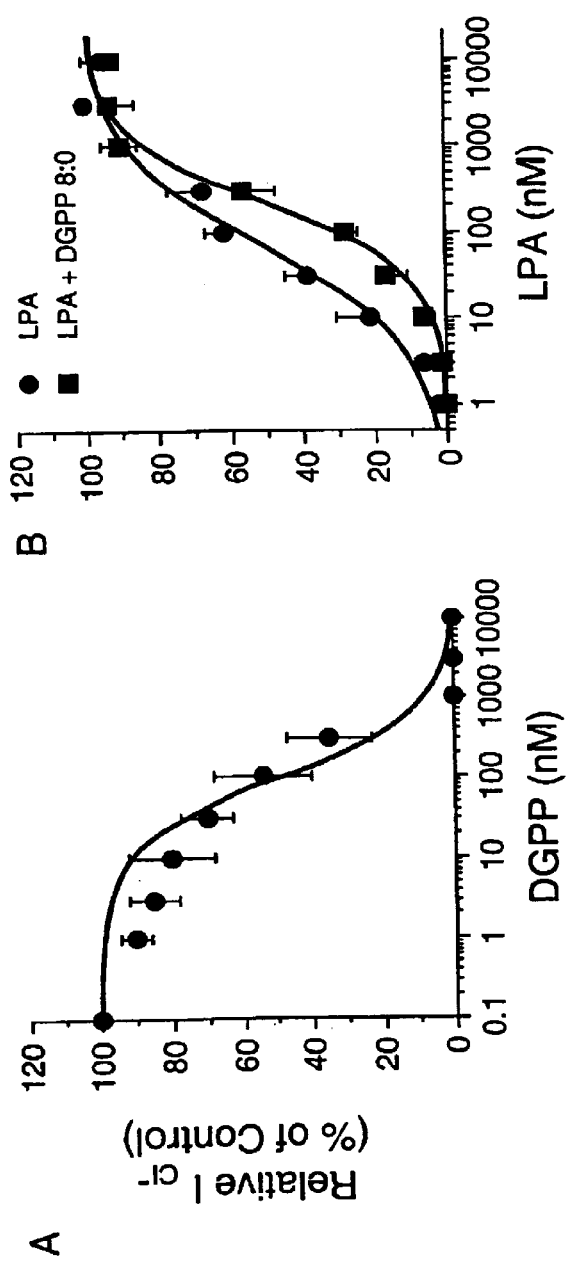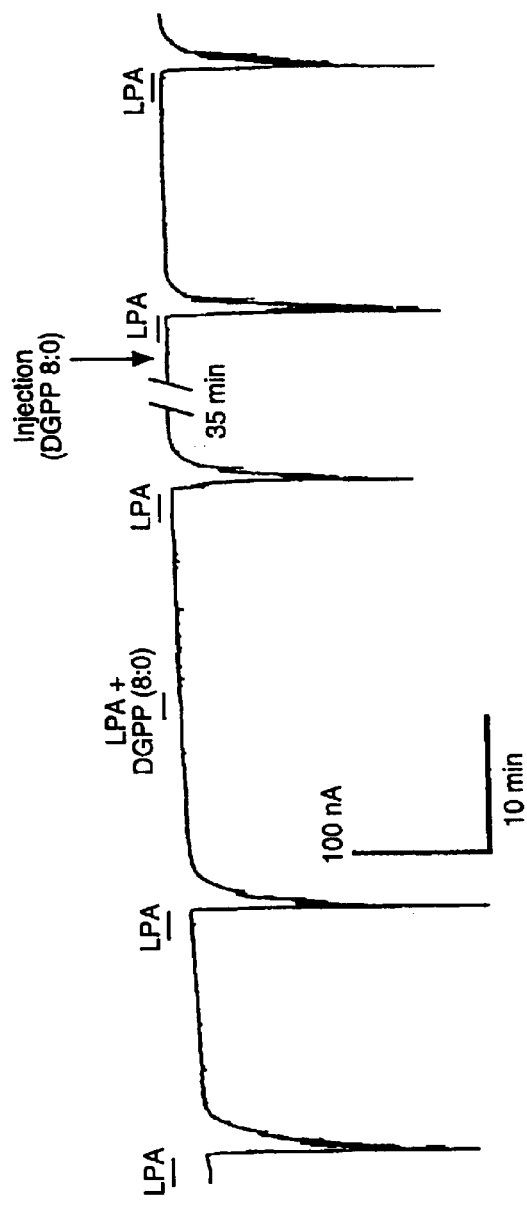
Figures 33A-C

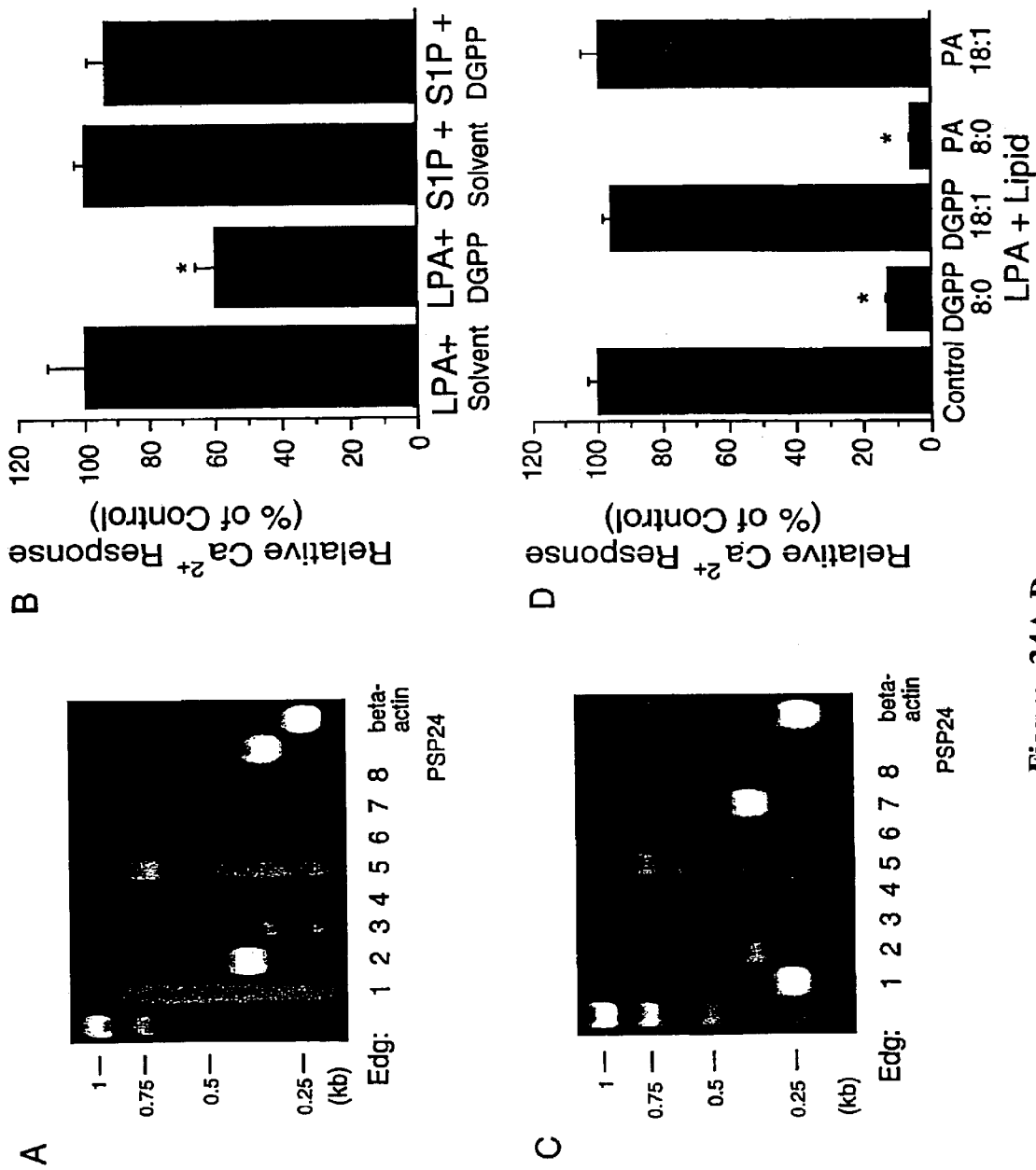
Figures 34A-D

SEQUENCE LISTING

<160> NUMBER OF SEQ ID NOS: 26

<210> SEQ ID NO 1
<211> LENGTH: 1095
<212> TYPE: DNA
<213> ORGANISM: Homo sapiens

<400> SEQUENCE: 1

```
atggctgcca tctctacttc catccctgta atttcacagc cccagttcac agccatgaat      60
```

-continued

| | |
|---|---|
| gaaccacagt gcttctacaa cgagtccatt gccttctttt ataaccgaag tggaaagcat | 120 |
| cttgccacag aatggaacac agtcagcaag ctggtgatgg gacttggaat cactgtttgt | 180 |
| atcttcatca tgttggccaa cctattggtc atggtggcaa tctatgtcaa ccgccgcttc | 240 |
| cattttccta tttattacct aatggctaat ctggctgctg cagacttctt tgctgggttg | 300 |
| gcctacttct atctcatgtt caacacagga cccaatactc ggagactgac tgttagcaca | 360 |
| tggctcctgc gtcagggcct cattgacacc agcctgacgg catctgtggc caacttactg | 420 |
| gctattgcaa tcgagaggca cattacggtt ttccgcatgc agctccacac acggatgagc | 480 |
| aaccggcggg tagtggtggt cattgtggtc atctggacta tggccatcgt tatgggtgct | 540 |
| atacccagtg tgggctggaa ctgtatctgt gatattgaaa attgttccaa catggcaccc | 600 |
| ctctacagtg actcttactt agtcttctgg gccattttca acttggtgac ctttgtggta | 660 |
| atggtggttc tctatgctca catctttggc tatgttcgcc agaggactat gagaatgtct | 720 |
| cggcatagtt ctggaccccg gcggaatcgg gataccatga tgagtcttct gaagactgtg | 780 |
| gtcattgtgc ttggggcctt tatcatctgc tggactcctg gattggtttt gttacttcta | 840 |
| gacgtgtgct gtccacagtg cgacgtgctg gcctatgaga aattcttcct tctccttgct | 900 |
| gaattcaact ctgccatgaa ccccatcatt tactcctacc gcgacaaaga aatgagcgcc | 960 |
| acctttaggc agatcctctg ctgccagcgc agtgagaacc ccaccggccc cacagaaagc | 1020 |
| tcagaccgct cggcttcctc cctcaaccac accatcttgg ctggagttca gcaatgac | 1080 |
| cactctgtgg tttag | 1095 |

<210> SEQ ID NO 2
<211> LENGTH: 364
<212> TYPE: PRT
<213> ORGANISM: Homo sapiens

<400> SEQUENCE: 2

Met Ala Ala Ile Ser Thr Ser Ile Pro Val Ile Ser Gln Pro Gln Phe
  1               5                  10                  15

Thr Ala Met Asn Glu Pro Gln Cys Phe Tyr Asn Glu Ser Ile Ala Phe
             20                  25                  30

Phe Tyr Asn Arg Ser Gly Lys His Leu Ala Thr Glu Trp Asn Thr Val
         35                  40                  45

Ser Lys Leu Val Met Gly Leu Gly Ile Thr Val Cys Ile Phe Ile Met
     50                  55                  60

Leu Ala Asn Leu Leu Val Met Val Ala Ile Tyr Val Asn Arg Arg Phe
 65                  70                  75                  80

His Phe Pro Ile Tyr Tyr Leu Met Ala Asn Leu Ala Ala Ala Asp Phe
                 85                  90                  95

Phe Ala Gly Leu Ala Tyr Phe Tyr Leu Met Phe Asn Thr Gly Pro Asn
            100                 105                 110

Thr Arg Arg Leu Thr Val Ser Thr Trp Leu Leu Arg Gln Gly Leu Ile
        115                 120                 125

Asp Thr Ser Leu Thr Ala Ser Val Ala Asn Leu Leu Ala Ile Ala Ile
    130                 135                 140

Glu Arg His Ile Thr Val Phe Arg Met Gln Leu His Thr Arg Met Ser
145                 150                 155                 160

Asn Arg Arg Val Val Val Val Ile Val Ile Trp Thr Met Ala Ile
                165                 170                 175

Val Met Gly Ala Ile Pro Ser Val Gly Trp Asn Cys Ile Cys Asp Ile

```
                180             185             190
Glu Asn Cys Ser Asn Met Ala Pro Leu Tyr Ser Asp Ser Tyr Leu Val
        195                 200                 205
Phe Trp Ala Ile Phe Asn Leu Val Thr Phe Val Met Val Val Leu
    210                 215                 220
Tyr Ala His Ile Phe Gly Tyr Val Arg Gln Arg Thr Met Arg Met Ser
225                 230                 235                 240
Arg His Ser Ser Gly Pro Arg Arg Asn Arg Asp Thr Met Met Ser Leu
                245                 250                 255
Leu Lys Thr Val Val Ile Val Leu Gly Ala Phe Ile Ile Cys Trp Thr
            260                 265                 270
Pro Gly Leu Val Leu Leu Leu Leu Asp Val Cys Cys Pro Gln Cys Asp
        275                 280                 285
Val Leu Ala Tyr Glu Lys Phe Phe Leu Leu Leu Ala Glu Phe Asn Ser
    290                 295                 300
Ala Met Asn Pro Ile Ile Tyr Ser Tyr Arg Asp Lys Glu Met Ser Ala
305                 310                 315                 320
Thr Phe Arg Gln Ile Leu Cys Cys Gln Arg Ser Glu Asn Pro Thr Gly
                325                 330                 335
Pro Thr Glu Ser Ser Asp Arg Ser Ala Ser Ser Leu Asn His Thr Ile
            340                 345                 350
Leu Ala Gly Val His Ser Asn Asp His Ser Val Val
        355                 360
```

<210> SEQ ID NO 3
<211> LENGTH: 1056
<212> TYPE: DNA
<213> ORGANISM: Homo sapiens

<400> SEQUENCE: 3

```
atggtcatca tgggccagtg ctactacaac gagaccatcg gcttcttcta taacaacagt      60
ggcaaagagc tcagctccca ctggcggccc aaggatgtgg tcgtggtggc actggggctg     120
accgtcagcg tgctggtgct gctgaccaat ctgctggtca tagcagccat cgcctccaac     180
cgccgcttcc accagcccat ctactacctg ctcggcaatc tggccgcggc tgacctcttc     240
gcgggcgtgg cctacctctt cctcatgttc cacactggtc cccgcacagc ccgactttca     300
cttgagggct ggttcctgcg cagggcttg ctggacacaa gcctcactgc gtcggtggcc     360
acactgctgg ccatcgccgt ggagcggcac cgcagtgtga tggccgtgca gctgcacagc     420
cgcctgcccc gtggccgcgt ggtcatgctc attgtgggcg tgtgggtggc tgccctgggc     480
ctggggctgc tgcctgccca ctcctggcac tgcctctgtg ccctggaccg ctgctcacgc     540
atggcacccc tgctcagccg ctcctatttg gccgtctggg ctctgtcgag cctgcttgtc     600
ttcctgctca tggtggctgt gtacacccgc attttcttct acgtgcggcg gcgagtgcag     660
cgcatggcag agcatgtcag ctgccacccc gctaccgag agaccacgct cagcctggtc     720
aagactgttg tcatcatcct gggggcgttc gtggtctgct ggacaccagg ccaggtggta     780
ctgctcctgg atggtttagg ctgtgagtcc tgcaatgtcc tggctgtaga aaagtacttc     840
ctactgttgg ccgaggccaa ctcactggtc aatgctgctg tgtactcttg ccgagatgct     900
gagatgcgcc gcaccttccg ccgccttctc tgctgcgcgt gcctccgcca gtccacccgc     960
gagtctgtcc actatacatc ctctgcccag ggaggtgcca gcactcgcat catgcttccc    1020
gagaacggcc acccactgat ggactccacc ctttag                              1056
```

<210> SEQ ID NO 4
<211> LENGTH: 351
<212> TYPE: PRT
<213> ORGANISM: Homo sapiens

<400> SEQUENCE: 4

```
Met Val Ile Met Gly Gln Cys Tyr Tyr Asn Glu Thr Ile Gly Phe Phe
  1               5                  10                  15

Tyr Asn Asn Ser Gly Lys Glu Leu Ser Ser His Trp Arg Pro Lys Asp
             20                  25                  30

Val Val Val Val Ala Leu Gly Leu Thr Val Ser Val Leu Val Leu Leu
         35                  40                  45

Thr Asn Leu Leu Val Ile Ala Ala Ile Ala Ser Asn Arg Arg Phe His
     50                  55                  60

Gln Pro Ile Tyr Tyr Leu Leu Gly Asn Leu Ala Ala Ala Asp Leu Phe
 65                  70                  75                  80

Ala Gly Val Ala Tyr Leu Phe Leu Met Phe His Thr Gly Pro Arg Thr
                 85                  90                  95

Ala Arg Leu Ser Leu Glu Gly Trp Phe Leu Arg Gln Gly Leu Leu Asp
            100                 105                 110

Thr Ser Leu Thr Ala Ser Val Ala Thr Leu Leu Ala Ile Ala Val Glu
        115                 120                 125

Arg His Arg Ser Val Met Ala Val Gln Leu His Ser Arg Leu Pro Arg
    130                 135                 140

Gly Arg Val Val Met Leu Ile Val Gly Val Trp Val Ala Ala Leu Gly
145                 150                 155                 160

Leu Gly Leu Leu Pro Ala His Ser Trp His Cys Leu Cys Ala Leu Asp
                165                 170                 175

Arg Cys Ser Arg Met Ala Pro Leu Leu Ser Arg Ser Tyr Leu Ala Val
            180                 185                 190

Trp Ala Leu Ser Ser Leu Leu Val Phe Leu Leu Met Val Ala Val Tyr
        195                 200                 205

Thr Arg Ile Phe Phe Tyr Val Arg Arg Arg Val Gln Arg Met Ala Glu
    210                 215                 220

His Val Ser Cys His Pro Arg Tyr Arg Glu Thr Thr Leu Ser Leu Val
225                 230                 235                 240

Lys Thr Val Val Ile Ile Leu Gly Ala Phe Val Val Cys Trp Thr Pro
                245                 250                 255

Gly Gln Val Val Leu Leu Leu Asp Gly Leu Gly Cys Glu Ser Cys Asn
            260                 265                 270

Val Leu Ala Val Glu Lys Tyr Phe Leu Leu Leu Ala Glu Ala Asn Ser
        275                 280                 285

Leu Val Asn Ala Ala Val Tyr Ser Cys Arg Asp Ala Glu Met Arg Arg
    290                 295                 300

Thr Phe Arg Arg Leu Leu Cys Cys Ala Cys Leu Arg Gln Ser Thr Arg
305                 310                 315                 320

Glu Ser Val His Tyr Thr Ser Ser Ala Gln Gly Gly Ala Ser Thr Arg
                325                 330                 335

Ile Met Leu Pro Glu Asn Gly His Pro Leu Met Asp Ser Thr Leu
            340                 345                 350
```

<210> SEQ ID NO 5
<211> LENGTH: 1062
<212> TYPE: DNA
<213> ORGANISM: Homo sapiens

<400> SEQUENCE: 5

```
atgaatgagt gtcactatga caagcacatg gactttttt ataataggag caacactgat      60
actgtcgatg actggacagg aacaaagctt gtgattgttt tgtgtgttgg gacgttttc     120
tgcctgttta ttttttttc taattctctg gtcatcgcgg cagtgatcaa aacagaaaa     180
tttcatttcc ccttctacta cctgttggct aatttagctg ctgccgattt cttcgctgga    240
attgcctatg tattcctgat gtttaacaca ggcccagttt caaaaacttt gactgtcaac    300
cgctggtttc tccgtcaggg gcttctggac agtagcttga ctgcttccct caccaacttg    360
ctggttatcg ccgtggagag gcacatgtca atcatgagga tgcgggtcca tagcaacctg    420
accaaaaaga gggtgacact gctcattttg cttgtctggg ccatcgccat ttttatgggg    480
gcggtcccca cactgggctg gaattgcctc tgcaacatct ctgcctgctc ttccctggcc    540
cccatttaca gcaggagtta ccttgttttc tggacagtgt ccaacctcat ggccttcctc    600
atcatggttg tggtgtacct gcggatctac gtgtacgtca agaggaaaac caacgtcttg    660
tctccgcata caagtgggtc catcagccgc cggaggacac ccatgaagct aatgaagacg    720
gtgatgactg tcttagggc gtttgtggta tgctggaccc cgggcctggt ggttctgctc    780
ctcgacggcc tgaactgcag cagtgtggc gtgcagcatg tgaaaaggtg gttcctgctg    840
ctggcgctgc tcaactccgt cgtgaacccc atcatctact cctacaagga cgaggacatg    900
tatggcacca tgaagaagat gatctgctgc ttctctcagg agaacccaga gaggcgtccc    960
tctcgcatcc cctccacagt cctcagcagg agtgacacag gcagccagta catagaggat   1020
agtattagcc aaggtgcagt ctgcaataaa agcacttcct aa                       1062
```

<210> SEQ ID NO 6
<211> LENGTH: 353
<212> TYPE: PRT
<213> ORGANISM: Homo sapiens

<400> SEQUENCE: 6

```
Met Asn Glu Cys His Tyr Asp Lys His Met Asp Phe Phe Tyr Asn Arg
  1               5                  10                  15

Ser Asn Thr Asp Thr Val Asp Asp Trp Thr Gly Thr Lys Leu Val Ile
             20                  25                  30

Val Leu Cys Val Gly Thr Phe Phe Cys Leu Phe Ile Phe Phe Ser Asn
         35                  40                  45

Ser Leu Val Ile Ala Ala Val Ile Lys Asn Arg Lys Phe His Phe Pro
     50                  55                  60

Phe Tyr Tyr Leu Leu Ala Asn Leu Ala Ala Asp Phe Phe Ala Gly
 65                  70                  75                  80

Ile Ala Tyr Val Phe Leu Met Phe Asn Thr Gly Pro Val Ser Lys Thr
                 85                  90                  95

Leu Thr Val Asn Arg Trp Phe Leu Arg Gln Gly Leu Leu Asp Ser Ser
            100                 105                 110

Leu Thr Ala Ser Leu Thr Asn Leu Leu Val Ile Ala Val Glu Arg His
        115                 120                 125

Met Ser Ile Met Arg Met Arg Val His Ser Asn Leu Thr Lys Lys Arg
    130                 135                 140

Val Thr Leu Leu Ile Leu Leu Val Trp Ala Ile Ala Ile Phe Met Gly
145                 150                 155                 160

Ala Val Pro Thr Leu Gly Trp Asn Cys Leu Cys Asn Ile Ser Ala Cys
                165                 170                 175
```

Ser Ser Leu Ala Pro Ile Tyr Ser Arg Ser Tyr Leu Val Phe Trp Thr
            180                 185                 190

Val Ser Asn Leu Met Ala Phe Leu Ile Met Val Val Tyr Leu Arg
            195                 200                 205

Ile Tyr Val Tyr Val Lys Arg Lys Thr Asn Val Leu Ser Pro His Thr
            210                 215                 220

Ser Gly Ser Ile Ser Arg Arg Thr Pro Met Lys Leu Met Lys Thr
225             230                 235                 240

Val Met Thr Val Leu Gly Ala Phe Val Val Cys Trp Thr Pro Gly Leu
                245                 250                 255

Val Val Leu Leu Leu Asp Gly Leu Asn Cys Arg Gln Cys Gly Val Gln
            260                 265                 270

His Val Lys Arg Trp Phe Leu Leu Leu Ala Leu Leu Asn Ser Val Val
            275                 280                 285

Asn Pro Ile Ile Tyr Ser Tyr Lys Asp Glu Asp Met Tyr Gly Thr Met
            290                 295                 300

Lys Lys Met Ile Cys Cys Phe Ser Gln Glu Asn Pro Glu Arg Arg Pro
305             310                 315                 320

Ser Arg Ile Pro Ser Thr Val Leu Ser Arg Ser Asp Thr Gly Ser Gln
                325                 330                 335

Tyr Ile Glu Asp Ser Ile Ser Gln Gly Ala Val Cys Asn Lys Ser Thr
            340                 345                 350

Ser

<210> SEQ ID NO 7
<211> LENGTH: 1260
<212> TYPE: DNA
<213> ORGANISM: Homo sapiens

<400> SEQUENCE: 7

```
atggtcttct cggcagtgtt gactgcgttc cataccggga catccaacac aacatttgtc      60
gtgtatgaaa acacctacat gaatattaca ctccctccac cattccagca tcctgacctc     120
agtccattgc ttagatatag ttttgaaacc atggctccca ctggtttgag ttccttgacc     180
gtgaatagta cagctgtgcc cacaacacca gcagcattta agagcctaaa cttgcctctt     240
cagatcaccc tttctgctat aatgatattc attctgtttg tgtcttttct tgggaacttg     300
gttgtttgcc tcatggttta ccaaaaagct gccatgaggt ctgcaattaa catcctcctt     360
gccagcctag cttttgcaga catgttgctt gcagtgctga acatgccctt tgccctggta     420
actattctta ctacccgatg gattttgggg aaattcttct gtagggtatc tgctatgttt     480
ttctggttat ttgtgataga aggagtagcc atcctgctca tcattagcat agataggttc     540
cttattatag tccagaggca ggataagcta aacccatata gagctaaggt tctgattgca     600
gtttcttggg caacttcctt ttgtgtagct tttccttag ccgtaggaaa ccccgacctg     660
cagataccct cccgagctcc ccagtgtgtg tttgggtaca caaccaatcc aggctaccag     720
gcttatgtga ttttgatttc tctcatttct ttcttcatac ccttcctggt aatactgtac     780
tcatttatgg gcatactcaa cacccttcgg cacaatgcct tgaggatcca tagctaccct     840
gaaggtatat gcctcagcca ggccagcaaa ctggtctca tgagtctgca gagacctttc     900
cagatgagca ttgacatggg cttaaaaca cgtgccttca ccactatttt gattctcttt     960
gctgtcttca ttgtctgctg ggccccattc accacttaca gccttgtggc aacattcagt    1020
aagcactttt actatcagca caacttttttt gagattagca cctggctact gtggctctgc    1080
```

-continued

```
tacctcaagt ctgcattgaa tccgctgatc tactactgga ggattaagaa attccatgat    1140
gcttgcctgg acatgatgcc taagtccttc aagttttttgc cgcagctccc tggtcacaca    1200
aagcgacgga tacgtcctag tgctgtctat gtgtgtgggg aacatcggac ggtggtgtga    1260
```

<210> SEQ ID NO 8
<211> LENGTH: 419
<212> TYPE: PRT
<213> ORGANISM: Homo sapiens

<400> SEQUENCE: 8

```
Met Val Phe Ser Ala Val Leu Thr Ala Phe His Gly Thr Ser Asn
 1               5                  10                  15

Thr Thr Phe Val Val Tyr Glu Asn Thr Tyr Met Asn Ile Thr Leu Pro
            20                  25                  30

Pro Pro Phe Gln His Pro Asp Leu Ser Pro Leu Arg Tyr Ser Phe
        35                  40                  45

Glu Thr Met Ala Pro Thr Gly Leu Ser Ser Leu Thr Val Asn Ser Thr
    50                  55                  60

Ala Val Pro Thr Thr Pro Ala Ala Phe Lys Ser Leu Asn Leu Pro Leu
65                  70                  75                  80

Gln Ile Thr Leu Ser Ala Ile Met Ile Phe Ile Leu Phe Val Ser Phe
                85                  90                  95

Leu Gly Asn Leu Val Val Cys Leu Met Val Tyr Gln Lys Ala Ala Met
            100                 105                 110

Arg Ser Ala Ile Asn Ile Leu Leu Ala Ser Leu Ala Phe Ala Asp Met
        115                 120                 125

Leu Leu Ala Val Leu Asn Met Pro Phe Ala Leu Val Thr Ile Leu Thr
    130                 135                 140

Thr Arg Trp Ile Phe Gly Lys Phe Phe Cys Arg Val Ser Ala Met Phe
145                 150                 155                 160

Phe Trp Leu Phe Val Ile Glu Gly Val Ala Ile Leu Leu Ile Ile Ser
                165                 170                 175

Ile Asp Arg Phe Leu Ile Ile Val Gln Arg Gln Asp Lys Leu Asn Pro
            180                 185                 190

Tyr Arg Ala Lys Val Leu Ile Ala Val Ser Trp Ala Thr Ser Phe Cys
        195                 200                 205

Val Ala Phe Pro Leu Ala Val Gly Asn Pro Asp Leu Gln Ile Pro Ser
    210                 215                 220

Arg Ala Pro Gln Cys Val Phe Gly Tyr Thr Thr Asn Pro Gly Tyr Gln
225                 230                 235                 240

Ala Tyr Val Ile Leu Ile Ser Leu Ile Ser Phe Phe Ile Pro Phe Leu
                245                 250                 255

Val Ile Leu Tyr Ser Phe Met Gly Ile Leu Asn Thr Leu Arg His Asn
            260                 265                 270

Ala Leu Arg Ile His Ser Tyr Pro Glu Gly Ile Cys Leu Ser Gln Ala
        275                 280                 285

Ser Lys Leu Gly Leu Met Ser Leu Gln Arg Pro Phe Gln Met Ser Ile
    290                 295                 300

Asp Met Gly Phe Lys Thr Arg Ala Phe Thr Thr Ile Leu Ile Leu Phe
305                 310                 315                 320

Ala Val Phe Ile Val Cys Trp Ala Pro Phe Thr Thr Tyr Ser Leu Val
                325                 330                 335

Ala Thr Phe Ser Lys His Phe Tyr Tyr Gln His Asn Phe Phe Glu Ile
```

```
                   340              345              350
Ser Thr Trp Leu Leu Trp Leu Cys Tyr Leu Lys Ser Ala Leu Asn Pro
         355              360              365

Leu Ile Tyr Tyr Trp Arg Ile Lys Lys Phe His Asp Ala Cys Leu Asp
     370              375              380

Met Met Pro Lys Ser Phe Lys Phe Leu Pro Gln Leu Pro Gly His Thr
385              390              395              400

Lys Arg Arg Ile Arg Pro Ser Ala Val Tyr Val Cys Gly Glu His Arg
             405              410              415

Thr Val Val

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: primer,
      forward EDG-1

<400> SEQUENCE: 9
tcatcgtccg gcattacaac ta                                            22

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer,
      reverse EDG-1

<400> SEQUENCE: 10
gagtgagctt gtaggtggtg                                               20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: primer,
      forward EDG-2

<400> SEQUENCE: 11
agatctgacc agccgactca c                                             21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: primer,
      reverse EDG-2

<400> SEQUENCE: 12
gttggccatc aagtaataaa ta                                            22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: primer,
      forward EDG-3

<400> SEQUENCE: 13
```
cttggtcatc tgcagcttca tc                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: primer,
      reverse EDG-3

<400> SEQUENCE: 14
tgctgatgca gaaggcaatg ta                                              22

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: primer,
      forward EDG-4

<400> SEQUENCE: 15
ctgctcagcc gctcctattt g                                               21

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: primer,
      reverse EDG-4

<400> SEQUENCE: 16
aggagcaccc acaagtcatc ag                                              22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: primer,
      forward EDG-5

<400> SEQUENCE: 17
atgggcagct tgtactcgga g                                               21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: primer,
      reverse EDG-5

<400> SEQUENCE: 18
cagccagcag acgataaaga c                                               21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: primer,
      forward EDG-6

<400> SEQUENCE: 19
tgaacatcac gctgagtgac ct                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: primer, reverse EDG-6

<400> SEQUENCE: 20
gatcatcagc accgtcttca gc                                        22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: primer, forward EDG-7

<400> SEQUENCE: 21
agcaacactg atactgtcga tg                                        22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: primer, reverse EDG-7

<400> SEQUENCE: 22
gcatcctcat gattgacatg tg                                        22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: primer, forward EDG-8

<400> SEQUENCE: 23
atctgtgcgc tctatgcaag ga                                        22

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: primer, reverse EDG-8

<400> SEQUENCE: 24
ggtgtagatg ataggattca gca                                       23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: primer, forward PSP24

<400> SEQUENCE: 25
ctgcatcatc gtgtaccaga g                                         21

```
<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence:  primer,
      reverse PSP24

<400> SEQUENCE: 26
acgaactcta tgcaggcctc gc                                              22
```

LPA RECEPTOR AGONISTS AND ANTAGONISTS AND METHODS OF USE

This application claims benefit of U.S. Provisional Patent Application Ser. No. 60/190,370 filed Mar. 17, 2000, which is hereby incorporated by reference in its entirety.

This invention was funded, in part, by the National Institutes of Health Grant Nos. HL07641-12 and GM43880 and National Science Foundation Grant No. IBN-9728147. The U.S. government may have certain rights in this invention.

FIELD OF THE INVENTION

This invention relates to lysophosphatidic acid ("LPA") derivatives which have activity as either agonists or antagonists on LPA receptors and various therapeutic uses thereof including, but not limited to, prostate cancer therapy, ovarian cancer therapy, and wound healing.

BACKGROUND OF THE INVENTION

All non-transformed cells require growth factors for their survival and proliferation. In addition to polypeptide growth factors, an emerging class of lipids with growth factor-like properties has been discovered, collectively known as phospholipid growth factors (PLGFs). In spite of their similar pharmacologic properties in inducing the proliferation of most quiescent cells (Jalink et al., 1994a; Tokumura, 1995; Moolenaar et al., 1997). PLGFs can be sub-divided structurally into two broad categories. The first category contains the glycerophospholipid mediators (GPMs), which possess a glycerol backbone. Exemplary GPMs include LPA, phosphatidic acid (PA), cyclic phosphatidic acid (cyclic-PA), alkenyl glycerol phosphate (alkenyl-GP), and lysophosphatidyl serine (LPS). The second category contains the sphingolipid mediators (SPMs), which possess a sphingoid base motif. Exemplary SPMs include sphingosine-1-phosphate (SPP), dihydrosphingosine-1-phosphate, sphingosylphosphorylcholine (SPC), and sphingosine (SPH).

LPA (Tigyi et al., 1991; Tigyi and Miledi, 1992), PA (Myher et al., 1989), alkenyl-GP (Liliom et al., 1998), cyclic-PA (Kobayashi et al., 1999), SPP (Yatomi et al., 1995), and SPC (Tigyi et al., 2000) have been detected in serum. These lipid mediators have been identified and characterized. There are still, yet unknown, PLGFs present in the serum and plasma that exhibit growth factor-like properties (Tigyi and Miledi, 1992). LPA, with its ≈20 μM concentration, is the most abundant PLGF present in the serum (Tigyi and Miledi, 1992; Jalink et al., 1993).

In eukaryotic cells, LPA is a key intermediate in the early stages of phospholipid biosynthesis, which takes place predominantly in the membrane of endoplasmic reticulum (ER) (Bosch, 1974; Bishop and Bell, 1988). In the ER, LPA is derived from the action of Acyl-CoA on glycerol-3-phosphate, which is further acylated to yield PA. Because the rate of acylation of LPA to PA is very high, very little LPA accumulates at the site of biosynthesis (Bosch, 1974). Since LPA is restricted to the ER, its role as a metabolic intermediate is most probably unrelated to its role as a signaling molecule.

LPA is a constituent of serum and its levels are in the low micromolar (μM) range (Eicholtz et al., 1993). This level is expected because LPA is released by activated platelets during the coagulation process. Unlike serum, it is not detectable in fresh blood or plasma (Tigyi and Miledi, 1992; Eicholtz et al., 1993). LPA that is present in the serum is bound to albumin, and is responsible for a majority of the heat-stable, and non-dialysable biological activity of the whole serum (Moolenaar, 1994). The active serum component that is responsible for eliciting an inward chloride current in *Xenopus* oocyte was indentified to be LPA (18:0) (Tigyi and Miledi, 1992). The bulk of the albumin-bound LPA(18:0) is produced during the coagulation process, rather than by the action of lysophospholipase D (PLD) on lyso-PC. The latter pathway is responsible for the presence of LPA in 'aged' plasma that has been de-coagulated by the action of heparin or citrate plus dextrose (Tokumura et al., 1986). Another point to note is that LPA is not present in plasma that has been treated with EDTA. This fact implies that plasma lysophospholipase may be $Ca^{2+}$-dependent (Tokumura et al., 1986).

The role of albumin is to protect LPA from the actions of phospholipases present in the serum (Tigyi and Miledi, 1992). Tigyi and Miledi suggested that albumin not only acts as a carrier of LPA in the blood stream, but also increases its physiological half-life. There are yet unidentified lipid mediators present in serum albumin that mimic the actions of LPA in eliciting chloride current in *Xenopus* oocyte.

LPA-responsive cell types extend from slime mold amoebae and *Xenopus* oocyte to mammalian somatic cells. Thus, it seems likely that the source of LPA and its release may not be restricted only to activated platelets. Recent experiments showed that, on stimulation by peptide growth factors, mammalian fibroblasts rapidly produce LPA, which is followed by its release into the extracellular medium (Fukami and Takenawa, 1992).

There is evidence that relatively high amounts of bioactive LPA of unknown cellular origin are present in the ascitic fluid of ovarian cancer patients (Xu et al., 1995a), and that the ascitic fluid from such patients is known to possess potent mitogenic activity for ovarian carcinoma cells (Mills et al., 1988; Mills et al., 1990). It remains to be established whether it is secreted by tumor cells into the extracellular fluid, secreted by leukocytes, or produced from more complex lipids via the actions of various phospholipases.

GPMs and SPMs elicit a wide variety of cellular responses that span the phylogenetic tree (Jalink et al., 1993a). LPA induces transient $Ca^{2+}$ signals that originate from intracellular stores in a variety of cells such as neuronal (Jalink et al., 1993; Durieux et al., 1992), platelets, normal as well as transformed fibroblasts (Jalink et al., 1990), epithelial cells (van Corven et al., 1989; Moolenaar, 1991), and *Xenopus* oocytes (Tigyi and Miledi, 1992; Durieux et al., 1992; Fernhout et al., 1992). LPA induces platelet aggregation (Schumacher et al., 1979; Tokumura et al., 1981; Gerrard et al., 1979; Simon et al., 1982) and smooth muscle contraction (Tokumura et al., 1980; Tokumura et al., 1994), and upon intravenous administration it induces species-dependent changes in blood pressure ((Schumacher et al., 1979; Tokumura et al., 1978).

LPA, when added to quiescent fibroblasts, stimulates DNA synthesis and cell division (van Corven et al., 1989; van Corven et al., 1992). The growth-like effects of LPA do not require the presence of peptide growth factors. This observation makes LPA different from endothelin or vasopressin, which require the presence of insulin or epidermal growth factor (Moolenaar, 1991) to sustain cell proliferation. A point to note is that, in $Sp^2$ myeloma cells, LPA was responsible for an antimitogenic response, which was mediated by an increase in cAMP levels (Tigyi et al., 1994; Fischer et al., 1998). Unlike the mitogenic pathway, the antimitogenic pathway was not affected by pertussis toxin (PTX). Also, on addition of forskolin and isobutyl methyl xanthin, the antimitogenic actions of LPA in Sp$^2$ myeloma cells were additive (Tigyi et al., 1994). In various cell types, LPA causes cytoskeletal changes, which include formation of focal adhesions and stress fibers in fibroblasts (Ridley and Hall, 1992). LPA also promotes the reversal and suppression of neuroblastoma differentiation by inducing the retraction of developing neurites (Jalink et al., 1994a; Jalink et al., 1994b). Addition of nanomole (nmol) amounts of LPA (Jalink and Moolenaar, 1992) to serum-starved N1E-115 neuroblastoma cells caused immediate neurite retraction, which was accompanied by rapid, but transient, rounding of the cell body (Jalink et al., 1993b). When a continuous presence of LPA is provided, neuroblastoma cells maintain their undifferentiated phenotype, but fail to undergo mitosis (Jalink et al., 1993b). Additional factors, such as insulin-like growth factors, were required for the progression of the cell cycle. Once the cells have undergone morphological differentiation, the addition of LPA reverses this morphological change. Thus, LPA-induced neurite retractions result from the contraction of the actin-cytoskeleton, rather than from loss of adhesion to the substratum (Jalink et al., 1993b; Jalink et al., 1994b).

LPA, similar to other physiological chemoattractants (e.g., interleukin-8), induces cell migration by a haptotactic mechanism in human monocytes (Zhou et al., 1995). In addition to inducing cell migration, LPA promotes the invasion of hepatoma and carcinoma cells into the monolayer of mesothelial cells (Imamura et al., 1993). The mechanism that underlies this invasion is still unclear, but it may be due to enhanced cell motility and increased cell adhesion. Finally, LPA is also known to block neonatal cardiomyocyte apoptosis (Umansky et al., 1997).

A unique natural phospholipid, namely cyclic-PA, was shown to be responsible for cellular actions that were similar to or opposite to other GPMs, depending on the cell type. When tested on the *Xenopus* oocyte, it elicited chloride current just like other GPMs; but its response was not desensitized by LPA (Fischer et al., 1998). Murakami-Murofushi et al. (1993) showed that cyclic-PA exhibited antiproliferative actions, unlike LPA, which induces proliferation.

PLGF receptors (PLGFRs) belong to a seven-transmembrane (7 TM) guanine nucleotide-binding regulatory protein (G protein)-coupled receptors (GPCR) superfamily. Seven-TM GPCRs are a family of cell-surface receptors that mediate their cellular responses via interacting with the heterotrimeric G-protein. A number of LPA receptors have been identified including, among others, EDG-2, EDG-4, EDG-7, and PSP-24. A phylogenetic tree illustrating the relatedness of these LPA receptors and others is shown in FIG. 1.

In 1996, Hecht et al. used differential hybridization to clone a cDNA encoding a putative serpentine receptor from mouse neocortical cell lines (Hecht et al., 1996). The gene was termed as ventricular zone gene-1 (Vzg-1). The gene was expressed in cortical neurogenic regions and encoded a protein with a molecular weight of 41 kDa (364 amino acids). Vzg-1 was very similar to an unpublished sheep sequence termed endothelial differentiation gene-2 (EDG-2). The same cDNA was also isolated as an orphan receptor from mouse and bovine libraries, and was known as rec1.3 (Macrae et al., 1996). It was widely distributed in the mouse tissue, with the highest expression in the brain and heart.

In 1996, Guo et al., using a PCR base protocol, isolated another putative LPA receptor PSP-24 (372 amino acids) from *Xenopus* oocyte (Guo et al., 1996). This receptor showed little similarity with Vzg-1/EDG-2/rec1.3 (Guo et al., 1996). A sequence based search for sphingolipid receptors, using the cDNA sequence of the EDG-2 human LPA receptor, led to two closely related GPCRs, namely, rat H218 (EDG-5, 354 amino acids) and EDG-3 (378 amino acids) (An et al., 1997a). Northern analysis showed a high expression of mRNA that encoded EDG-3 and EGD-5 in heart tissue.

The recent identification of EDG-2 as a functional receptor for LPA prompted An et al. to perform a sequence-based search for a novel subtype of LPA receptor (An et al., 1998a). A human cDNA, encoding a GPCR, was discovered and designated EDG-4 (An et al., 1998a). Northern blot analysis showed that, although EDG-2 and EDG-4 both serve as GPM receptors, their tissue distributions were very different. Unlike EDG-2, EDG-4 was primarily expressed in peripheral blood leukocytes and testes (An et al., 1998a).

PCR amplification cDNA from human Jurkat T cells identified a previously unknown GPCR that belongs to the EDG family. The identified GPCR was designated EDG-7. It has a molecular mass of 40 kDa (353 amino acids). Northern blot analysis of EDG-7 expression in human tissues showed that it is expressed in heart, pancreas, prostate, and testes (Bandoh et al., 1999). Thus, there are two distinct families of PLGFs receptors PSP24 and EDG; with a total of ten individual PLGFRs (FIG. 1). The list continues to grow.

These various receptors can be classified based on their ligand specificities for GPMs or SPMs, as shown in Table 1 below.

TABLE 1

Phospholipid Growth Factor Receptor, Length and Principle Ligand

| PLGFR | Number of amino acids | Principle Ligand |
|---|---|---|
| EDG-1 | 381 | SPP |
| EDG-2 | 364 | LPA |
| EDG-3 | 378 | SPP |
| EDG-4 | 382 | LPA |
| EDG-5 | 354 | SPP |
| EDG-6 | 385 | SPP |
| EDG-7 | 353 | LPA |
| EDG-8 | 400 | SPP |
| Xenopus PSP24 | 372 | LPA |
| Murine PSP24 | 373 | LPA |

*Xenopus* PSP24 and murine expressed PSP24 specifically transduce GPM (LPA, Fischer et al., 1998) evoked oscillatory chloride-currents. These are not structurally homologous to the EDG family (Tigyi and Miledi, 1992; Fernhout et al., 1992). The EDG family can be divided into two distinct subgroups. The first group includes EDG-2, EDG-4, and EDG-7, which serve as receptors for only GPM (Hecht et al., 1996; An et al., 1998a; Bandoh et al., 1999; An et al., 1998b) and transmit numerous signals in response to ligand binding. The second group involves EDG-1, EDG-3, EDG-5, EDG-6, and EDG-8, and is specific for SPMs (An et al., 1997a; Im et al., 2000; van Brocklyn et al., 1998; van Brocklyn et al., 2000; Spiegel and Milstein, 2000). Principle tissue expression of the various PLGFR's is shown in Table 2 below.

TABLE 2

Human Tissue Expression of Phospholipid Growth Factor Receptors

| PLGFR | Human Tissue with Highest Expression |
|---|---|
| EDG-1 | Ubiquitous |
| EDG-2 | Cardiovascular, CNS, Gonadal tissue, GI |
| EDG-3 | Cardiovascular, Leukocyte |
| EDG-4 | Leukocyte, Testes |
| EDG-5 | Cardiovascular, CNS, Gonadal tissue, Placenta |
| EDG-6 | Lymphoid, Hematopoietic tissue |
| EDG-7 | Heart, Pancreas, Prostate, Testes |
| EDG-8 | Brain |
| PSP24 | CNS |

PLGFs activate multiple G-protein-mediated signal transduction events. These processes are mediated through the heterotrimeric G-protein families $G_{q/11}$, $G_{i/o}$, and $G_{12/13}$ (Moolenaar, 1997; Spiegel and Milstein, 1995; Gohla, et al., 1998).

The $G_{q/11}$ pathway is responsible for phospholipase C (PLC) activation, which in turn induces inositol triphosphate ($IP_3$) production with subsequent mobilization of $Ca^{2+}$ in a wide variety of cells (Tokumura, 1995). In some cells, this response is PTX-sensitive, implying that there is involvement of multiple PTX-sensitive and insensitive pathways (Tigyi et al., 1996). This pathway is also responsible for the diacyl glycerol (DAG)-mediated activation of protein kinase C (PKC). PKC activates cellular phospholipase D (PLD), which is responsible for the hydrolysis of phosphatidyl choline into free choline and PA (van der Bend et al., 1992a). Also, PLC is capable of activating MAP kinase directly, or via DAG activation of PKC in some cell types (Ghosh et al., 1997).

The mitogenic-signaling pathway is mediated through the G-protein heterotrimeric $G_{i/o}$ subunit. Transfection studies indicate that the $G_{i\beta\gamma}$ dimer rather than the αi subunit is responsible for Ras-MAP kinase activation. The activation of Ras is preceded by the transactivation of the receptor tyrosine kinases (RTKs) such as EGF (Cunnick et al., 1998) or PDGF receptors (Herrlich et al., 1998). The transactivated RTKS activate Ras, which leads to the activation of MAP kinases (ERK 1,2) via Raf. The $G_{i\alpha}$ subunit, which is PTX-sensitive, inhibits adenylyl cyclase (AC), resulting in βγ dimer docking to a G-protein-coupled receptor kinase (GRKs) that phosphorylates and desensitizes the receptor. The phosphorylated receptor is recruited by β-arrestin, thus recruiting src kinase, which phosphorylates the EGF-receptor, generating its active conformation (Lin et al., 1997; Ahn et al., 1999; Luttrell et al., 1999). The transactivated RTKs, in turn, activate Ras, which leads to the activation of MAP kinases (ERK 1,2) via Raf. The $G_{i\alpha}$ subunit, which is PTX-sensitive, inhibits AC, resulting in decreased levels of cyclic-AMP (cAMP). The opposite cellular effects by LPA, that is, mitogenesis and antimitogenesis, are accompanied by opposing effects on the cAMP second messenger system. Mitogenesis is mediated through the $G_{i\alpha}$ pathway, which results in decreased levels of cAMP (van Corven et al., 1989; van Corven et al., 1992), whereas antimitogenesis is accompanied by a non-PTX sensitive $Ca^{2+}$-dependent elevation of cAMP (Tigyi et al., 1994; Fischer et al., 1998).

In contrast, very little is known about the PTX-insensitive $G_{12/13}$ signaling pathway, which leads to the rearrangement of the actin-cytoskeleton. This pathway may also involve the transactivation of RTKs (Lin et al., 1997; Ahn et al., 1999; Luttrell et al., 1999; Gohla et al., 1998) and converge on a small GTPase, Rho (Moolenaar, 1997). Much more is known about the down-stream signaling of Rho because various protein partners have been isolated and identified. Rho activates Ser/Thr kinases, which phosphorylate, and as a result inhibit, myosin light chain phosphatase (MLC-phosphatase) (Kimura et al., 1996). This path results in the accumulation of the phosphorylated form of MLC, leading to cytoskeletal responses that lead to cellular effects like retraction of neurites (Tigyi and Miledi, 1992; Tigyi et al., 1996; Dyer et al., 1992; Postma et al., 1996; Sato et al., 1997), induction of stress fibers (Ridley and Hall, 1992; Gonda et al., 1999), stimulation of chemotaxis (Jalink et al., 1993a), cell migration (Zhou et al., 1995; Kimura et al., 1992), and tumor cell invasiveness (Imamura et al., 1993; Imamura et al., 1996). The PLGF-induced, Rho-mediated, tumor cell invasiveness is blocked by C. Botulinium C3-toxin, which specifically ribosylates Rho in an ADP-dependent mechanism (Imamura et al., 1996).

Rho also has the ability to stimulate DNA synthesis in quiescent fibroblasts (Machesky and Hall, 1996; Ridley, 1996). The expression of Rho family GTPase activates serum-response factor (SRF), which mediates early gene transcription (Hill et al., 1995). Furthermore, PLGF (LPA) induces tumor cell invasion (Imamura et al., 1996); however, it is still unclear whether it involves cytoskeletal changes or gene transcription, or both.

By virtue of LPA/LPA receptor involvement in a number of cellular pathways and cell activities such as proliferation and/or migration, as well as their implication in wound healing and cancer, it would be desirable to identify novel compounds which are capable of acting, preferably selectively, as either antagonists or agonists at the LPA receptors identified above.

There are currently very few synthetic or endogenous LPA receptor inhibitors which are known. Of the antagonists reported to date, the most work was done on SPH, SPP, N-palmitoyl-1-serine (Bittman et al., 1996), and N-palmitoyl-1-tyrosine (Bittman et al., 1996). It is known that the above-mentioned compounds inhibit LPA-induced chloride currents in the *Xenopus* oocyte (Bittman et al., 1996; Zsiros et al., 1998). However, these compounds have not been studied in all cell systems. It is also known that SPP inhibits tumor cell invasiveness, but it is uncertain whether SPP does so by being an inhibitor of LPA or via the actions of its own receptors. N-palmitoyl-1-serine and N-palmitoyl-1-tyrosine also inhibited LPA-induced platelet aggregation (Sugiura et al., 1994), but it remains to be seen whether these compounds act at the LPA receptor. Lysophosphatidyl glycerol (LPG) was the first lipid to show some degree of inhibition of LPA actions (van der Bend et al., 1992b), but it was not detectable in several LPA-responsive cells types (Liliom et al., 1996). None of these inhibitors was shown to selectively act at specific LPA receptors.

A polysulfonated compound, Suramin, was shown to inhibit LPA-induced DNA synthesis in a reversible and dose-dependent manner. However, it was shown that Suramin does not have any specificity towards the LPA receptor and blocked the actions of LPA only at very high millimolar (mM) concentrations (van Corven et al., 1992).

The present invention is directed to overcoming the deficiencies associated with current LPA agonists and LPA antagonists.

SUMMARY OF THE INVENTION

The present invention relates to compounds according to formula (I) as follows:

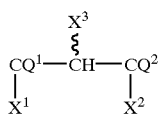

wherein, at least one of $X^1$, $X^2$, and $X^3$ is $(HO)_2PO-Z^1-$ or $(HO)_2PO-Z^2-P(OH)O-Z^1-$, $X^1$ and $X^2$ are linked together as $-O-PO(OH)-O-$, or $X^1$ and $X^3$ are linked together as $-O-PO(OH)-NH-$;

at least one of $X^1$, $X^2$, and $X^3$ is $R^1-Y^1-A-$ with each being the same or different when two of $X^1$, $X^2$, and $X^3$ are $R^1-Y^1-A-$, or $X^2$ and $X^3$ are linked together as $-N(H)-C(O)-N(R^1)-$;

optionally, one of $X^1$, $X^2$, and $X^3$ is H;

A is either a direct link, $(CH_2)_k$ with k being an integer from 0 to 30, or O;

$Y^1$ is $-(CH_2)_l$ with l being an integer from 1 to 30, $-O-$,

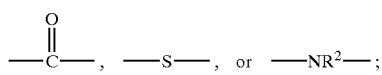

$Z^1$ is $-(CH_2)_m-$ or $-O(CH_2)_m-$ with m being an integer from 1 to 50, $-C(R^3)H-$, $-NH-$, $-O-$, or $-S-$;

$Z^2$ is $-(CH_2)_n-$ or $-O(CH_2)_n-$ with n being an integer from 1 to 50 or $-O-$;

$Q^1$ and $Q^2$ are independently $H_2$, $=NR^4$, $=O$, or a combination of H and $-NR^5R^6$;

$R^1$, for each of $X^1$, $X^2$, or $X^3$, is independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl,

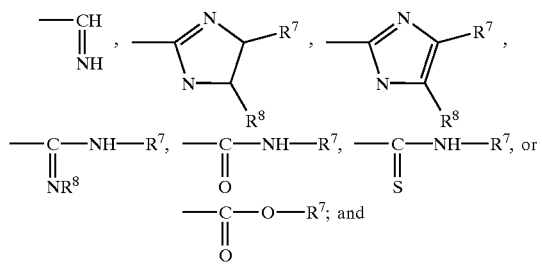

$R^2$, $R^3$, $R^4$, $R^5$, $R^6$, $R^7$, and $R^8$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl;

wherein the compound of formula I is not lysophosphatidic acid, phosphatidic acid, cyclic phosphatidic acid, alkenyl glycerolphosphate, dioctyl glycerol pyrophosphate, or N-palmitoyl-L-serine.

Also disclosed are pharmaceutical compositions which include a pharmaceutically-acceptable carrier and a compound of the present invention.

A further aspect of the present invention relates to a method of inhibiting LPA activity on an LPA receptor which includes providing a compound of the present invention which has activity as an LPA receptor antagonist and contacting an LPA receptor with the compound under conditions effective to inhibit LPA-induced activity of the LPA receptor.

Another aspect of the present invention relates to a method of modulating LPA receptor activity which includes providing a compound of the present invention which has activity as either an LPA receptor agonist or an LPA receptor antagonist and contacting an LPA receptor with the compound under conditions effective to modulate the activity of the LPA receptor.

Still another aspect of the present invention relates to a method of treating cancer which includes providing a compound of the present invention and administering an effective amount of the compound to a patient in a manner effective to treat cancer.

Yet another aspect of the present invention relates to a method of enhancing cell proliferation which includes providing a compound the present invention which has activity as an agonist of an LPA receptor and contacting the LPA receptor on a cell with the compound in a manner effective to enhance LPA receptor-induced proliferation of the cell.

A further aspect of the present invention relates to a method of treating a wound which includes providing a compound of the present invention which has activity as an agonist of an LPA receptor and delivering an effective amount of the compound to a wound site, where the compound binds to LPA receptors on cells that promote healing of the wound, thereby stimulating LPA receptor agonist-induced cell proliferation to promote wound healing.

A still further aspect of the present invention relates to a method of making the compounds of the present invention. One approach for making the compounds of the present invention includes:

reacting $(Y^2O)_2PO-Z^{11}-Z^{13}$ or $(Y^2O)_2PO-Z^{12}-P(OH)O-Z^{11}-Z^{13}$, where $Z^{11}$ is $-(CH_2)_m-$ or $-O(CH_2)_m-$ with m being an integer from 1 to 50, $-C(R^3)H-$, or $-O-$;

$Z^{12}$ is $-(CH_2)_n-$ or $-O(CH_2)_n-$ with n being an integer from 1 to 50 or $-O-$;

$Z^{13}$ is H or a first leaving group or $-Z^{11}-Z^{13}$ together form the first leaving group; and $Y^2$ is H or a protecting group, with an intermediate compound according to formula (VI)

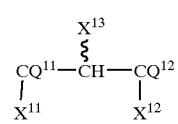

where, at least one of $X^{11}$, $X^{12}$, and $X^{13}$ is $R^{11}-Y^{11}-A-$ with each being the same or different when two of $X^{11}$, $X^{12}$, and $X^{13}$ are $R^{11}-Y^{11}-A-$, or $X^{12}$ and $X^{13}$ are linked together as $-N(H)-C(O)-N(R^{11})-$;

at least one of $X^{11}$, $X^{12}$, and $X^{13}$ is OH, $NH_2$, SH, or a second leaving group;

optionally, one of $X^{11}$, $X^{12}$, and $X^{13}$ is H;

A is either a direct link, $(CH_2)_k$ with k being an integer from 0 to 30, or O;

$Y^{11}$ is —$(CH_2)_l$— with l being an integer from 1 to 30, —O—,

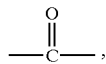

$Q^1$ and $Q^2$ are independently $H_2$, =$NR^{13}$, =O, a combination of H and —$NR^{14}R^{15}$;

$R^{11}$, for each of $X^{11}$, $X^{12}$, or $X^{13}$, is independently hydrogen, a straight or branched-chain C1 to C30 alkyl, a straight or branched-chain C2 to C30 alkenyl, an aromatic or heteroaromatic ring with or without

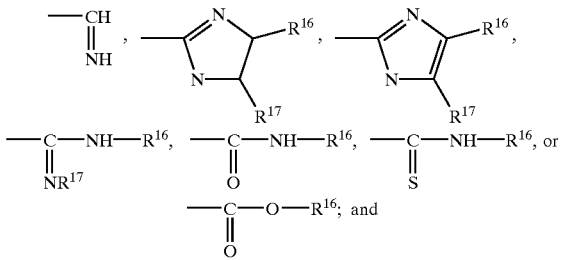

mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl, $R^{12}$, $R^{13}$, $R^{14}$, $R^{15}$, $R^{16}$, and $R^{17}$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl;

followed by a de-protection step, if necessary, with both said reacting and the deprotection step being performed under conditions effective to afford a compound according to formula (I) where one or two of $X^1$, $X^2$, and $X^3$ is (HO)$_2$PO-$Z^1$- or (HO)$_2$PO-$Z^2$-P(OH)O-$Z^1$-.

The compounds of the present invention which have been identified herein as being either agonists or antagonists of one or more LPA receptors find uses to inhibit or enhance, respectively, biochemical pathways mediated by LPA receptor signaling. By modulating LPA receptor signaling, the antagonists and agonists find specific and substantial uses in treating cancer and enhancing wound healing.

BRIEF DESCRIPTION OF THE DRAWINGS

FIG. 3 illustrates the synthesis scheme employed for preparation of serine amide phosphate compounds 55–59.

FIG. 4 illustrates the synthesis scheme employed for preparation of biphosphate compounds 66–68.

FIGS. 5A–B illustrate synthesis of biphosphate compounds. FIG. 5A illustrates the synthesis scheme employed for preparation of 1,2-biphosphate compounds 85–92. FIG. 5B illustrates a synthesis scheme for preparing 1,3-biphosphate compounds.

FIG. 13 illustrates a synthesis scheme for preparation of conformationally restrained, cyclic phosphate compounds.

FIG. 14 illustrates a synthesis scheme for preparation of conformationally restrained compounds with a free phosphate moiety.

FIG. 15 illustrates an alternative synthesis scheme for preparing 2-monophosphates.

FIG. 21 is a graph illustrating the dose-dependent inhibition of LPA-induced chloride currents in *Xenopus* oocytes by extracellular application of 56 (SAP, 14:0).

FIG. 22 is a graph illustrating the dose-dependent inhibition of LPA-induced chloride currents in *Xenopus* oocytes by extracellular application of 57 (SAP, 18:0).

FIGS. 23A–B are graphs illustrating the dose-dependent inhibition of LPA-induced chloride currents in *Xenopus* oocytes by extracellular application of 66 (MAGDP, 18:0). The arrow indicates the time of the intracellular injection of 5 μM 66, followed by the extracellular application of LPA.

FIGS. 28A–C are graphs illustrating the dose response relationship for $Ca^{2+}$ responses in RH7777 cells heterologously expressing Edg-2 (28A), Edg-4 (28B), or Edg-7 (28C). Each data point represents the average of at least three measurements±S.D.

FIGS. 29A–D are graphs illustrating DGPP 8:0 inhibition of $Ca^{2+}$ responses elicited by LPA in Edg-2 and -7, but not Edg-4 expressing RH7777 cells. RH7777 cells, expressing Edg-2, -4, or -7, were exposed to a mixture of 100 nM LPA 18:1 and 1 μM DGPP 8:0. Control cells were exposed to 100 nM LPA 18:1. Representative $Ca^{2+}$ responses are shown for stable Edg-2 (29A), Edg-4 (29B), and Edg-7 (29C) expressing cells, or cells transiently expressing Edg-4 (29D).

FIGS. 30A–C are graphs which illustrate the pharmacological characterization of the inhibition of the LPA response by DGPP 8:0 in RH7777 cells expressing Edg-7 (Edg-7 cells). Cells were exposed to a 250 nM concentration of LPA 18:1 mixed with increasing concentrations of DGPP 8:0 and the peak area of the resulting $Ca^{2+}$ responses were measured (30A). Cells were also exposed to increasing concentrations of LPA 18:1 mixed with a 500 nM concentration of DGPP 8:0 (30B). Edg-7 cells were exposed to a 250 nM concentration of LPA 18:1 mixed with a 500 nM concentration of the indicated lipid (30C). The peak areas of the $Ca^{2+}$ responses are represented as the average values of a minimum of three measurements±S.D.

FIGS. 31A–C are graphs which illustrate the pharmacological characterization of the inhibition of the LPA response by DGPP 8:0 in RH7777 cells expressing Edg-2 (Edg-2 cells). Stable Edg-2 cells exposed to a 250 nM concentration of LPA 18:1 mixed with increasing concentrations of DGPP 8:0 and peak areas of the $Ca^{2+}$ responses were measured (31A). Edg-2 cells were exposed to increasing concentrations of LPA 18:1 mixed with a 10 μM concentration of DGPP 8:0 (31B). Edg-2 cells exposed to a 250 nM concentration of LPA 18:1 mixed with a 10 μM concentration of the indicated lipid (31C). Responses are represented as the average values of a minimum of three measurements±S.D.

FIGS. 32A–B are graphs which illustrate the structure-activity relationship for DGPP in Edg-4-expressing RH7777 cells. Stable Edg-4 cells exposed to a 500 nM concentration of LPA 18:1 mixed with a 5 μM concentration of the indicated lipids (32A). Cells transiently expressing Edg-4 cells were exposed to a 100 nM concentration of LPA 18:1 mixed with a 1 μM concentration of the indicated lipids (32B). The peak areas of the $Ca^{2+}$ responses were measured and are represented as the average values of a minimum of three measurements±S.D.

FIGS. 33A–C are graphs which illustrate the pharmacological characterization of DGPP 8:0 on the LPA-elicited $Cl^-$ currents in Xenopus oocytes. Oocytes were exposed to a 5 nM concentration of LPA 18:1 mixed with increasing concentrations of DGPP 8:0 and the peak amplitude of the resulting oscillatory $Cl^-$ currents were measured (33A). Oocytes were exposed to increasing concentrations of LPA 18:1 mixed with a 200 nM concentration of DGPP 8:0 (33B). Data points represent the average values of a minimum of three measurements±S.D. Oocytes were treated with 5 nM LPA 18:1, or a mixture of 5 nM LPA 18:1 and 1 μM DGPP 8:0 as indicated (33C). The intracellular injection of 1 μM DGPP 8:0 is indicated by the arrow.

FIGS. 34A–D are graphs which illustrate DGPP 8:0 inhibiting the LPA-elicited $Ca^{2+}$ responses in NIH3T3 fibroblasts and HEY ovarian cancer cells. RT-PCR analysis of NIH3T3 cells for Edg and PSP24 receptor transcripts (34A). NIH3T3 cells were exposed to a 100 nM concentration of LPA 18:1, or S1P, mixed with a 10 μM concentration of DGPP 8:0 (34B). RT-PCR analysis of HEY cells for the presence of the Edg and PSP24 transcripts (34C). HEY cells were exposed to a 100 nM concentration of LPA 18:1, or S1P, mixed with a 1 μM concentration of DGPP 8:0 (34D). The peak areas of the resulting $Ca^{2+}$ responses were measured and are represented as the average of a minimum of three measurements±S.D.

DETAILED DESCRIPTION OF THE INVENTION

Figure 1:
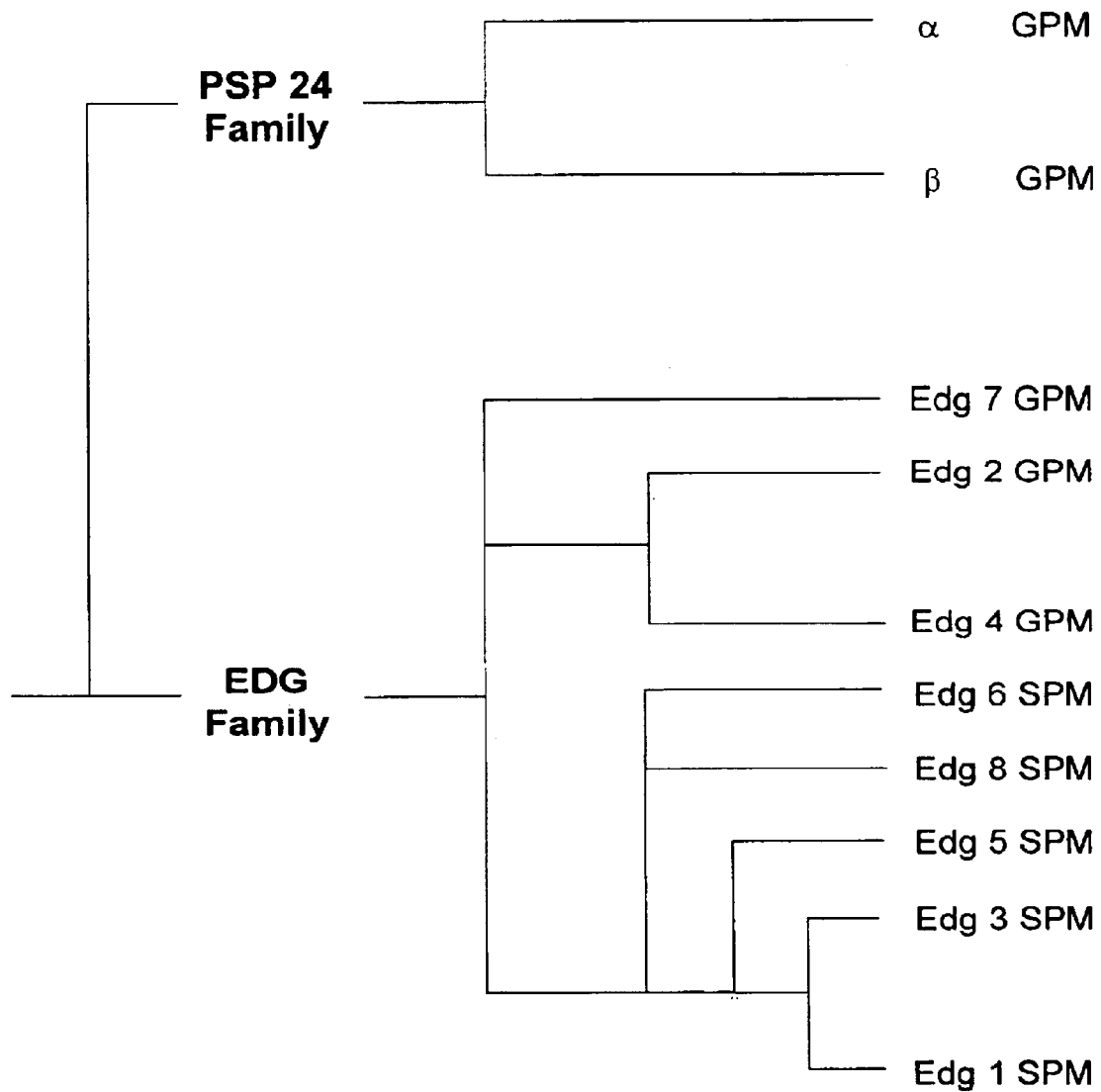
FIG. 1 is a phylogenetic tree illustrating the classification and relatedness of ten phospholipid growth factor receptors, including LPA receptors EDG-2, EDG-4, EDG-7, and PSP-24 (α,β).

One aspect of the present invention relates to a compound according to formula (I)

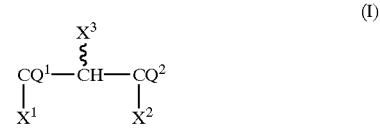

(I)

wherein, at least one of $X^1$, $X^2$, and $X^3$ is $(HO)_2PO-Z^1-$ or $(HO)_2PO-Z^2-P(OH)O-Z^1-$, $X^1$ and $X^2$ are linked together as $-O-PO(OH)-O-$, or $X^1$ and $X^3$ are linked together as $-O-PO(OH)-NH-$;

at least one of $X^1$, $X^2$ and $X^3$ is $R^1-Y^1-A-$ with each being the same or different when two of $X^1$, $X^2$, and $X^3$ are $R^1-Y^1-A-$, or $X^2$ and $X^3$ are linked together as $-N(H)-C(O)-N(R^1)-$;

optionally, one of $X^1$, $X^2$, and $X^3$ is H;

A is either a direct link, $(CH_2)_k$ with k being an integer from 0 to 30, or O;

$Y^1$ is $-(CH_2)_l-$ with l being an integer from 1 to 30, $-O-$,

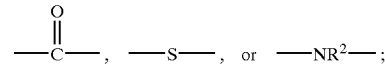

$Z^1$ is $-(CH_2)_m$ or $-O(CH_2)_m-$ with m being an integer from 1 to 50, $-C(R^3)H-$, $-NH-$, $-O-$, or $-S-$;

$Z^2$ is —$(CH_2)_n$— or —$O(CH_2)_n$— with n being an integer from 1 to 50 or —O—;

$Q^1$ and $Q^2$ are independently $H_2$, =$NR^4$, =O, a combination of H and —$NR^5R^6$;

$R^1$, for each of $X^1$, $X^2$, or $X^3$, is independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl,

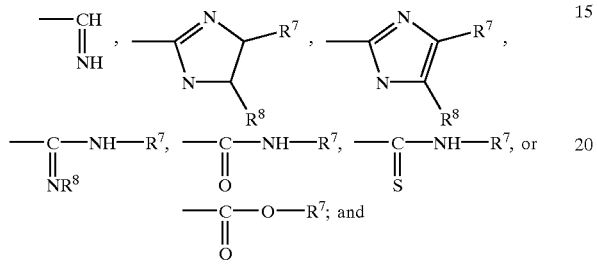

$R^2$, $R^3$, $R^4$, $R^5$, $R^6$, $R^7$, and $R^8$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl.

For each of the above-identified R groups (e.g., $R^1$-$R^8$), it is intended that straight chain alkyls have the formula —$(CH_2)_xCH_3$ where x is from 0 to 29; branched chain alkyls have the formula as defined above for straight chain alkyl, except that one or more $CH_2$ groups are replaced by CHW groups where W is an alkyl side chain; straight chain alkenyls have the formula —$(CH_2)_{xa}CH$=$CH(CH_2)_{xb}CH_3$ where xa and xb each are from 0 to 27 and (xa+xb) is not more than 27; and branched chain alkenyls have the formula as defined above for straight chain alkenyl, except that one or more $CH_2$ groups are replaced by CHW groups or a CH group is replaced by a CW group, where W is an alkyl side chain.

Aromatic or heteroaromatic rings include, without limitation, phenyls, indenes, pyrroles, imidazoles, oxazoles, pyrazoles, pyridines, pyrimidines, pyrrolidines, piperidines, thiophenes, furans, napthals, bi-phenyls, and indoles. The aromatic or heteroaromatic rings can include mono-, di-, or tri-substitutions of the ring located at the ortho, meta, or para positions on the rings relative to where the ring binds to the $Y^1$ group of the $R^1$—$Y^1$-A- chain. Substitutions on the rings can include, without limitation, alkyl, alkoxy, amine (including secondary or tertiary amines), alkylamine, amide, alkylamide, acids, alcohols.

Acyl groups can include either alkyl, alkenyl, or aromatic or heteroaromatic rings as described above.

Arylalkyl and aryloxyalkyl groups can include, without limitation, straight or branched-chain C1 to C30 alkyl groups as described above, with the alkyl group binding to the $Y^1$ group of the $R^1$—$Y^1$-A- chain.

Specifically excluded from the above-identified definition of the compound according to formula (I) are the following previously known endogenous or synthetic compounds: lysophosphatidic acid, phosphatidic acid, cyclic phosphatidic acid, alkenyl glyerolphosphate, dioctyl-glycerol pyrophosphate, and N-palmitoyl-L-serine.

Exemplary compounds according to formula (I) are the subclass compounds according to formulae (II)–(V) below.

In the structures of formulae (II)A and (II)B, $Q^1$ and $Q^2$ are both $H_2$; one of $X^1$, $X^2$, and $X^3$ is $(HO)_2PO$-$Z^2$-$P(OH)O$-$Z^1$-, with $Z^1$ and $Z^2$ being O; and two of $X^1$, $X^2$, and $X^3$ are $R^1$—$Y^1$-A-, with A being a direct link and $Y^1$ being O for each. Each $R^1$ is defined independently as above for formula (I).

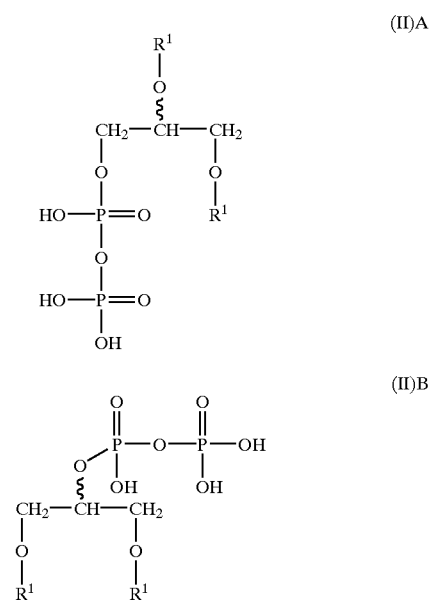

In the structures of formula (III), $Q^1$ is $H_2$; $Q^2$ is =O; $X^1$ is $(HO)_2PO$-$Z^1$-, with $Z^1$ being O; and $X^2$ and $X^3$ are $R^1$—$Y^1$-A-, with A being a direct link and $Y^1$ being —NH— for each. Each $R^1$ is defined independently as above for formula (I). Preferred species of within the scope of formula III are where $X^3$ is —$NH_2$ and $X^2$ is —$NHR^1$ with $R^1$ being a C14 to C18 alkyl, more preferably either a C14 alkyl or a C18 alkyl; or where $X^3$ is —$NHR^1$ with $R^1$ being an acetyl group and $X^2$ is —$NHR^1$ with $R^1$ being a C14 alkyl.

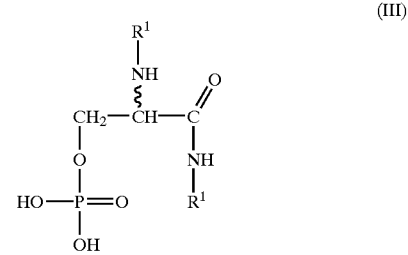

In the structures of formula (IV), $Q^1$ is =$NR^4$; $Q^2$ is $H_2$; $X^1$ and $X^2$ are linked together as —O—PO(OH)—O—; and $X^3$ is $R^1$—$Y^1$-A-, with A being a direct link and $Y^1$ being —NH—. $R^1$ and $R^4$ are as defined above for formula (I).

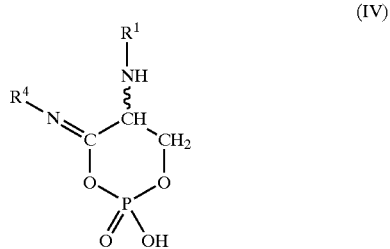

(IV)

In the structures of formulae (V)A and (V)B, $Q^1$ and $Q^2$ are both $H_2$; two of $X^1$, $X^2$, and $X^3$ are $(HO)_2PO-Z^1-$, with $Z^1$ being O for each; and one of $X^1$, $X^2$, and $X^3$ is $R^1$—$Y^1$-A-, with A being a direct link and $Y^1$ being —O—. $R^1$ is as defined above for formula (I). Preferred species within the scope of formulae (V)A and (V)B include the compounds where $R^1$ is an acyl including a C21 alkyl or where $R^1$ is a C18 alkyl.

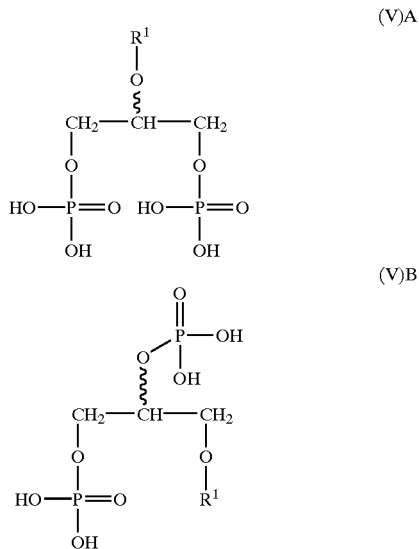

The compounds according to formula (I), as well as the subgenus compounds according to formulae (II)A, (II)B, (III), (IV), (V)A, and (V)B, can be prepared using the synthesis schemes described below.

Figure 2:
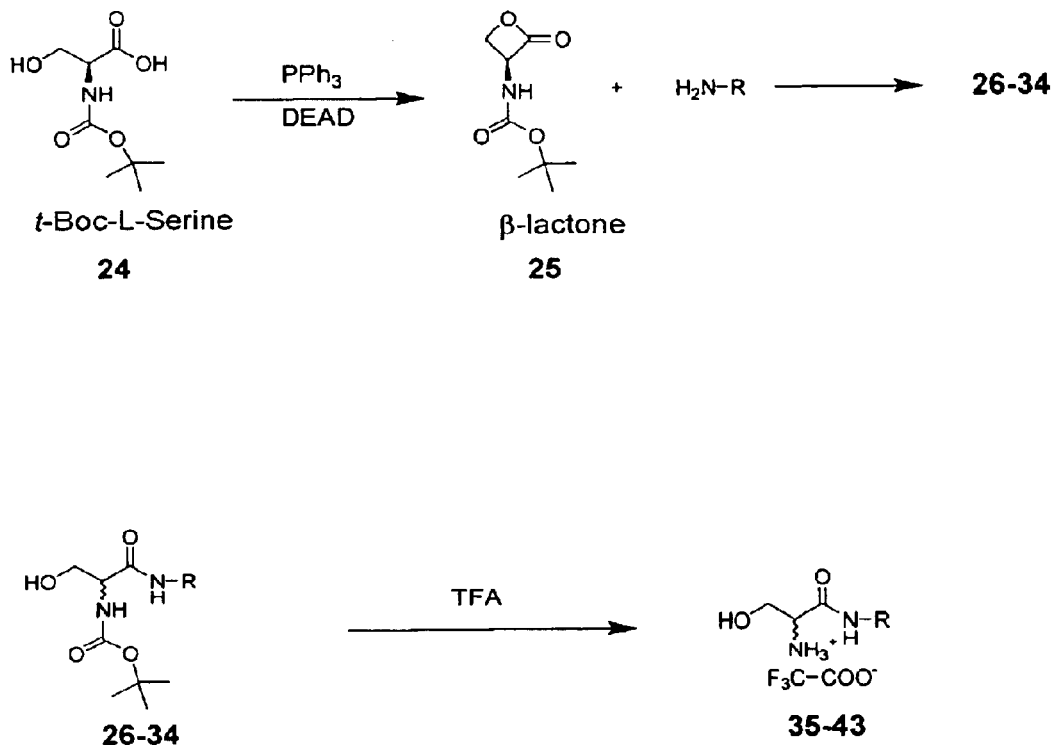
FIG. 2 illustrates the synthesis scheme employed for preparation of serine amide compounds 35–43.

To synthesize the serine amides (SA) and serine amide phosphate (SAP) series (formula (III)), the precursor t-Boc protected β-lactone (25) was first synthesized. Starting with commercially available t-Boc-L-serine (FIG. 2, 24), triphenyl phosphine ($PPh_3$) and diethylazidodicarboxylate (DEAD) were introduced under Mitsunobo conditions, affording compound 25 in ca. 50% yield (Sun et al., 1996). Attempts using procedure developed by Sun et al. to open the highly labile β-lactone 25 with various primary amines to obtain hydroxy amides 26–34 failed, in spite of using various reagents (triethyl amine, etc.). Instead, by refluxing the primary amines with the β-lactone in THF, the t-Boc protected hydroxy amides 26–34 were obtained. Compounds 26–34 were purified using flash column chromatography. Trifluoroacetic acid (TFA)-mediated removal of the t-Boc protecting group afforded compounds 35–43 as TFA salts.

To synthesize compounds 55–59, the t-Boc protected hydroxy amides 26–30 were phosphorylated. A careful study of the final compound suggested that the final compound would possess a highly hydrophobic region and a highly hydrophilic region. Both regions may cause problems during the extraction process and/or attach to the column during the purification stage. To circumvent these potential problems, phosphoramidate chemistry was employed. By using phosphoramidate chemistry, it was hypothesized that the phosphate hydroxyl groups could be protected to render the molecule completely hydrophobic, thereby facilitating its smooth purification.

Essentially, a combination of procedures was used to obtain the desired products (55–59) (Lynch et al., 1997; Bittman et al., 1996; Liu et al., 1999). Starting hydroxyamides (26–30) were repeatedly washed with anhydrous pyridine, and dried in high vacuum for over 48 hrs. The pyridine-washed hydroxyamides were maintained under an atmosphere of argon. 1H-tetrazole and a freshly distilled 1:1 mixture of THF/$CH_2Cl_2$ were then added. The phosphorylating agent, dibenzyldiisopropyl phosphoramidate, was added. After monitoring the reaction by TLC, the phosphonate was oxidized to the phosphate in situ with peracetic acid. The reaction mixture was purified via column chromatography to afford compounds 50–54 as benzyl-protected phosphates. The removal of the protecting benzyl groups was carried out in ethanol by subjecting compounds 50–54 to catalytic reduction using 10% palladium on activated carbon (Pd/C) under $H_2$ atmosphere at 60 psi to yield compounds 55–59 (FIG. 3). Reacting 56 with acetic anhydride afforded compound 56a (FIG. 3).

Figure 5B:
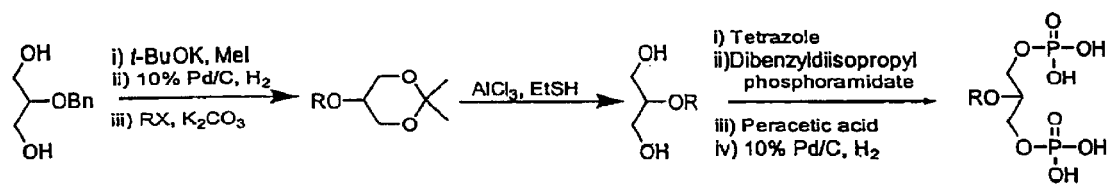

Once the phosphorylation technique was elucidated for the synthesis of the SAP series (compounds 55–59), a similar procedure was used for the synthesis of bisphosphates (formulae (V)A and (V)B) (FIGS. 4 and 5A–B). The commercially available diols 60–62 were washed with anhydrous pyridine, and were dried for 48 hrs under high vacuum. These dried diols (60–62) were dissolved in freshly distilled 1:1 THF/$CH_2Cl_2$, followed by the addition of 1H-tetrazole. To this stirred mixture was added dibenzyldiisopropyl phosphoramidate. The reaction mixture was monitored via TLC, and at the appropriate time the phosphonate was oxidized to the phosphate in situ with peracetic acid. The reaction mixture was purified with column chromatography to afford compounds 63–65 as benzyl-protected bisphosphates. The removal of the protecting benzyl groups was carried out in ethanol by subjecting compounds 63–65 to catalytic reduction using 10% palladium on activated carbon (Pd/C) under $H_2$ atmosphere at 60 psi to yield compounds 66–68 as bisphosphates. A similar procedure as described above for the synthesis of 66–68 was followed to obtain compounds 85–92.

While compounds 85–92 are 1,2-biphosphates, FIG. 5B illustrates the synthesis of 1,3-biphosphates. Commercially available 2-phenoxy-1,3-propane-diol was used as the starting material. The starting compound was first protected with t-BuOK in the presence of methyl iodide, followed by catalytic hydrogenation to give an intermediate which was then reacted with a halide (RX, where R is as defined above for $R^1$). The recovered intermediate was subsequently treated with $AlCl_3$ in the presence of ethyl-SH to yield a 1,3 diol possessing the RO group bound to C2 of the backbone. The recovered 1,3 diol was dissolved in freshly distilled 1:1 THF/$CH_2Cl_2$, followed by the addition of 1H-tetrazole. To this stirred mixture was added dibenzyldiisopropyl phosphoramidate. The reaction mixture was monitored via TLC, and at the appropriate time the phosphonate was oxidized to the phosphate in situ with peracetic acid. The reaction mixture was purified with column chromatography to afford benzyl-protected bisphosphate compounds. Removal of the protecting benzyl groups was carried out in ethanol by subjecting the compounds to catalytic reduction using 10% palladium on activated carbon (Pd/C) under $H_2$ atmosphere at 60 psi to yield 1,3-bisphosphate compounds.

Figure 6A:
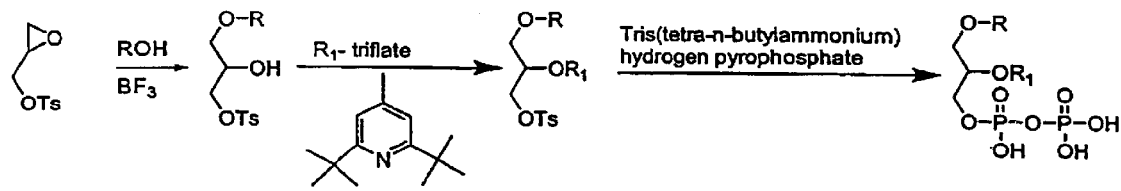
FIGS. 6A–B illustrate synthesis schemes for preparation of pyrophosphate compounds.
Figure 6B:
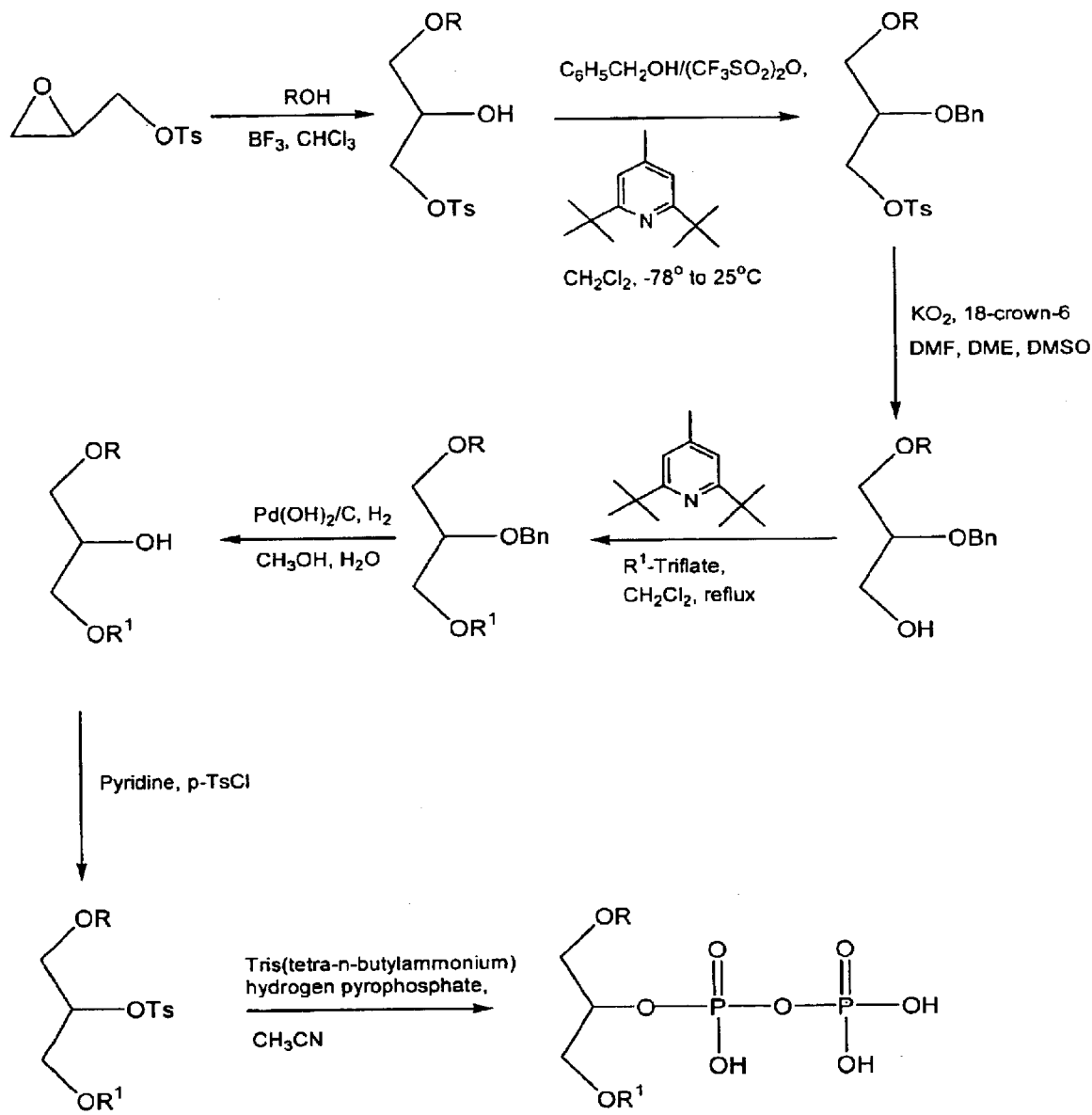

To synthesize the pyrophosphates of formulae (II)A and (II)B, glycidal tosylate ((2R)(-) or (2R)(+)) was used as the starting material (FIGS. 6A–B). Opening of the ring was catalyzed by a Lewis acid, such as $BF_3$, in the presence of an alcohol, affording an intermediate which was tosylate-protected at the C1 position. In the next step, the alcohol at the C2 position was replaced with an R group (e.g., $R^1$ as described above) using as excess of R-triflate and 2,6-di-tert-butyl-4-methylpyridine, affording the di-ether intermediate. Treatment of the di-ether intermediate with tris(tetra-n-butylammonium) hydrogen pyrophosphate caused nucleophilic attack of the tosylate, replacing the tosylate with a pyrophosphate substituent at the C1 position.

To produce the pyrophosphate of formula (II)B, the tosylate protected intermediate was treated with benzyl alcohol in the presence of triflic anhydride and 2,6-di-tert-butyl-4-methylpyridine, which benzylates the intermediate at the C2 position. The tosylate protecting group on the benzylate intermediate was removed first by the action of potassium superoxide in the presence of 18-crown-6, affording a hydroxyl group at the C1 position which was subject to replacement with an R group (e.g., $R^1$ as described above) using an excess of R-triflate and 2,6-di-tert-butyl-4-methylpyridine. The resulting di-ether intermediate still possessed the benzyl protecting group at the C2 position. The benzyl protecting group was removed by hydrogenation and the subsequent hydroxyl group was tosylated by the action of pyridine and p-toluenesulfonyl chloride, producing a di-ether bearing a tosyl group at the C2 position. The tosylate group was removed by nucleophilic attack upon treatment with tris(tetra-n-butylammonium) hydrogen pyrophosphate, replacing the tosylate with a pyrophosphate substituent at the C2 position.

Figure 16:
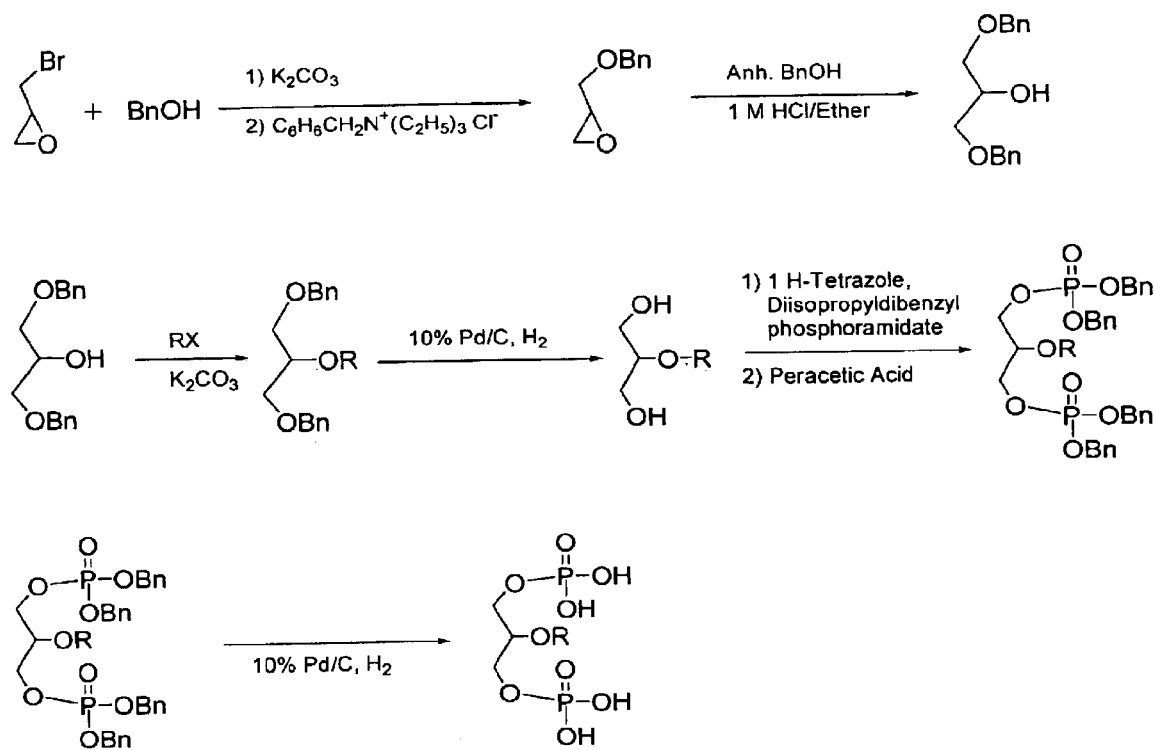
FIG. 16 illustrates an alternative synthesis scheme for preparing 1,3-bisphosphate compounds.

Alternative schemes for preparing phosphates and biphosphates (as well as pyrophosphates, phosphonates, etc.) are illustrated in FIGS. 15 and 16.

In FIG. 15, glycidal bromide was used as the starting material along with an alcohol (ROH). The reaction conditions included treatment with $K_2CO_3$ followed by treatment with the ammonium salt $C_6H_6CH_2N^+(C_2H_5)_3Cl^-$, resulting in displacement of the bromide with the R group. The ring of the glycidal intermediate was then opened following treatment with 1M HCl in ether and an alcohol ($R^1$OH), which afforded a di-ether intermediate having a hydroxy group at the C2 postion. The di-ether was mixed with 1H-tetrazole and to this stirred mixture was added dibenzyldiisopropyl phosphoramidate. The reaction mixture was monitored via TLC, and at the appropriate time the phosphonate was oxidized to the phosphate in situ with peracetic acid. The reaction mixture was purified with column chromatography to afford benzyl-protected phosphates. The removal of the protecting benzyl groups was carried out in ethanol by subjecting the benzyl-protected phosphates to catalytic reduction using 10% palladium on activated carbon (Pd/C) under $H_2$ atmosphere at 60 psi to yield monophosphate compounds.

In FIG. 16, a similar reaction scheme was employed, except instead of reacting the glycidal bromide with an alcohol (ROH), BnOH was used to protect the C3 site. The reaction conditions included treatment with $K_2CO_3$ followed by treatment with the ammonium salt $C_6H_6CH_2N^+(C_2H_5)_3Cl^-$, resulting in displacement of the bromide with the Bn group. The ring of the glycidal intermediate was then opened following treatment with 1M HCl in ether and annhydrous BnOH, which protected the C1 site. The resulting di-ether intermediate has a hydroxy group at the C2 postion. The di-ether was mixed with a halide salt (RX) in aqueous $K_2CO_3$, yielding a protected intermediate having an R group attached via ether bond at the C2 position. This intermediate was de-protected via catalytic reduction using 10% palladium on activated carbon (Pd/C) under $H_2$ atmosphere at 60 psi to yield a 1,3 diol. The diol was combined with 1H-tetrazole and to this stirred mixture was added dibenzyldiisopropyl phosphoramidate. The reaction mixture was monitored via TLC, and at the appropriate time the phosphonate was oxidized to the phosphate in situ with peracetic acid. The reaction mixture was purified with column chromatography to affords benzyl-protected phosphates. The removal of the protecting benzyl groups was carried out in ethanol by subjecting the benzyl-protected phosphates to catalytic reduction using 10% palladium on activated carbon (Pd/C) under $H_2$ atmosphere at 60 psi to yield 1,3 bisphosphates.

Figure 7A:
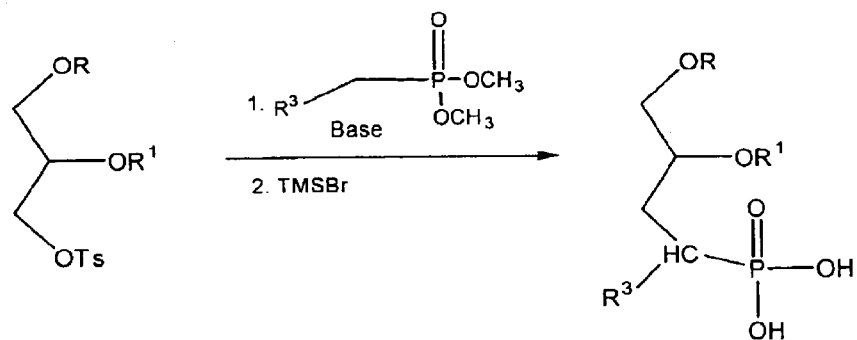
FIGS. 7A–C illustrate synthesis schemes for preparation of substituted mono-phosphates and mono-phosphonates from a tosylate-protected di-ether intermediate.
Figure 7B:
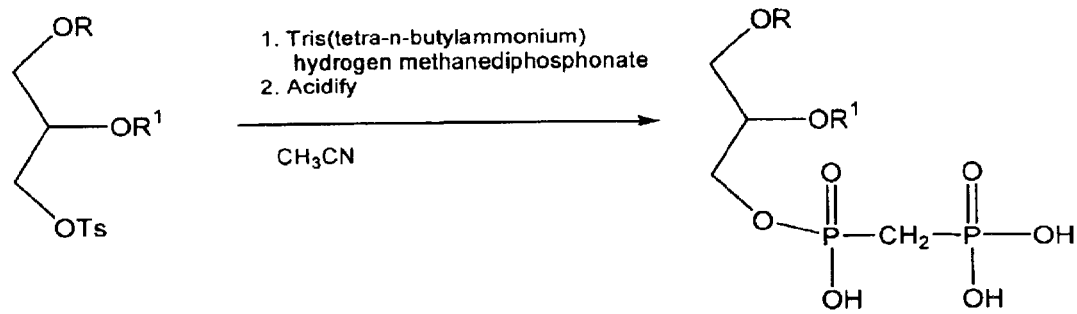
Figure 7C:
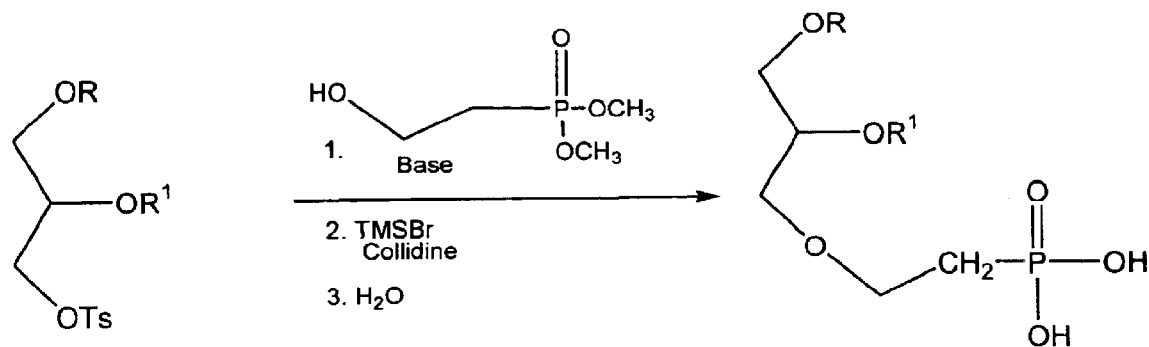

Using the di-ether intermediate prepared as shown in FIG. 6A (e.g., bearing R and $R^1$ substituents), a number of modified phosphates and phosphonates can be attached at the C1 site upon removal of the tosyl group. As shown in FIG. 7A, the intermediate is reacted under basic conditions with $X^4$-$Z^1$-PO(O-protecting group)$_2$ where $Z^1$ is —($R^3$)CH— and $X^4$ is H. The basic conditions remove the tosylate protecting group and allow the modified phosphate -$Z^1$—PO(O-protecting group)$_2$ to form a single bond to the C1 site. The protecting groups are removed following treatment with TMSBr, affording a —($R^3$)CH—PO(OH)$_2$ group at the C1 site. As shown in FIG. 7B, the intermediate is reacted under basic conditions using tris(tetra-n-butylammonium) with $X^4$-$Z^1$-PO(OH)—$Z^2$-PO(OH)$_2$ where $Z^1$ is —O—, $Z^2$ is —CH$_2$-, and $X^4$ is H. The basic conditions remove the tosylate protecting group and allow the modified phosphonate -$Z^1$-PO(OH)-$Z^2$-PO(OH)$_2$ to form a single bond to the C1 site. Upon treatment with acidic conditions and $CH_3CN$, the —O—PO(OH)—CH$_2$-PO(OH)$_2$ group is installed at the C1 site. As shown in FIG. 7C, the intermediate is reacted under basic conditions with $X^4$-$Z^1$-PO(O-protecting group)$_2$ where $Z^1$ is —OCH$_2$CH$_2$— and $X^4$ is H. The basic conditions remove the tosylate protecting group and allow the modified phosphate -$Z^1$-PO(O-protecting group)$_2$ to form a single bond to the C1 site. The protecting groups are removed following treatment with TMSBr in collidine and water wash, affording a —OCH$_2$CH$_2$-PO(OH)$_2$ group at the C1 site.

Figure 11:
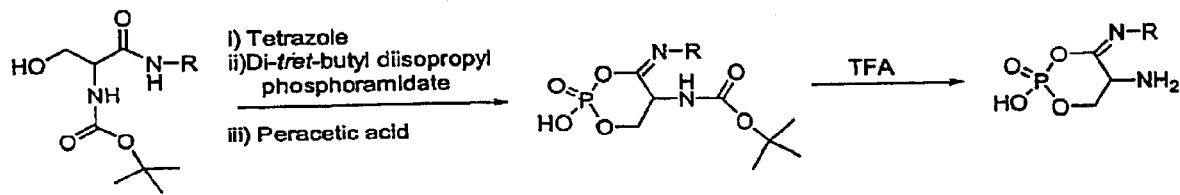
FIG. 11 illustrates a synthesis scheme for preparation of conformationally restrained, cyclic phosphate compounds.

To prepare the conformationally restricted cyclic-phosphate compound of formula (III), compounds 26–30 were used as starting materials in the synthesis scheme illustrated in FIG. 11. Compounds 26–30 were reacted with 1H-tetrazole and the resulting product was treated with di-tert-butyl diisopropylphosphoramidate, causing an intramolecular cyclization. In situ oxidation of the phosphonate with peracetic acid yielded a cyclic phosphate intermediate. Reduction with TFA yielded the compounds of formula (III).

Other conformationally restricted compounds can also be prepared.

Figure 12:
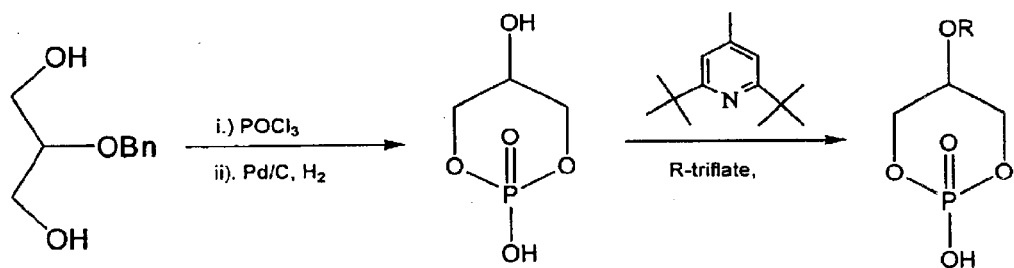
FIG. 12 illustrates a synthesis scheme for preparation of conformationally restrained, cyclic phosphate compounds.

As shown in FIG. 12, an alternative scheme is shown for preparing cyclic phosphates where $X^1$ and $X^2$ together are —O—PO(OH)—O—. A benzyl-protected 1,3 diol intermediate is reacted with $POCl_3$, which results in an intramolecular cyclization. Treatment with 10% palladium on activated carbon (Pd/C) under $H_2$ atmosphere (as described above) affords a cyclic phosphate bearing a hydroxyl group bound to the C2 carbon. The cyclic intermediate is then treated with an excess of R-triflate and 2,6-di-tert-butyl-4-methylpyridine to afford the final compound.

As shown in FIG. 13, a scheme is shown for preparing a cyclic phosphate where $X^1$ and $X^3$ together are —O—PO(OH)—NH—. Using the intermediates 35–43 prepared above as starting material, they are treated with tris(1,2,4,-triazole)phosphate followed by 2% HCl wash, resulting in intramolecular cyclization.

As shown in FIG. 14, a scheme is shown for preparing a cyclic compound where the phosphate group is not a part of the ring; specifically, $X^2$ and $X^3$ together are —N(H)—C(O)—N($R^1$)—. Using the intermediates 50–54 prepared above as starting materials, they are treated with anhydrous $COCl_2$, which inserts a carbonyl between between the amines bound to the C2 and C3 carbons during cyclization. Benzyl protecting groups are removed from the phosphate using 10% palladium on activated carbon (Pd/C) under $H_2$ atmosphere (as described above).

Figure 8:
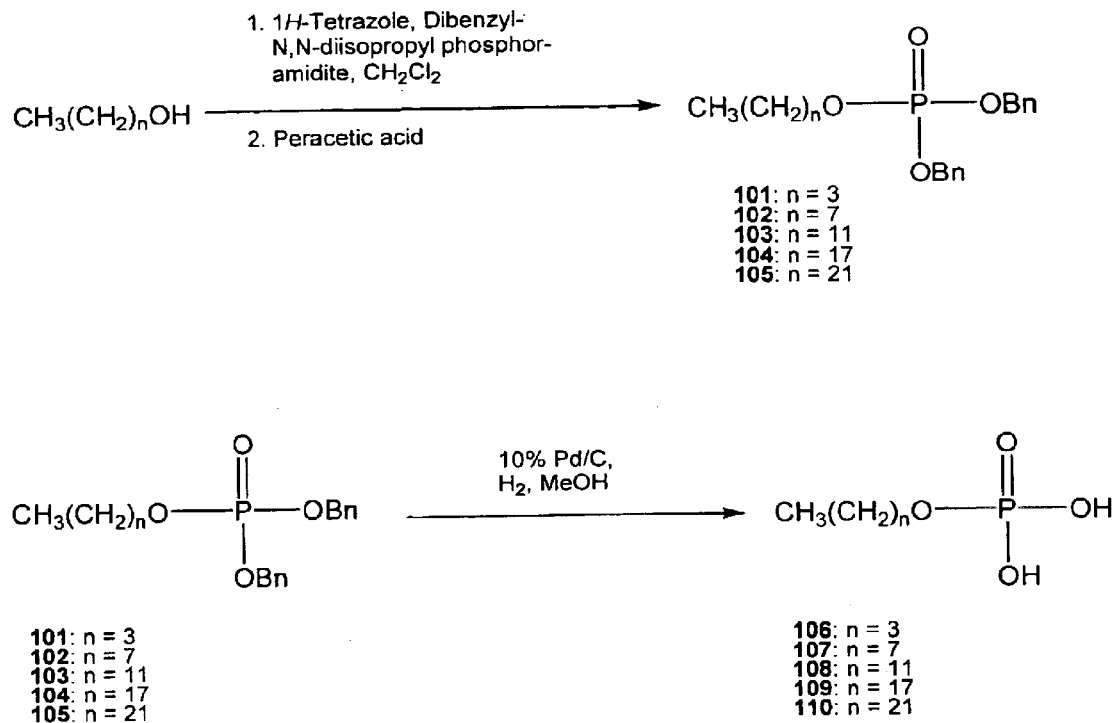
FIG. 8 illustrates the synthesis scheme employed for preparation of straight-chain fatty acid phosphate compounds 106–110.

Another class of compounds which can be used as agonists or antagonists of the LPA receptors are fatty acid phosphates or straight-chain phosphates. As shown in FIG. 8, anhydrous n-alkanol and 1H-tetrazole can be dissolved in anhydrous methylene chloride. A solution of dibenzyl-N,N-diisopropyl phosphoramidite in anhydrous methylene chloride can be added. Subsequently, peracetic acid in anhydrous methylene chloride can be added dropwise to afford the benzyl-protected fatty acid phosphates 101–105. The benzyl-protecting groups are removed following treatment in anhydrous methanol with 10% palladium on activated carbon (Pd/C) under $H_2$ atmosphere (as described above), affording the fatty acid phosphates 106–110.

Figure 9:
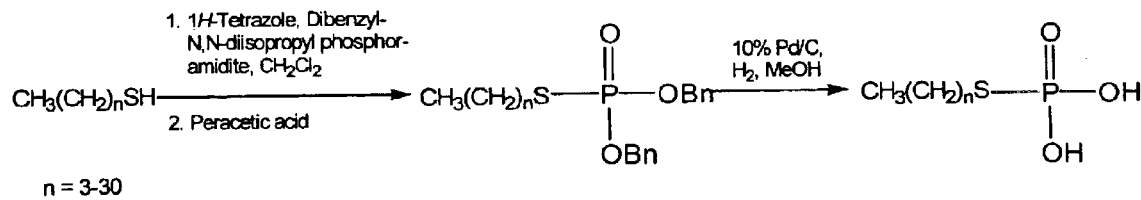
FIG. 9 illustrates synthesis of straight-chain thiophosphoric acid monoalkyl esters.
Figure 10:
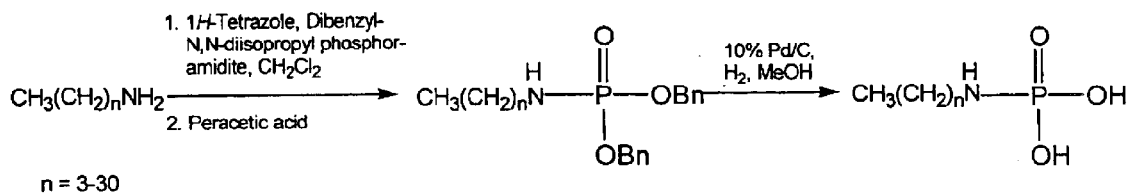
FIG. 10 illustrates synthesis of straight-chain alkylamidophosphoric acid.

As an alternative to preparing fatty acid phosphates, thiophosphates and amidophosphates can also be prepared. As shown in FIG. 9, for example, n-mercaptoalkanes and 1H-tetrazole can be dissolved in anhydrous methylene chloride. A solution of dibenzyl-N,N-diisopropyl phosphoramidite in anhydrous methylene chloride can be added. Subsequently, peracetic acid in anhydrous methylene chloride can be added dropwise to afford the benzyl-protected fatty acid thiophosphates. The benzyl-protecting groups are removed following treatment in anhydrous methanol with 10% palladium on activated carbon (Pd/C) under $H_2$ atmosphere (as described above), affording the fatty acid thiophosphates. As shown in FIG. 10, for example, n-alkylamine and 1H-tetrazole can be dissolved in anhydrous methylene chloride. A solution of dibenzyl-N,N-diisopropyl phosphoramidite in anhydrous methylene chloride can be added. Subsequently, peracetic acid in anhydrous methylene chloride can be added dropwise to afford the benzyl-protected fatty acid amidophosphates. The benzyl-protecting groups are removed following treatment in anhydrous methanol with 10% palladium on activated carbon (Pd/C) under $H_2$ atmosphere (as described above), affording the fatty acid amidophosphates.

Each of the above-identified reaction schemes can be further modified by attacking a primary amine group as shown in FIGS. 17–20. The intermediate is prepared, e.g., from compounds 50–54 which were treated with TFA to remove the t-Boc protecting group, affording the primary amine at the C2 site while leaving the phosphate protected.

Figure 17:
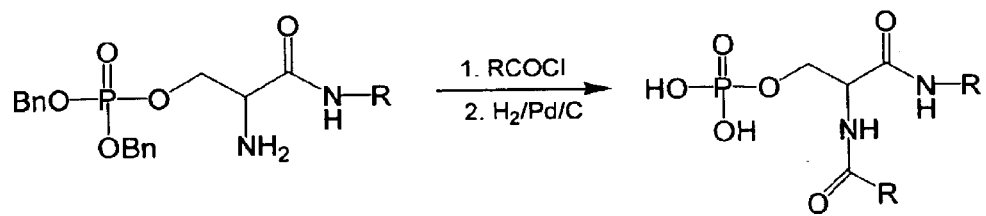
FIG. 17 illustrates a synthesis scheme for preparing compounds having an —N(H)-acyl group as $X^3$.

In FIG. 17, the intermediate compound possessing a primery amine at the C2 position is attacked with an acid halide (e.g., $R^1COCl$), which converts the primary amine into an amide (—N(H)—C(O)—$R^1$). The benzyl-protected phosphate can then be de-protected using treatment with 10% palladium on activated carbon (Pd/C) under $H_2$ atmosphere (as described above).

Figure 18:
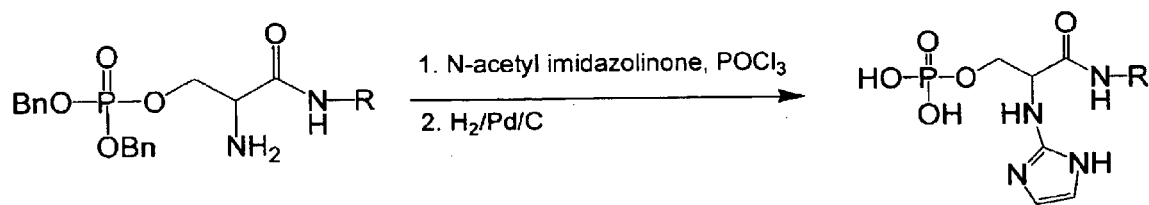
FIG. 18 illustrates a synthesis scheme for preparing compounds having an —N(H)-imidazole group as $X^3$.

In FIG. 18, the intermediate compound possessing a primery amine at the C2 position is attacked with N-acetyl imidazoline in $POCl_3$, which converts the primary amine into a secondary amine (—N(H)-imidazole). Substituted imidazolines can also be used. The benzyl-protected phosphate can then be de-protected using treatment with 10% palladium on activated carbon (Pd/C) under $H_2$ atmosphere (as described above).

Figure 19:
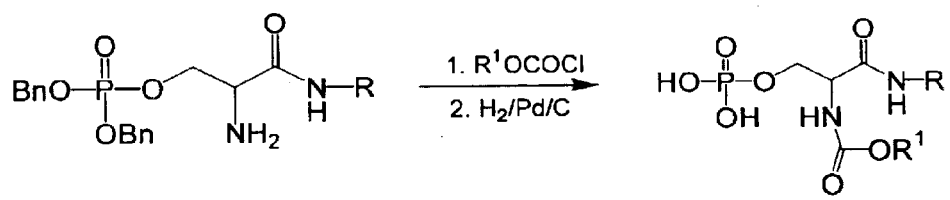
FIG. 19 illustrates a synthesis scheme for preparing compounds having an —N(H)—C(O)—O—$R^7$ as $X^3$.

In FIG. 19, the intermediate compound possessing a primery amine at the C2 position is attacked with $R^1OC(O)Cl$, which converts the primary amine into an carbamate (—N(H)—C(O)—O—$R^1$). The benzyl-protected phosphate can then be de-protected using treatment with 10% palladium on activated carbon (Pd/C) under $H_2$ atmosphere (as described above).

Figure 20:
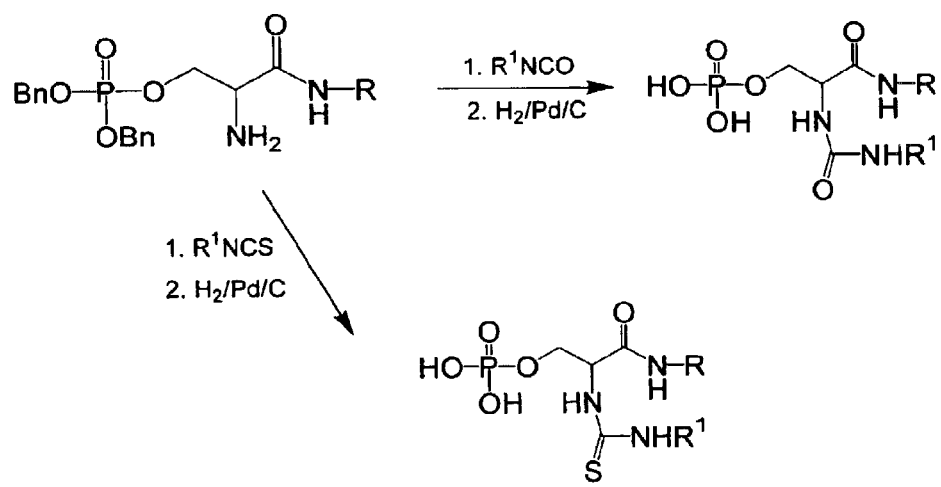
FIG. 20 illustrates a synthesis scheme for preparing compounds having an —N(H)—C(S)—O—$R^7$ as $X^3$.

In FIG. 20, the intermediate compound possessing a primery amine at the C2 position is attacked with $R^1NCO$ or $R^1NCS$, which converts the primary amine into either a uramide (—N(H)—C(O)—N(H)—$R^1$) or thiouramide (—N(H)—C(S)—N(H)—$R^1$). The benzyl-protected phosphate can then be de-protected using treatment with 10% palladium on activated carbon (Pd/C) under $H_2$ atmosphere (as described above).

Thus, the non-cyclic compounds of the present invention can be prepared by reacting $(Y^2O)_2PO$-$Z^{11}$-$Z^{13}$ or $(Y^2O)_2PO$-$Z^{12}P(OH)O$-$Z^{11}$-$Z^{13}$, where $Z^{11}$ is —$(CH_2)_m$— or —$O(CH_2)_m$— with m being an integer from 1 to 50, —$C(R^3)H$-, or —O—, $Z^{12}$ is —$(CH_2)_n$— or —$O(CH_2)_n$— with n being an integer from 1 to 50 or —O—, $Z^{13}$ is H or a first leaving group or -$Z^{11}$-$Z^{13}$ together form the first leaving group, and $Y^2$ is H or a protecting group; with an intermediate compound according to formula (VI), followed by a de-protection step, if necessary, both performed under conditions effective to afford a compound according to formula (I) where one or two of $X^1$, $X^2$, and $X^3$ is $(HO)_2PO$-$Z^1$- or $(HO)_2PO$-$Z^2$-$P(OH)O$-$Z^1$- where $Z^1$ and $Z^2$ being defined as above.

The intermediate compound of formula (VI) has the following structure:

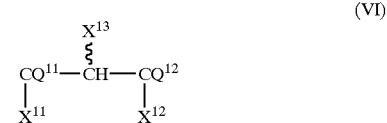

(VI)

wherein,
at least one of $X^{11}$, $X^{12}$, and $X^{13}$ is $R^{11}$—$Y^{11}$-A- with each being the same or different when two of $X^{11}$, $X^{12}$, and $X^{13}$ are $R^{11}$—$Y^{11}$-A-, or $X^{12}$ and $X^{13}$ are linked together as —N(H)—C(O)—N($R^{11}$)—;

at least one of $X^{11}$, $X^{12}$, and $X^{13}$ is OH, $NH_2$, SH, or a second leaving group;

optionally, one of $X^{11}$, $X^{12}$, and $X^{13}$ is H;

A is either a direct link, $(CH_2)_k$ with k being an integer from 0 to 30, or O;

$Y^{11}$ is —$(CH_2)_l$— with l being an integer from 1 to 30, —O—,

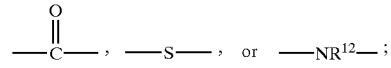

$Q^1$ and $Q^2$ are independently $H_2$, =$NR^{13}$, =O, a combination of H and —$NR^{14}R^{15}$;

$R^{11}$, for each of $X^{11}$, $X^{12}$, or $X^{13}$, is independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or an aromatic or heteroaromatic ring, an arylalkyl including straight or branched-chain C1 to C30 alkyl, an aryloxyalkyl including straight or branched-chain C1 to C30 alkyl,

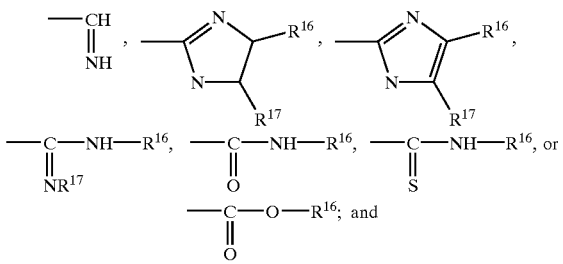

$R^{12}$, $R^{13}$, $R^{14}$, $R^{15}$, $R^{16}$, and $R^{17}$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl.

Having prepared the LPA receptor agonists and antagonists of the present invention, such compounds can be used to prepare pharmaceutical compositions suitable for treatment of patients as described hereinafter. Therefore, a further aspect of the present invention relates to a pharmaceutical composition that includes a pharmaceutically-acceptable carrier and a compound of the present invention. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 20 to 75 percent of active compound(s), together with the carrier, excipient, stabilizer, etc.

The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The compounds of the present invention may also be administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art. Typical dosages comprise about 0.01 to about 100 mg/kg·body wt. The preferred dosages comprise about 0.1 to about 100 mg/kg·body wt. The most preferred dosages comprise about 1 to about 100 mg/kg·body wt. Treatment regimen for the administration of the compounds of the present invention can also be determined readily by those with ordinary skill in art.

Certain compounds of the present invention have been found to be useful as agonists of LPA receptors while other compounds of the present invention have been found useful as antagonists of LPA receptors. Due to their differences in activity, the various compounds find different uses. The preferred animal subject of the present invention is a mammal, i.e., an individual belonging to the class Mammalia. The invention is particularly useful in the treatment of human subjects.

One aspect of the present invention relates to a method of modulating LPA receptor activity which includes providing a compound of the present invention which has activity as either an LPA receptor agonist or an LPA receptor antagonist and contacting an LPA receptor with the compound under conditions effective to modulate the activity of the LPA receptor.

The LPA receptor is present on a cell which either normally expresses the LPA receptor or has otherwise been transformed to express a particular LPA receptor. Suitable LPA receptors include, without limitation, EDG-2, EDG-4, EDG-7, and PSP-24 receptors. The tissues which contain cells that normally express these receptors are indicated in Table 1 above. When contacting a cell with the LPA receptor agonist or LPA receptor antagonist of the present invention, the contacting can be carried out while the cell resides in vitro or in vivo.

To heterologously express these receptors in host cells which do not normally express them, a nucleic acid molecule encoding one or more of such receptors can be inserted in sense orientation into an expression vector which includes appropriate transcription and translations regulatory regions (i.e., promoter and transcription termination signals) and then host cells can be transformed with the expression vector. The expression vector may integrate in the cellular genome or simply be present as extrachromosomal nuclear material. Expression can be either constitutive or inducible, although constitutive expression is suitable for most purposes.

The nucleotide and amino acid sequences for EDG-2 is known and reported in An et al. (1997b) and Genbank Accession No. U80811, which is hereby incorporated by reference. An EDG-2 encoding nucleic acid molecule has a nucleotide sequence according to SEQ. ID. No. 1 as follows:

```
atggctgcca tctctacttc catccctgta atttcacagc cccagttcac agccatgaat    60
gaaccacagt gcttctacaa cgagtccatt gccttctttt ataaccgaag tggaaagcat   120
cttgccacag aatggaacac agtcagcaag ctggtgatgg gacttggaat cactgtttgt   180
atcttcatca tgttggccaa cctattggtc atggtggcaa tctatgtcaa ccgccgcttc   240
cattttccta tttattacct aatggctaat ctggctgctg cagacttctt tgctgggttg   300
gcctacttct atctcatgtt caacacagga cccaatactc ggagactgac tgttagcaca   360
tggctcctgc gtcagggcct cattgacacc agcctgacgg catctgtggc caacttactg   420
gctattgcaa tcgagaggca cattacggtt ttccgcatgc agctccacac acggatgagc   480
aaccggcggg tagtggtggt cattgtggtc atctggacta tggccatcgt tatgggtgct   540
atacccagtg tgggctggaa ctgtatctgt gatattgaaa attgttccaa catggcaccc   600
ctctacagtg actcttactt agtcttctgg gccatttca acttggtgac ctttgtggta   660
atggtggttc tctatgctca catctttggc tatgttcgcc agaggactat gagaatgtct   720
cggcatagtt ctggaccccg gcggaatcgg ataccatga tgagtcttct gaagactgtg    780
gtcattgtgc ttggggcctt tatcatctgc tggactcctg gattggtttt gttacttcta   840
gacgtgtgct gtccacagtg cgacgtgctg gcctatgaga aattcttcct tctccttgct   900
gaattcaact ctgccatgaa ccccatcatt tactcctacc gcgacaaaga aatgagcgcc   960
acctttaggc agatcctctg ctgccagcgc agtgagaacc ccaccggccc cacagaaagc  1020
tcagaccgct cggcttcctc cctcaaccac accatcttgg ctggagttca cagcaatgca  1080
cactctgtgg tttag                                                    1095
```

The encoded EDG-2 receptor has an amino acid sequence according to SEQ. ID. No. 2 as follows:

```
MAAISTSIPV ISQPQFTAMN EPQCFYNESI AFFYNRSGKH LATEWNTVSK LVMGLGITVC    60
IFIMLANLLV MVAIYVNRRF HFPIYYLMAN LAAADFFAGL AYFYLMFNTG PNTRRLTVST   120
WLLRQGLIDT SLTASVANLL AIAIERHITV FRMQLHTRMS NRRVVVVIVV IWTMAIVMGA   180
IPSVGWNCIC DIENCSNMAP LYSDSYLVFW AIFNLVTFVV MVVLYAHIFG YVRQRTMRMS   240
RHSSGPRRNR DTMMSLLKTV VIVLGAFIIC WTPGLVLLLL DVCCPQCDVL AYEKFFLLLA   300
EFNSAMNPII YSYRDKEMSA TFRQILCCQR SENPTGPTES SDRSASSLNH TILAGVHSND   360
HSVV                                                                364
```

The nucleotide and amino acid sequences for EDG-4 is known and reported in An et al. (1998b) and Genbank Accession No. NM_004720, which is hereby incorporated by reference. An EDG-4 encoding nucleic acid molecule has a nucleotide sequence according to SEQ. ID. No. 3 as follows:

```
atggtcatca tgggccagtg ctactacaac gagaccatcg gcttcttcta taacaacagt    60
ggcaaagagc tcagctccca ctggcggccc aaggatgtgg tcgtggtggc actggggctg   120
accgtcagcg tgctggtgct gctgaccaat ctgctggtca tagcagccat cgcctccaac   180
```

-continued

```
cgccgcttcc accagcccat ctactacatg ctcggcaatc tggccgcggc tgacctcttc    240
gcgggcgtgg cctacctctt cctcatgttc cacactggtc cccgcacagc ccgactttca    300
cttgagggct ggttcctgcg gcagggcttg ctggacacaa gcctcactgc gtcggtggcc    360
acactgctgg ccatcgccgt ggagcggcac cgcagtgtga tggccgtgca gctgcacagc    420
cgcctgcccc gtggccgcgt ggtcatgctc attgtgggcg tgtgggtggc tgccctgggc    480
ctggggctgc tgcctgccca ctcctggcac tgcctctgtg ccctggaccg ctgctcacgc    540
atggcacccc tgctcagccg ctcctatttg gccgtctggg ctctgtcgag cctgcttgtc    600
ttcctgctca tggtggctgt gtacacccgc attttcttct acgtgcggcg gcgagtgcag    660
cgcatggcag agcatgtcag ctgccacccc cgctaccgag agaccacgct cagcctggtc    720
aagactgttg tcatcatcct gggggcgttc gtggtctgct ggacaccagg ccaggtggta    780
ctgctcctgg atggtttagg ctgtgagtcc tgcaatgtcc tggctgtaga aaagtacttc    840
ctactgttgg ccgaggccaa ctcactggtc aatgctgctg tgtactcttg ccgagatgct    900
gagatgcgcc gcaccttccg ccgccttctc tgctgcgcgt gcctccgcca gtccacccgc    960
gagtctgtcc actatacatc ctctgcccag ggaggtgcca gcactcgcat catgcttccc   1020
gagaacggcc acccactgat ggactccacc ctttag                             1056
```

The encoded EDG-4 receptor has an amino acid sequence according to SEQ. ID. No. 4 as follows:

```
MVIMGQCYYN ETIGFFYNNS GKELSSHWRP KDVVVVALGL TVSVLVLLTN LLVIAAIASN    60
RRFHQPIYYL LGNLAAADLF AGVAYLFLMF HTGPRTARLS LEGWFLRQGL LDTSLTASVA   120
TLLAIAVERH RSVMAVQLHS RLPRGRVVML IVGVWVAALG LGLLPAHSWH CLCALDRCSR   180
MAPLLSRSYL AVWALSSLLV FLLMVAVYTR IFFYVRRRVQ RMAEHVSCHP RYRETTLSLV   240
KTVVIILGAF VVCWTPGQVV LLLDGLGCES CNVLAVEKYF LLLAEANSLV NAAVYSCRDA   300
EMRRTFRRLL CCACLRQSTR ESVHYTSSAQ GGASTRIMLP ENGHPLMDST L            351
```

The nucleotide and amino acid sequences for EDG-7 is known and reported in Bandoh et al. (1999) and Genbank Accession No. NM_012152, which is hereby incorporated by reference. An EDG-7 encoding nucleic acid molecule has a nucleotide sequence according to SEQ. ID. No. 5 as follows:

```
atgaatgagt gtcactatga caagcacatg gactttttt ataataggag caacactgat     60
actgtcgatg actggacagg aacaaagctt gtgattgttt tgtgtgttgg gacgttttc    120
tgcctgttta tttttttttc taattctctg gtcatcgcgg cagtgatcaa aaacagaaaa    180
tttcatttcc ccttctacta cctgttggct aatttagctg ctgccgattt cttcgctgga    240
attgcctatg tattcctgat gtttaacaca ggcccagttt caaaaacttt gactgtcaac    300
cgctggtttc tccgtcaggg gcttctggac agtagcttga ctgcttccct caccaacttg    360
ctggttatcg ccgtggagag gcacatgtca atcatgagga tgcgggtcca tagcaacctg    420
accaaaaaga gggtgacact gctcattttg cttgtctggg ccatcgccat ttttatgggg   480
gcggtcccca cactgggctg gaattgcctc tgcaacatct ctgcctgctc ttccctggcc    540
cccatttaca gcaggagtta ccttgttttc tggacagtgt ccaacctcat ggccttcctc    600
```

-continued

```
atcatggttg tggtgtacct gcggatctac gtgtacgtca agaggaaaac caacgtcttg    660
tctccgcata caagtgggtc catcagccgc cggaggacac ccatgaagct aatgaagacg    720
gtgatgactg tcttaggggc gtttgtggta tgctggaccc cgggcctggt ggttctgctc    780
ctcgacggcc tgaactgcag gcagtgtggc gtgcagcatg tgaaaggtg gttcctgctc    840 ctggcgctgc tcaactccgt cgtgaacccc atcatctact cctacaagga cgaggacatg    900
tatggcacca tgaagaagat gatctgctgc ttctctcagg agaacccaga gaggcgtccc    960
tctcgcatcc cctccacagt cctcagcagg agtgacacag gcagccagta catagaggat   1020
agtattagcc aaggtgcagt ctgcaataaa agcacttcct aa                      1062
```

The encoded EDG-7 receptor has an amino acid sequence according to SEQ. ID. No. 6 as follows:

```
MNECHYDKHM DFFYNRSNTD TVDDWTGTKL VIVLCVGTFF CLFIFFSNSL VIAAVIKNRK     60

FHFPFYYLLA NLAAADFFAG IAYVFLMFNT GPVSKTLTVN RWFLRQGLLD SSLTASLTNL    120

LVIAVERHNS IMRMRVHSNL TKKPVTLLIL LVWAIAIFMG AVPTLGWNCL CNISACSSLA    180

PIYSRSYLVF WTVSNLMAFL IMVVVYLRIY VYVKRKTNVL SPHTSGSISR RRTPMKLMKT    240

VMTVLGAFVV CWTPGLVVLL LDGLNCRQCG VQHVKRWFLL LALLNSVVNP IIYSTKDEDM    300

YGTMKKMICC FSQENPERRP SRIPSTVLSR SDTGSQYIED SISQGAVCNK STS           353
```

The nucleotide and amino acid sequences for PSP-24 is known and reported in Kawasawa et al. (2000) and Genbank Accession No. AB030566, which is hereby incorporated by reference. A PSP-24 encoding nucleic acid molecule has a nucleotide sequence according to SEQ. ID. No. 7 as follows:

```
atggtcttct cggcagtgtt gactgcgttc cataccggga catccaacac aacatttgtc     60
gtgtatgaaa acacctacat gaatattaca ctccctccac cattccagca tcctgacctc    120
agtccattgc ttagatatag ttttgaaacc atggctccca ctggtttgag ttccttgacc    180
gtgaatagta cagctgtgcc cacaacacca gcagcattta agagcctaaa cttgcctctt    240
cagatcaccc tttctgctat aatgatattc attctgtttg tgtcttttct tgggaacttg    300
gttgtttgcc tcatggttta ccaaaaagct gccatgaggt ctgcaattaa catcctcctt    360
gccagcctag cttttgcaga catgttgctt gcagtgctga acatgccctt gccctggta    420 actattctta ctacccgatg gattttgg aaattcttct gtagggtatc tgctatgttt    480
ttctggttat ttgtgataga aggagtagcc atcctgctca tcattagcat agataggttc    540
cttattatag tccagaggca ggataagcta aacccatata gagctaaggt tctgattgca    600
gtttcttggg caacttcctt ttgtgtagct tttcctttag ccgtaggaaa ccccgacctg    660
cagatacctt cccgagctcc ccagtgtgtg tttgggtaca caaccaatcc aggctaccag    720
gcttatgtga ttttgatttc tctcatttct ttcttcatac ccttcctggt aatactgtac    780
tcatttatgg gcatactcaa caccctttcgg cacaatgcct tgaggatcca tagctaccct    840
gaaggtatat gcctcagcca ggccagcaaa ctgggtctca tgagtctgca gagacctttc    900
cagatgagca ttgacatggg ctttaaaaca cgtgccttca ccactatttt gattctcttt    960
gctgtcttca ttgtctgctg ggccccattc accacttaca gccttgtggc aacattcagt   1020
aagcactttt actatcagca caactttttt gagattagca cctggctact gtggctctgc   1080
```

```
                            -continued
tacctcaagt ctgcattgaa tccgctgatc tactactgga ggattaagaa attccatgat   1140
gcttgcctgg acatgatgcc taagtccttc aagtttttgc cgcagctccc tggtcacaca   1200
aagcgacgga tacgtcctag tgctgtctat gtgtgtgggg aacatcggac ggtggtgtga   1260
```

The encoded PSP-24 receptor has an amino acid sequence according to SEQ. ID. No. 8 as follows:

```
MVFSAVLTAF HTGTSNTTFV VYENTYMNIT LPPPFQHPDL SPLLRYSFET MAPTGLSSLT    60

VNSTAVPTTP AAFKSLNLPL QITLSAIMIF ILFVSFLGNL VVCLMVYQKA AMRSAINILL   120

ASLAFADMLL AVLNMPFALV TILTTRWIPG KFFCRVSAMF FWLPVIEGVA ILLIISTDRF   180

LIIVQRQDKL NPYRAKVLIA VSWATSFCVA FPLAVGNPDL QIPSRAPQCV FGYTTNPGYQ   240

AYVILISLIS FFIPFLVILY SFMGILNTLR HNALRIHSYP EGICLSQASK LGLMSLQRPF   300

QMSIDMGFKT RAFTTILILF AVFIVCWAPF TTYSLVATFS KHFYYQHUFF EISTWLLWLC   360

YLKSALNPLI YYWRIKKFHD ACLDMMPKSF KFLPQLPGHT KRRIRPSAVY VCGEHRTVV    419
```

LPA receptor agonists will characteristically induce LPA-like activity from an LPA receptor, which can be measured either chemically, e.g., $Ca^{2+}$ or $Cl^-$ current in oocytes, or by examining changes in cell morphology, mobility, proliferation, etc. In contrast, LPA receptor antagonists will characteristically block LPA-like activity from an LPA receptor. This too can be measured either chemically, e.g., $Ca^{2+}$ or $Cl^-$ current in oocytes, or by examining changes in cell morphology, mobility, proliferation, etc.

By virtue of the compounds of the present invention acting as LPA receptor antagonists, the present invention also relates to a method of inhibiting LPA-induced activity on an LPA receptor. This method includes providing a compound of the present invention which has activity as an LPA receptor antagonist and contacting an LPA receptor with the compound under conditions effective to inhibit LPA-induced activity of the LPA receptor. The LPA receptor can be as defined above. The LPA receptor is present on a cell which normally expresses the receptor or which heterologously expresses the receptor. The contacting of the LPA receptor with the compound of the present invention can be performed either in vitro or in vivo.

As noted above, LPA is a signaling molecule involved in a number of different cellular pathways which involve signaling through LPA receptors, including those LPA receptors described above. Therefore, it is expected that the compounds of the present invention will modulate the effects of LPA on cellular behavior, either by acting as LPA receptor antagonists or LPA receptor agonists.

One aspect of the present invention relates to a method of treating cancer which includes providing a compound of the present invention and administering an effective amount of the compound to a patient in a manner effective to treat cancer. The types of cancer which can be treated with the compounds of the present invention includes those cancers characterized by cancer cells whose behavior is attributable at least in part to LPA-mediated activity. Typically, these types of cancer are characterized by cancer cells which express one or more types of LPA receptors. Exemplary forms of cancer include, without limitation, prostate cancer and ovarian cancer.

The compounds of the present invention which are particularly useful for cancer treatment are the LPA receptor antagonists.

When administering the compounds of the present invention, they can be administered systemically or, alternatively, they can be administered directly to a specific site where cancer cells are present. Thus, administering can be accomplished in any manner effective for delivering the compound to cancer cells. Without being bound by theory, it is believed that the LPA receptor antagonists, upon binding to LPA receptors, will inhibit proliferation or metastasis of the cancer cells or otherwise destroy those cancer cells. As shown in Example 12 infra, several LPA antagonist compounds of the present invention were cytotoxic to prostate cancer cell lines which express one or more LPA receptors of the type described above.

When the LPA antagonist compounds or pharmaceutical compositions of the present invention are administered to treat cancer, the pharmaceutical composition can also contain, or can be administered in conjunction with, other therapeutic agents or treatment regimen presently known or hereafter developed for the treatment of various types of cancer.

Cancer invasion is a complex multistep process in which individual cells or cell clusters detach from the primary tumor and reach the systemic circulation or the lymphatics to spread to different organs (Liotta et al., 1987). During this process, tumor cells must arrest in capillaries, extravasate, and migrate into the stroma of the tissue to make secondary foci. First, tumor cells must recognize signals on the endothelial cell that arrest them from the circulation. Second, tumor cells must attach to the basement membrane glycoprotein laminin via the cell surface laminin receptors. Following attachment to the basement membrane, tumor cells secrete proteases to degrade the basement membrane. Following attachment and local proteolysis, the third step of invasion is tumor cell migration. Cell motility plays a central role in tumor cell invasion and metastasis. The relationship between motility of tumor cells in vitro and the metastatic behavior in animal experiments indicates a strong direct correlation (Hoffman-Wellenhof et al., 1995). It is a well-documented fact that PLGFs promote proliferation and increase invasiveness of cancer cell in vitro. Imamura and colleagues established that cancer cells require serum factors for their invasion (Imamura et al., 1991), and later identified LPA as the most important serum component that is fully capable of restoring tumor cell invasion in serum-free systems (Xu et al., 1995a; Imamura et al., 1993; Mukai et al., 1993).

It has been shown that PLGFR are expressed in ovarian cancer cell lines; namely, OCC1 and HEY cells. Specifically, RT-PCR analyses show the presence of EDG-2 and EDG-7 receptors in these cell lines. Recently, Im et al. (2000) demonstrated that EDG-7 is expressed in prostate cancer cell lines; namely, PC-3 and LNCaP cells. RT-PCR analysis on the prostate cancer cell lines DU-145, PC-3, and LNCaP lines showed that EDG-2, 4, 5, and EDG-7 are present in all three prostate cancer cell lines, whereas EDG-3 is present in LNCaP and DU-145 prostate cancer cell lines.

As shown in the Examples, several LPA receptor antagonists of the present invention are capable of targeting specific prostate cancer cell lines and specific ovarian cancer cell lines. Thus, the LPA antagonists of the present invention provide an alternative approach for treatment of LPA-mediated cancers, including prostate cancer and ovarian cancer.

Another aspect of the present invention relates to a method of enhancing cell proliferation. This method of enhancing cell proliferation includes the steps of providing a compound of the present invention which has activity as an agonist of an LPA receptor and contacting the LPA receptor on a cell with the compound in a manner effective to enhance LPA receptor-induced proliferation of the cell.

In addition to the roles that LPA plays in modulating cancer cell activity, there is strong evidence to suggest that LPA also has a physiological role in natural wound healing. At wound sites, LPA derived from activated platelets is believed to be responsible, at least in part, for stimulating cell proliferation at the site of injury and inflammation possibly in synchronization with other platelet-derived factors (Balazs et al., 2000). Moreover, LPA by itself stimulates platelet aggregation, which may in turn be the factor that initiates an element of positive feedback to the initial aggregatory response (Schumacher et al., 1979; Tokumura et al., 1981; Gerrard et al., 1979; Simon et al., 1982).

Due to the role of LPA in cell proliferation, compounds having LPA receptor agonist activity can be used in a manner effective to promote wound healing. Accordingly, another aspect of the present invention relates to a method of treating a wound. This method is carried out by providing a compound of the present invention which has activity as an agonist of an LPA receptor and delivering an effective amount of the compound to a wound site, where the compound binds to LPA receptors on cells that promote healing of the wound, thereby stimulating LPA receptor agonist-induced cell proliferation to promote wound healing.

The primary goal in the treatment of wounds is to achieve wound closure. Open cutaneous wounds represent one major category of wounds and include burn wounds, neuropathic ulcers, pressure sores, venous stasis ulcers, and diabetic ulcers. Open cutaneous wounds routinely heal by a process which comprises six major components: i) inflammation, ii) fibroblast proliferation, iii) blood vessel proliferation, iv) connective tissue synthesis v) epithelialization, and vi) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age (see Hunt and Goodson, 1988).

Phospholipids have been demonstrated to be important regulators of cell activity, including mitogenesis (Xu et al., 1995b), apoptosis, cell adhesion, and regulation of gene expression. Specifically, for example, LPA elicits growth factor-like effects on cell proliferation (Moolenaar, 1996) and cell migration (Imamura et al., 1993). It has also been suggested that LPA plays a role in wound healing and regeneration (Tigyi and Miledi, 1992).

In general, agents which promote a more rapid influx of fibroblasts, endothelial and epithelial cells into wounds should increase the rate at which wounds heal. Compounds of the present invention that are useful in treating wound healing can be identified and tested in a number of in vitro and in vivo models.

In vitro systems model different components of the wound healing process, for example the return of cells to a "wounded" confluent monolayer of tissue culture cells, such as fibroblasts (Verrier et al., 1986), endothelial cells (Miyata et al., 1990) or epithelial cells (Kartha et al., 1992). Other systems permit the measurement of endothelial cell migration and/or proliferation (Muller et al., 1987; Sato et al., 1988).

In vivo models for wound healing are also well-known in the art, including wounded pig epidermis (Ohkawara et al., 1977) or drug-induced oral mucosal lesions in the hamster cheek pouch (Cherrick et al., 1974).

The compounds of the present invention which are effective in wound healing can also be administered in combination, i.e., in the pharmaceutical composition of the present invention or simultaneously administered via different routes, with a medicament selected from the group consisting of an antibacterial agent, an antiviral agent, an antifungal agent, an antiparasitic agent, an antiinflammatory agent, an analgesic agent, an antipruritic agent, or a combination thereof.

For wound healing, a preferred mode of administration is by the topical route. However, alternatively, or concurrently, the agent may be administered by parenteral, subcutaneous, intravenous, intramuscular, intraperitoneal or transdermal routes. Alternatively, or concurrently, administration may be by the oral route. The dosage administered will be dependent upon the age, health, and weight of the recipient, kind of concurrent treatment, if any, frequency of treatment, and the nature of the effect desired.

For the preferred topical applications, especially for treatment of humans and animals having a wound, it is preferred to administer an effective amount of a compound according to the present invention to the wounded area, e.g., skin surfaces. This amount will generally range from about 0.001 mg to about 1 g per application, depending upon the area to be treated, the severity of the symptoms, and the nature of the topical vehicle employed. A preferred topical preparation is an ointment wherein about 0.01 to about 50 mg of active ingredient is used per ml of ointment base, such as PEG-1000.

EXAMPLES

The following examples are intended to illustrate, but by no means are intended to limit, the scope of the present invention as set forth in the appended claims.

Materials and Methods

A Thomas-Hoover capillary melting point (mp) apparatus was used to measure all melting points (mps), which were uncorrected.

$^1$H and $^{13}$C nuclear magnetic resonance (NMR) spectra were recorded on a Bruker AX 300 spectrometer (300, 75.5 MHz). Chemical shift values (δ) are expressed as parts per million (ppm) relative to tetramethylsilane (TMS). Peaks are abbreviated as follows: s—singlet; d—doublet; t—triplet; q—quartet; bs—broad singlet; m—multiplet.

Proton, carbon-13, and phosphorous-31 magnetic resonance spectra were obtained on a Bruker AX 300 spectrometer. Chemical shifts for proton and carbon-13 are reported as parts per million ( ) relative to tetramethylsilane (TMS). Spectra for phosphorous-31 are reported as parts per million ( ) relative to 0.0485 M triphenylphosphate in acetone-$d_6$ at =0 ppm.

Infrared (IR) spectra were recorded on Perkin Elmer System 200-FTIR.

Mass spectra (MS) were recorded on either a Bruker Esquire AG or a Bruker Esquire LC/MS spectrometer by direct infusion utilizing the Electrospray Interface (ESI) either in the positive or negative mode. Spectral data were consistent with assigned structures.

Elemental analysis was performed by Atlantic Microlabs, Inc. (Norcross, Ga.), and values found are within±0.4% of the theoretical values.

Silica gel (Merck, 230–400 mesh or 200–425 mesh, 60A°) was used for flash column chromatography.

Analytical TLC was performed on Sigma-Aldrich silica gel 60 F 254 TLC sheets with aluminum backings (thickness 200 or 250 microns).

All reagents, solvents, and chromatography media, unless otherwise noted, were purchased from either Aldrich Chemical Company (Milwaukee, Wis.), Fisher Scientific (Pittsburgh, Pa.), or Sigma Chemical Co. (St. Louis, Mo.) without further purification. Tetrahydrofuran (THF) was dried by distillation from sodium metal with benzophenone as an indicator. Anhydrous methylene chloride ($CH_2Cl_2$) was distilled from calcium hydride ($CaH_2$). All the mono glycerides were from Nu-Check-Prep (Minneapolis, Minn.). t-Boc-L-serine was purchased from Fluka.

All lipids were purchased from Avanti Polar Lipids (Alabaster, Ala.). Fatty acid-free bovine serum albumin (BSA). Prior to use, LPA was complexed, at a 1:1 ratio molar ratio, with 1 mM BSA dissolved in $Ca^{2+}$-free Hanks' balanced salt solution containing 1 mM EGTA. Aliquots of all the other lipids were dissolved in MeOH and mixed with LPA prior to application, or as otherwise indicated.

Cytofectene transfection reagent was from Bio-Rad (Hercules, Calif.). Fura-2 AM was from Molecular Probes (Eugene, Ore.).

Culture media, fetal bovine serum (FBS), and G418 were obtained from Cellgro (Herndon, Va.).

RH7777 cells, stably expressing human Edg-4, were kindly provided by Dr. Kevin Lynch (University of Virginia, Charlottesville, Va.). Flag-tagged cDNA's encoding human Edg-4 and -7 inserted into the pCDNA3 expression plasmid (Invitrogen, Carlsbad, Calif.), were a generous gift from Dr. Junken Aoki (University of Tokyo, Tokyo, Japan). RH7777 and NIH3T3 cells were obtained from the American Type Culture Collection (Manassas, Va.). HEY cells were provided by Dr. Lisa Jennings (University of Tennessee, Memphis). All cell lines were maintained in Dulbecco's Modified Eagle's Medium (DMEM) containing 10% FBS and 2 mM glutamine. Oocytes were obtained from adult *Xenopus laevis* frogs as previously described (Tigyi et al., 1999).

Stable Transfection

RH7777 cells were transfected with the cDNA constructs encoding human Edg-2, Edg-4, or Edg-7 and then were subcloned into the pCDNA3 expression vector using the Cytofectene transfection reagent according to the manufacturers' protocol. Transfected cells were selected in DMEM containing 10% FBS and 1 mg/ml geneticin. Resistant cells were collected and subcloned by limiting dilution. The resulting clones were then screened using functional assays and RT-PCR analysis. Data are representative of three individual clones.

Transient Transfection

RH7777 cells were plated on polylysine-coated glass coverslips (Bellco, Vineland, N.J.) one day prior to transfection. The following day, cells were transfected overnight (16–18 hr) with 1 µg of plasmid DNA mixed with 6 µl of Cytofectene. The cells were then rinsed twice with DMEM and cultured in DMEM containing 10% FBS. The next day, the cells were rinsed with DMEM and serum was withdrawn for a minimum of 2 hr prior to monitoring intracellular $Ca^{2+}$.

Measurement of Intracellular $Ca^{2+}$ and Data Analysis

Changes in intracellular $Ca^{2+}$ were monitored using the fluorescent $Ca^{2+}$ indicator Fura-2 AM as previously described (Tigyi et al., 1999). Data points from the intracellular $Ca^{2+}$ measurements represent the total peak area of the $Ca^{2+}$ transients elicited, as determined by the FLWinLab software (Perkin-Elmer, Wellesley, Mass.). Data points represent the average of at least 3 measurements±standard deviation. The significance of the data points was determined using the students t-test and values were considered significant at p<0.05.

Electrophysiological Recording in *Xenopus* Oocytes

Oscillatory Cl⁻ currents, elicited by LPA, were recorded using a two-electrode voltage clamp system as previously described (Tigyi et al., 1999).

RT-PCR Analysis of Edg and PSP24 mRNA

The identification of Edg and PSP24 receptor mRNA by RT-PCR was performed as previously described (Tigyi et al., 1999), using the following oligonucleotide sequences:

EDG-1
forward primer 5'-$_{81}$TCATCGTCCGGCATTACAACTA-3' (SEQ. ID No. 9);
reverse primer 5'-GAGTGAGCTTGTAGGTGGTG$_{351}$-3' (SEQ. ID No. 10);

EDG-2
forward primer 5'-$_{65}$AGATCTGACCAGCCGACTCAC-3' (SEQ. ID No. 11);
reverse primer 5'-GTTGGCCATCAAGTAATAAATA$_{422}$-3' (SEQ. ID No. 12);

EDG-3
forward primer 5'-$_{137}$CTTGGTCATCTGCAGCTTCATC-3' (SEQ. ID No. 13);
reverse primer 5'-TGCTGATGCAGAAGGCAATGTA$_{597}$-3' (SEQ. ID No. 14);

EDG-4
forward primer 5'-$_{634}$CTGCTCAGCCGCTCCTATTTG-3' (SEQ. ID No. 15);
reverse primer 5'-AGGAGCACCCACAAGTCATCAG$_{1185}$-3' (SEQ. ID No. 16);

EDG-5
forward primer 5'-$_{11}$ATGGGCAGCTTGTACTCGGAG-3' (SEQ. ID No. 17);
reverse primer 5'-CAGCCAGCAGACGATAAAGAC$_{720}$-3' (SEQ. ID No. 18);

EDG-6
forward primer 5'-$_{280}$TGAACATCACGCTGAGTGACCT-3' (SEQ. ID No. 19);
reverse primer 5'-GATCATCAGCACCGTCTTCAGC$_{790}$-3' (SEQ. ID No. 20);

EDG-7
forward primer 5'-$_{91}$AGCAACACTGATACTGTCGATG-3' (SEQ. ID No. 21);
reverse primer 5'-GCATCCTCATGATTGACATGTG$_{446}$-3' (SEQ. ID No. 22);

EDG-8
forward primer 5'-$_{88}$ATCTGTGCGCTCTATGCAAGGA-3' (SEQ. ID No.23);
reverse primer 5'-GGTGTAGATGATAGGATTCAGCA$_{1161}$-3' (SEQ. ID No. 24);

PSP24
forward primer 5'-$_{320}$CTGCATCATCGTGTACCAGAG-3' (SEQ. ID No.25); and
reverse primer 5'-ACGAACTCTATGCAGGCCTCGC$_{1184}$-3' (SEQ. ID No.26).

Cell Proliferation Assay

Proliferation of NIH3T3 cells was assessed by direct cell counting as previously described (Tigyi et al., 1999). NIH3T3 cells were plated in 24-well plates at a density of 10,000 cells/well, in DMEM containing 10% FBS. The following day, the cells were rinsed and serum starved in DMEM for 6 hr. Lipids were then added for 24 hr. Cell numbers were determined by counting in a Coulter counter (Coulter Electronics, Hialeah, Fla.).

Incorporation of $^3$H-thymidine

The incorporation of $^3$H-thymidine into RH7777 cells was determined as previously described (Tigyi et al., 1994).

Example 1

Synthesis of N-(tert-butoxycarbonyl)-L-serine β-lactone, Intermediate Compound 25

A 500 ml three-neck flask was equipped with a low temperature thermometer and a 100 ml dropping funnel. All glassware were flame-dried and cooled to room temperature under Argon (Ar) before use. To the flask were added triphenylphosphine (Ph$_3$P) (10 g, 38 mmol, dried over P$_2$O$_5$ under vacuum for 72 hrs) and freshly distilled THF (190 ml). The solution was cooled and stirred at −78° C. (dry ice-acetone bath) under argon. With vigorous stirring, freshly distilled diethyl azodicarboxylate (DEAD) (6.2 ml, 39.9 mmol) was added with a syringe over a period of 30 min. After the addition was complete, the mixture was stirred until a milky white paste was obtained (ca. 30–40 min). A solution of N-(tert-butoxycarbonyl)-L-serine (24) (7.79 g, 38 mmol, dried over P$_2$O$_5$ under vacuum for 72 hrs) in freshly distilled THF (75 ml) was added dropwise over a period of 45 min to the reaction mixture. The mixture was stirred overnight at −78° C. under argon and allowed to warm to 0° C. (the flask was placed in an ice bath when the temperature reached −10° C.). After 30 min (ca) the ice bath was replaced with a water bath, and the reaction mixture was stirred for 2 hrs and concentrated on the rotary evaporator to pale yellow oil at 30° C. The oil was then treated with 25% EtOAc/hexanes (100 ml), the resulting white solid was removed by filteration and washed with 25% EtOAc/hexanes (2×70 ml), the combined filtrate was concentrated, and the residual oil subjected to flash chromatography on silica gel with 25% (500 ml) and 30% (1500 ml) EtOAc/hexanes, successively.

Appropriate fractions were combined to afford 3.4 g (47%) of 25 as a white solid: mp 119–121° C. dec (Lit. 119.5–120.5° C. dec); $^1$H NMR (CD$_2$Cl$_2$) δ 1.44 (s, 9H), 4.38–4.42 (m, 2H), 4.96–5.03 (q, J$_1$=6.1 Hz, J$_2$=12.5 Hz, 1H), 5.39 (s, br, 1H); $^{13}$C NMR (CD$_2$Cl$_2$) d 28.31, 60.01, 66.63, 81.50, 155.01, 169.94; IR (KBr) 3361, 2978, 1843, 1680, 1533, 1370, 1292 cm$^{-1}$; Anal. Calcd. for C$_8$H$_{13}$NO$_4$: C, 51.33; H, 6.94; N, 7.50. Found: C, 51.41; H, 7.01; N, 7.51.

Example 2

Synthesis of Compounds 26–34

The glassware used were flame-dried and cooled to room temperature under argon atmosphere. The reaction was carried out in argon atmosphere. THF was freshly distilled prior to use.

Compound 26 tert-Butyl N-[1-(hydroxymethyl)-2-(nonylamino)-2-oxoethyl]carbamate

To a solution of decyl amine (490 mg, 3.20 mmol) in THF (60 ml), N-(tert-butoxycarbonyl)-L-serine β-lactone (300 mg, 1.60 mmol) was added, and the mixture was refluxed overnight under argon. The reaction mixture was concentrated on a rotary evaporator. The residue was subjected to flash column chromatography, eluting with EtOAc/hexanes of various compositions.

Appropriate fractions were pooled, and concentrated to dryness in vacuo to afford 290 mg (52%) of 26 as a white waxy powder: mp 50–52° C.; $^1$H NMR (CDCl$_3$) δ 0.88 (t, J=6.4 Hz, 3H), 1.26 (s, 14H), 1.46 (s, 9H), 3.04 (bs, 1H), 3.16–3.34 (m, 2H), 3.63 (m, 1H), 4.06–4.15 (m, 2H), 5.53 (bs, 1H), 6.63 (bs, 1H); $^{13}$C NMR (CDCl$_3$) δ 1409, 22.65, 26.80, 28.27, 29.24, 29.27, 29.37, 29.50, 29.51, 31.86, 39.43, 54.34, 62.87, 77.20, 80.34, 171.52; IR (KBr) 3282, 3098, 2929, 2856, 1666, 1547, 1467, 1369, 1300, 1248, 1179 cm$^{-1}$; Anal. Calcd. for C$_{16}$H$_{32}$N$_2$O$_4$: C, 62.76; H, 10.53; N, 8.13. Found: C, 63.00; H, 10.46; N, 7.98.

Compound 27 tert-Butyl N-[1-(hydroxymethyl)-2-oxo-2-(tetradecylamino)ethyl]carbamate

To a solution of tetradecyl amine (273 mg, 1.28 mmol) in THF (40 ml), N-(tert-butoxycarbonyl)-L-serine β-lactone (200 mg, 1.06 mmol) was added, and the mixture was refluxed overnight under argon. The reaction mixture was concentrated on a rotary evaporator. The residue was subjected to flash column chromatography, eluting with EtOAc/hexanes of various compositions.

Appropriate fractions were pooled, and concentrated to dryness in vacuo to afford 245 mg (57%) of 27 as a white powder: mp 59–62° C.; $^1$H NMR (CDCl$_3$) δ 0.88 (t, J=6.3 Hz, 3H), 1.25 (s, 24H), 1.45 (s, 9H), 3.15–3.36 (m, 3H), 3.63–3.65 (m, 1H), 4.07–4.13 (m, 2H), 5.60–5.63 (m, 1H), 6.72 (bs, 1H); $^{13}$C NMR (CDCl$_3$) δ 14.10, 22.66, 26.81, 27.99, 28.27, 29.25, 29.33, 29.37, 29.50, 29.57, 29.62, 29.66, 31.90, 39.47, 54.58, 62.87, 77.20, 80.52, 156.34, 171.37; IR (KBr) 3345, 2920, 2852, 1708, 1688, 1655, 1637, 1572, 1529, 1472, 1248, 1173 cm$^{-1}$; Anal. Calcd. for C$_{22}$H$_{44}$N$_2$O$_4$: C, 65.96; H, 11.07; N, 6.99. Found: C, 66.04; H, 11.17; N, 6.96.

Compound 28 tert-Butyl N-[1-(hydroxymethyl)-2-(octadecylamino)-2-oxoethyl]carbamate

To a solution of octadecyl amine (516 mg, 2.08 mmol) in THF (60 ml), N-(tert-butoxycarbonyl)-L-serine β-lactone (300 mg, 1.60 mmol) was added, and the mixture was refluxed overnight under argon. The reaction mixture was concentrated on a rotary evaporator. The residue was subjected to flash column chromatography, eluting with EtOAc/hexanes of various compositions.

Appropriate fractions were pooled, and concentrated to dryness in vacuo to afford 300 mg (41%) of 28 as a white powder: mp 69–71° C.; $^1$H NMR (CDCl$_3$) δ 0.88 (t, J=6.3 Hz, 3H), 1.25 (s, 30H), 1.46 (s, 9H), 3.03 (bs, 1H), 3.16–3.34 (m, 2H), 3.63 (m, 1H), 4.05–4.21 (m, 2H), 5.64 (bs, 1H), 6.62 (bs, 1H); $^{13}$C NMR (CDCl$_3$) δ 14.10, 22.68, 26.81, 28.28, 29.25, 29.35, 29.51, 29.58, 29.69, 31.91, 39.43, 54.29, 62.87, 77.20, 171.53; IR (KBr) 3345, 2919, 2852, 1687, 1636, 1570, 1528, 1473, 1305, 1173 cm$^{-1}$; Anal. Calcd. for $C_{26}H_{52}N_2O_4 \cdot 0.2C_4H_8O_2$: C, 67.86; H, 11.39; N, 5.91. Found: C, 67.59; H, 11.46; N, 6.1.

Compound 29 tert-Butyl N-{1-(hydroxymethyl)-2-oxo-2-[4-(tetredecyloxy)anilino]ethyl}carbamate To a solution of 4-(tetradecyloxy)aniline (150 mg, 0.490 mmol) in THF (40 ml), N-(tert-butoxycarbonyl)-L-serine β-lactone (91 mg, 0.490 mmol) was added, and the mixture was refluxed for 48 hrs under argon. The reaction mixture was concentrated on a rotary evaporator. The residue was subjected to flash column chromatography (twice), eluting with EtOAc/hexanes of various compositions.

Appropriate fractions were pooled, and concentrated to dryness in vacuo to afford 110 mg (45%) of 29 as a white powder: mp 92–94° C.; $^1$H NMR (CDCl$_3$) δ 0.87 (t, J=6.6 Hz, 3H), 1.25 (s, 22H), 1.48 (s, 9H), 1.76 (m, 2H), 3.67–3.72 (dd, J$_1$=4.9 Hz, J$_2$=7.2 Hz, 1H), 3.92 (t, J=6.5 Hz, 2H), 4.23–4.26 (m, 2H), 5.65 (bs, 1H), 6.83–6.87 (m, J$_o$=8.9 Hz, 2H), 7.36–7.40 (m, J$_o$=8.9 Hz), 8.6 (bs, 1H); $^{13}$C NMR (CDCl$_3$) δ 14.10, 22.69, 26.01, 28.28, 29.25, 29.34, 29.39, 29.56, 29.58, 29.64, 31.91, 62.53, 68.30, 77.20, 111.17, 114.81, 121.70, 130.25, 156.22, 169.78; IR (KBr) 3304, 2920, 2852, 1658, 1514, 1472, 1238, 1174 cm$^{-1}$; Anal. Calcd. for $C_{28}H_{48}N_2O_5 \cdot 0.05CHCl_3$: C, 67.56; H, 9.71; N, 5.62. Found: C, 67.80; H, 9.67; N, 5.60.

Compound 30 tert-Butyl N-[1-(hydroxymethyl)-2-(4-methoxyanilino)-2-oxoethyl]carbamate

To a solution of p-anisidine (100 mg, 0.8 mmol) in THF (20 ml) N-(tert-butoxycarbonyl)-L-serine β-lactone (151 mg, 0.8 mmol), was added, and the mixture was refluxed overnight under argon. The reaction mixture was concentrated on a rotary evaporator. The residue was subjected to flash column chromatography, eluting with EtOAc/hexanes of various compositions.

Appropriate fractions were pooled, and were crystallized from CHCl$_3$/hexanes to afford 135 mg (54%) of 30 as a white powder: mp 109–111° C.; $^1$H NMR (CDCl$_3$), δ 1.48 (s, 9H), 3.68–3.73 (m, 1H), 3.80 (s, 3H), 4.24–4.27 (m, 2H), 5.68 (bs, 1H), 6.83–6.88 (m, J$_o$=9 Hz, 2H), 7.37–7.42 (m, J$_o$=9 Hz, 2H), 8.61 (bs, 1H); $^{13}$C NMR (CDCl$_3$) δ 28.29, 54.96, 55.47, 62.54, 81.00, 114.18, 121.78, 130.45, 156.64, 156.98, 169.59; IR (KBr) 3340, 2978, 1673, 1603, 1516, 1298, 1238, cm$^{-1}$; Anal. Calcd. for $C_{15}H_{22}N_2O_5$: C, 58.05; H, 7.15; N, 9.03. Found: C, 58.04; H, 7.17; N, 9.06.

Compound 31 tert-Butyl N-{1-(hydroxymethyl)-2-oxo-2-[3-(tetredecyloxy)anilino]ethyl}carbamate To a solution of 3-(tetradecyloxy)aniline (179 mg, 0.588 mmol) in THF (25 ml), N-(tert-butoxycarbonyl)-L-serine β-lactone (91 mg, 0.490 mmol) was added, and the mixture was refluxed for 48 hrs under argon. The reaction mixture was concentrated on a rotary evaporator. The residue was subjected to flash column chromatography, eluting with EtOAc/hexanes of various compositions.

Appropriate fractions were pooled, and concentrated to dryness in vacuo to afford 105 mg (43%) of 31 as a white powder: mp 70–72° C.; $^1$H NMR (CDCl$_3$) δ 0.88 (t, J=6.6 Hz, 3H), 1.26 (s, 22H), 1.48 (s, 9H), 1.76 (m, 2H), 3.67–3.73 (dd, J$_1$=5.1 Hz, J$_2$=6.9 Hz, 1H), 3.93 (t, J=6.5 Hz, 2H), 4.23–4.26 (m, 2H), 5.66 (bs, 1H), 6.64–6.68 (m, 1H), 6.93–6.96 (m, 1H), 7.19 (t, J$_o$=8.1 Hz, 1H), 7.23 (t, J$_m$=2 Hz, 1H), 8.75 (bs, 1H); $^{13}$C NMR (CDCl$_3$) δ 14.11, 22.68, 26.02, 28.28, 29.23, 29.35, 29.39, 29.60, 29.66, 31.92, 62.38, 68.07, 77.20, 106.22, 111.10, 111.92, 129.67, 138.54, 159.75; IR (KBr) 3368, 2918, 2851, 1679, 1618, 1498, 1472, 1286 cm$^{-1}$; Anal. Calcd. for $C_{28}H_{48}N_2O_5 \cdot 0.05CHCl_3$: C, 67.56; H, 9.71; N, 5.62. Found: C, 67.44; H, 9.79; N, 5.57.

Compound 32 tert-Butyl N-[1-(hydroxymethyl)-2-(3-methoxyanilino)-2-oxoethyl]carbamate

To a solution of m-anisidine (171 mg, 1.38 mmol) in THF (30 ml), N-(tert-butoxycarbonyl)-L-serine β-lactone (200 mg, 1.06 mmol) was added, and the mixture was refluxed overnight under argon. The reaction mixture was concentrated on a rotary evaporator. The residue was subjected to flash column chromatography, eluting with EtOAc/hexanes of various compositions.

Appropriate fractions were pooled, to afford 154 mg (46%) of 32 as a yellow oil; $^1$H NMR (CDCl$_3$), δ 1.48 (s, 9H), 3.68–3.73 (dd, J$_1$=4.8 Hz, J$_2$=6.9 Hz, 1H), 3.75 (s, 3H), 4.22–4.25 (d, J=10.23 Hz, 2H), 5.66 (bs, 1H), 6.66–6.69 (m, 1H), 6.96–6.99 (m, 1H), 7.21 (m, J$_o$=8.1 Hz, 1H), 7.24 (m, 1H), 8.79 (bs, 1H); $^{13}$C NMR (CDCl$_3$) δ 28.28, 29.68, 55.30, 62.39, 77.20, 81.11, 105.67, 110.55, 112.15, 129.73, 138.63, 160.19, 169.89.

Compound 33 tert-Butyl N-{1-(hydroxymethyl)-2-oxo-2-[2-(tetredecyloxy)anilino]ethyl}carbamate To a solution of 2-(tetradecyloxy)aniline (200 mg, 0.654 mmol) in THF (25 ml), N-(tert-butoxycarbonyl)-L-serine β-lactone (102 mg, 0.545 mmol) was added, and the mixture was refluxed for 48 hrs under argon. The reaction mixture was concentrated on a rotary evaporator. The residue was subjected to flash column chromatography, eluting with EtOAc/hexanes of various compositions.

Appropriate fractions were pooled, and concentrated to dryness in vacuo to afford 33 mg (<10%) of 33 as a yellow oil: $^1$H NMR (CDCl$_3$) δ 0.88 (t, J=6.6 Hz, 3H), 1.26 (s, 22H), 1.48 (s, 9H), 1.76 (m, 2H), 3.67–3.73 (dd, J$_1$=5.1 Hz, J$_2$=6.9 Hz, 1H), 3.93 (t, J=6.5 Hz, 2H), 4.23–4.26 (m, 2H), 5.66 (bs, 1H), 6.64–6.68 (m, 1H), 6.93–6.96 (m, 1H), 7.19 (t, J$_o$=8.1 Hz, 1H), 7.23 (t, J$_m$=2 Hz, 1H), 8.75 (bs, 1H); $^{13}$C NMR (CDCl$_3$) δ 14.10, 22.68, 25.88, 28.30, 29.17, 29.35, 29.58, 29.64, 29.68, 31.91, 55.73, 63.03, 68.71, 77.20, 111.06, 119.86, 119.86, 120.78, 124.21, 127.27, 147.75, 157.22, 169.25.

Compound 34 tert-Butyl N-[1-(hydroxymethyl)-2-(2-methoxyanilino)-2-oxoethyl]carbamate

To a solution of o-anisidine (238 mg, 1.93 mmol) in THF (30 ml), N-(tert-butoxycarbonyl)-L-serine β-lactone (200 mg, 1.06 mmol) was added, and the mixture was refluxed for 48 hrs under argon. The reaction mixture was concentrated on a rotary evaporator. The residue was subjected to flash column chromatography, eluting with EtOAc/hexanes of various compositions.

Appropriate fractions were pooled, and crystallized from CHCl$_3$/hexanes to afford 150 mg (45%) of 34 as a yellow powder: mp 92–94° C.; $^1$H NMR (CDCl$_3$), δ 1.49 (s, 9H), 3.87 (s, 3H), 3.73–3.83 (m, 1H), 4.21–4.34 (m, 2H), 5.64 (bs, 1H), 6.86–6.97 (m, 2H), 7.03–7.09 (m, J$_o$=7.80 Hz, J$_m$=1.8 Hz, 1H), 8.28–8.31 (dd, J$_o$=8.9 Hz, J$_m$=1.5 Hz, 1H) 8.9 (bs, 1H); $^{13}$C NMR (CDCl$_3$) δ 28.28, 55.73, 62.87, 80.65, 110.14, 120.03, 120.97, 124.30, 127.13, 148.33, 169.43; IR (KBr) 3525, 3319, 2982, 1672, 1653, 1548, 1528, 1465, 1256, 1160, 1006 cm$^{-1}$; Anal. Calcd. for C$_{15}$H$_{22}$N$_2$O$_5$: C, 58.05; H, 7.15; N, 9.03. Found: C, 58.04; H, 7.07; N, 8.85.

Example 3

Synthesis of Compounds 35–43

Compound 35

N-1-nonyl-2-amino-3-hydroxypropanamide trifluoroacetate

To a cooled (0° C., ice bath) solution of 26 (20 mg, 0.0580 mmol) in CH$_2$Cl$_2$ (1 ml), TFA (1 ml) was added dropwise under argon atmosphere. After the addition was complete, the reaction was allowed to stir at r.t., for 3 hrs, concentrated under reduced pressure at room temperature, and dried on a vacuum pump to give 35 as a white solid 19 mg (95%): mp 168–170° C.; $^1$H NMR (CD$_3$OD), δ 0.88 (t, J=6.3 Hz, 3H), 1.27 (s, 14H), 1.50 (m, 2H), 3.20 (t, J=6.0 Hz, 2H), 3.70–3.78 (m, 1H), 3.81–3.88 (m, 2H); $^{13}$C NMR (CD$_3$OD) δ 14.44, 23.74, 27.96, 30.30, 30.42, 30.47, 30.70, 30.73, 30.78, 30.80, 33.10, 40.71, 56.30, 61.77, 167.97; IR (KBr) 3280, 2919, 2850, 1654, 1573, 1464, 1231, 1141, 1089, 1059, cm$^{-1}$. Anal. Calcd. for C$_{13}$H$_{28}$N$_2$O$_2$.CF$_3$COOH: C, 50.27; H, 8.16; N, 7.82. Found: C, 50.15; H, 8.30; N, 7.95.

Compound 36

N-1-tetradecyl-2-amino-3-hydroxypropanamide trifluoroacetate

To a cooled (0° C., ice bath) solution of 27 (50 mg, 0.124 mmol) in CH$_2$C$_2$ (1.5 ml), TFA (1.5 ml) was added dropwise under argon atmosphere. After the addition was complete, the reaction was allowed to stir at r.t. for 3 hrs, concentrated under reduced pressure at room temperature, and dried on a vacuum pump to give 36 as a white solid 48 mg (94%): mp 168–171° C.; $^1$H NMR (CD$_3$OD), δ 0.89 (t, J=6.3 Hz, 3H), 1.28 (s, 22H), 3.22 (t, J=6.0 Hz, 2H), 3.73–3.80 (m, 1H), 3.84–3.91 (m, 2H); $^{13}$C NMR (CD$_3$OD) δ 14.43, 23.73, 27.95, 30.29, 30.41, 30.47, 30.69, 30.73, 30.78, 30.80, 33.08, 40.71, 56.29, 61.77, 167.99; IR (KBr) 3277, 2919, 2850, 1656, 1573, 1464, 1231, 1141, 1089, 1059 cm$^{-1}$; Anal. Calcd. for C$_{17}$H$_{36}$N$_2$O$_2$.CF$_3$COOH: C, 55.06; H, 9.00; N, 6.76. Found: C, 54.94; H, 8.99; N, 6.58.

Compound 37

N-1-octadecyl-2-amino-3-hydroxypropanamide trifluoroacetate

To a cooled (0° C., ice bath) solution of 28 (25 mg, 0.0547 mmol) in CH$_2$Cl$_2$ (1 ml), TFA (1 ml) was added dropwise under argon atmosphere. After the addition was complete, the reaction was allowed to stir at r.t., for 3 hrs, concentrated under reduced pressure at room temperature, and dried on a vacuum pump to give 37 as a white solid 23 mg (92%): mp 170–172° C.; $^1$H NMR (CD$_3$OD) δ 0.89 (t, J=6.4 Hz, 3H), 1.27 (s, 30H), 1.49–1.54 (m, 2H), 3.22 (t, J=7.0 Hz, 2H), 3.74–3.81 (m, 1H), 3.83–3.91 (m, 2H); $^{13}$C NMR (CD$_3$OD) δ 14.43, 23.74, 27.95, 30.30, 30.41, 30.47, 30.69, 30.78, 33.07, 40.71, 56.30, 61.77, 167.97; IR (KBr) 3276, 2919, 2850, 1657, 1468, 1207, 1181, 1138, 1059 cm$^{-1}$; Anal. Calcd. for C$_{21}$H$_{44}$N$_2$O$_2$.CF$_3$COOH 0.15CH$_2$Cl$_2$: C, 57.53; H, 9.45; N, 5.80. Found: C, 57.45; H, 9.55; N, 5.81.

Compound 38

N-1-[4-(tetradecyloxy)phenyl]-2-amino-3-hydroxypropanamide trifluoroacetate

To a cooled (0° C., ice bath) solution of 29 (54 mg, 0.110 mmol) in CH$_2$Cl$_2$ (0.050 ml), TFA (0.050 ml) was added dropwise under argon atmosphere. After the addition was complete, the reaction was allowed to stir at r.t., for 3 hrs, concentrated under reduced pressure at room temperature, and then, dried on a vacuum pump to give 38 as a white solid 55 mg (99%): mp 135–139° C.; $^1$H NMR (CD$_3$OD), δ 0.89 (t, J=6.3 Hz, 3H), 1.28 (s, 21H), 1.43 (m, 2H), 1.74 (m, J=6.5 Hz, 2H), 3.86–4.03 (m, 5H), 6.84–6.88 (m, J$_o$=9.0 Hz, 2H), 7.41–7.47 (m, J$_o$=9.0 Hz, 2H); $^{13}$C NMR (CD$_3$OD) δ 14.42, 23.72, 30.41, 30.46, 30.50, 30.67, 30.74, 33.06, 56.81, 61.72, 69.26, 115.71, 122.96, 131.84, 157.80, 166.06; IR (KBr) 3281, 2920, 2852, 1672, 1604, 1559, 1515, 1240, 1210, 1132 cm$^{-1}$; Anal. Calcd. for C$_{23}$H$_{40}$N$_2$O$_3$.CF$_3$COOH: C, 59.27; H, 8.16; N, 5.53. Found: C, 59.48; H, 8.09; N, 5.49.

Compound 39

N-1-(4-methoxyphenyl)-2-amino-3-hydroxypropanamide trifluoroacetate

To a cooled (0° C., ice bath) solution of 30 (50 mg, 0.161 mmol) in CH$_2$Cl$_2$ (0.049 ml), TFA (0.049 ml) was added dropwise under argon atmosphere. After the addition was complete, the reaction was allowed to stir at r.t., for 3 hrs, concentrated under reduced pressure at r.t., and concentrated to dryness in vacuo to give 39 as a white solid 50 mg (96%): mp 182–183° C. dec; $^1$H NMR (CD$_3$OD), δ 3.76 (s, 3H), 3.87–3.94 (m, 1H), 3.97–4.04 (m, 2H), 6.85–6.91 (m, J$_o$=9.1 Hz, 2H), 7.44–7.49 (m, J$_o$=9.0 Hz, 2H); $^{13}$C NMR (CD$_3$OD) δ 55.86, 56.80, 61.73, 115.07, 122.95, 131.99, 158.31, 166.10; IR (KBr) 3278, 3099, 2964, 1673, 1562, 1517, 1196, 1131, cm$^{-1}$; Anal. Calcd. for C$_{10}$H$_{14}$N$_2$O$_3$.CF$_3$COOH: C, 44.45; H, 4.66; N, 8.64. Found: C, 44.31; H, 4.67; N, 8.58.

Compound 40

N-1-[3-(tetradecyloxy)phenyl]-2-amino-3-hydroxypropanamide trifluoroacetate

To a cooled (0° C., ice bath) solution of 31 (45 mg, 0.091 mmol) in CH$_2$Cl$_2$ (0.062 ml), TFA (0.062 ml) was added dropwise under argon atmosphere. After the addition was complete, the reaction was allowed to stir at r.t. for 3 hrs, concentrated under reduced pressure at room temperature, and dried on a vacuum pump to give 40 as a yellowish green solid 45 mg (99%): mp 115–119° C.; $^1$H NMR (CD$_3$OD), δ 0.89 (s, J=6.5 Hz, 3H), 1.28 (s, 21H), 1.43 (m, 2H), 1.75 (m, J=6.5 Hz, 2H), 3.8–3.93 (m, 4H), 4.01–4.05 (m, 1H), 6.67–6.71 (m, 1H), 7.04–7.07 (m, 1H), 7.20 (t, J$_o$=8.1 Hz, 1H), 7.28 (t, J$_m$=2.1 Hz, 1H); $^{13}$C NMR (CD$_3$OD) δ 14.44, 23.75, 27.18, 30.38, 30.49, 30.52, 30.73, 30.78, 33.09, 56.96, 61.66, 69.05, 107.71, 111.75, 113.16, 130.72, 140.16, 161.07, 166.36; IR (KBr) 3266, 2920, 2852, 1676, 1608, 1566, 1496, 1438, 1211, 1130, 1045 cm$^{-1}$; Anal. Calcd. for C$_{23}$H$_{40}$N$_2$O$_3$.CF$_3$COOH: C, 59.27; H, 8.16; N, 5.53. Found: C, 59.49; H, 8.13; N, 5.41.

Compound 41

N-1-(3-methoxyphenyl)-2-amino-3-hydroxypropanamide trifluoroacetate

To a cooled (0° C., ice bath) solution of 32 (120 mg, 0.386 mmol) in $CH_2Cl_2$ (1 ml), TFA (1 ml) was added dropwise under argon atmosphere. After the addition was complete, the reaction was allowed to stir at r.t., for 3 hrs, concentrated under reduced pressure at r.t., and dried on a vacuum pump to give 41 as a offwhite solid 123 mg (98%): mp 137–140° C.; $^1$H NMR ($CD_3OD$), δ 3.77 (s, 3H), 3.88–3.99 (m, 2H), 4.01–4.06 (m, 1H), 6.68–6.71 (m, 1H), 7.02–7.10 (m, 1H), 7.22 (t, $J_o$=8.1 Hz, 1H), 7.29 (t, $J_m$=2.1 Hz, 1H); $^{13}$C NMR ($CD_3OD$) δ 55.70, 56.94; 61.67, 107.14, 111.11, 113.28, 130.73, 140.22, 161.61, 166.43; IR (KBr) 3265, 1675, 1609, 1566, 1496, 1433, 1268, 1196, 1044, $cm^{-1}$; Anal. Calcd. for $C_{10}H_{14}N_2O_3 \cdot CF_3COOH$: C, 44.45; H, 4.66; N, 8.64. Found: C, 44.52; H, 4.59; N, 8.66.

Compound 42

N-1-[2-(tetradecyloxy)phenyl]-2-amino-3-hydroxypropanamide trifluoroacetate

To a cooled (0° C., ice bath) solution of 33 (21 mg, 0.044 mmol) in $CH_2Cl_2$ (1 ml), TFA (1 ml) was added dropwise under argon atmosphere. After the addition was complete, the reaction was allowed to stir at r.t., for 3 hrs, concentrated under reduced pressure at room temperature, and dried on a vacuum pump to give 42 as a offwhite solid 21 mg (95%): mp 63–66° C.; $^1$H NMR ($CD_3OD$), δ 0.88 (t, J=6.5 Hz, 3H), 1.27 (s, 21H), 1.46 (m, 2H), 1.83 (m, J=7.8 Hz, 2H), 3.90–4.07 (m, 4H), 4.18 (t, J=5.8 Hz, 1H), 6.87–6.93 (m, 1H), 6.99–7.02 (m, 1H), 7.08–7.14 (m, 1H), 7.96–7.99 (m, 1H); $^{13}$C NMR ($CD_3OD$) δ 14.43, 23.73, 27.07, 30.27, 30.48, 30.57, 30.79, 33.07, 56.198, 61.67, 69.84, 112.93, 121.40, 123.38, 126.80, 127.53, 150.93, 166.74; IR (KBr) 3282, 2925, 2851, 1679, 1556, 1496, 1458, 1213, 750, $cm^{-1}$; Anal. Calcd. for $C_{23}H_{40}N_2O_3 \cdot CF_3COOH \cdot 0.5H_2O$: C, 58.24; H, 8.21; N, 5.43. Found: C, 58.59; H, 8.09; N, 5.24.

Compound 43

N-1-(2-methoxyphenyl)-2-amino-3-hydroxypropanamide trifluoroacetate

To a cooled (0° C., ice bath) solution of 34 (80 mg, 0.257 mmol) in $CH_2Cl_2$ (1 ml), TFA (1 ml) was added dropwise under argon atmosphere. After the addition was complete, the reaction was allowed to stir at r.t., for 3 hrs, concentrated under reduced pressure at room temperature, and dried on a vacuum pump to give 43 as a off white solid 81 mg (97%): mp 131–133° C.; $^1$H NMR ($CD_3OD$), δ 3.88 (s, 3H), 3.91–4.02 (m, 2H), 4.18–4.22 (m, 1H), 6.89–6.94 (m, 1H), 7.01–7.04 (m, 1H), 7.10–7.16 (t, $J_o$=8.1 Hz, 1H), 8.00–8.03 (t, $J_m$=2.1 Hz, 1H); $^{13}$C NMR ($CD_3OD$) δ 56.27, 56.34, 56.47, 61.81, 111.94, 121.52, 123.21, 126.71, 127.54, 151.43, 166.80; IR (KBr) 3271, 1675, 1546, 1499, 1465, 1439, 1268, 1207, 1130, $cm^{-1}$; Anal. Calcd. for $C_{10}H_{14}N_2O_3 \cdot CF_3COOH$: C, 44.45; H, 4.66; N, 8.64. Found: C, 44.18; H, 4.57; N, 8.59.

Example 4

Synthesis of Intermediate Compounds 50–54

The glassware used is flame-dried and cooled to room temperature under an argon atmosphere. The starting alcohol was washed with anhydrous pyridine (3 times), and dried (high vacuum for 48 hrs). The reaction was carried out in an argon atmosphere. THF and $CH_2Cl_2$ were freshly distilled prior to their use.

Compound 50 tert-Butyl N-[1-{([di(benzyloxy)phosphoryl]oxy)methyl}-2-(nonylamino)-2-oxoethyl]carbamate To the pyridine-washed starting 28 (252 mg, 0.551 mmol) was added 1H-tetrazole (231 mg, 3.31 mmol). To this mixture was added a 1:1 mixture of freshly distilled THF/$CH_2Cl_2$ (50 ml). After 10 mins, dibenzyldiisopropyl phosphoramidate (1.14 gm, 3.31 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and $CH_2Cl_2$ were removed under reduced pressure. The concentrate was treated with EtOAc (70 ml), and was washed with Na-metabisulfite (2×25 ml), $NaHCO_3$ (2×30 ml), water (2×30 ml), and brine (2×30 ml). The organic portion was dried over $NaSO_4$, and concentrated under reduced pressure. The residue was subjected to flash column chromatography, eluting with EtOAc/hexanes of various compositions.

Appropriate fractions were pooled, and concentrated to dryness in vacuo to afford 195 mg (49%) of 50 as a colorless oil: $^1$H NMR ($CDCl_3$) δ 0.87 (t, J=6.4 Hz, 3H), 1.25 (bm, 29H), 1.34 (m, 2H), 1.44 (s, 9H), 3.17–3.23 (m, 2H), 4.01–4.09 (m, 1H), 4.31–4.43 (m, 2H), 4.96–5.09 (m, 4H), 5.55 (bs, 1H), 6.33 (bs, 1H) 7.31–7.39 (m, 10H); $^{13}$C ($CDCl_3$) δ 14.09, 22.66, 26.79, 28.25, 29.24, 29.27, 29.42, 29.50, 29.53, 31.86, 39.68, 66.98, 69.66, 69.73, 77.20, 128.06, 128.10, 128.64, 128.70, 128.72, 135.02, 168.50; MS m/z 603 (M–H)$^-$; IR (KBr) 3349, 2919, 2852, 1717, 1685, 1654, 1516, 1470, 1457, 1242, 1163, 1037, 1025, 999 $cm^{-1}$.

Compound 51 tert-Butyl N-[1-{([di(benzyloxy)phosphoryl]oxy)methyl}-2-oxo-2-(tetradecylamino)ethyl]carbamate To the pyridine-washed starting 27 (305 mg, 0.761 mmol) was added 1H-tetrazole (319 mg, 4.56 mmol). To this mixture was added a 1:1 mixture of freshly distilled THF/$CH_2Cl_2$ (40 ml). After 10 mins, dibenzyldiisopropyl phosphoramidate (1.57 gm, 4.56 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and $CH_2Cl_2$ were removed under reduced pressure. The concentrate was treated with EtOAc (70 ml), and was washed with Na-metabisulfite (2×30 ml), $NaHCO_3$ (2×40 ml), water (2×35 ml), and brine (2×35 ml). The organic portion was dried over $NaSO_4$, and concentrated under reduced pressure. The residue was subjected to flash column chromatography, eluting with EtOAc/hexanes of various compositions.

Appropriate fractions were pooled, and concentrated to dryness in vacuo to afford 451 mg (89%) of 51 as a white waxy solid: mp 33–35° C.; $^1$H NMR ($CDCl_3$) δ 0.87 (t, J=6.4 Hz, 3H), 1.23–1.25 (bm, 22H), 1.44 (s, 9H), 1.52–1.55

(m, 2H), 3.16–3.23 (m, 2H), 4.02–4.09 (m, 1H), 4.31–4.43 (m, 2H), 5.00–5.15 (m, 4H), 5.57 (bs, 1H), 6.34 (t, J=5.0 Hz, 1H) 7.31–7.40 (m, 10H); $^{13}$C (CDCl$_3$) δ 14.08, 19.03, 22.67, 26.81, 28.27, 29.25, 29.33, 29.44, 29.51, 29.59, 29.62, 29.65, 31.91, 39.69, 46.49, 54.47, 67.00, 67.07, 67.24, 67.32, 69.66, 69.68, 69.74, 76.12, 77.20, 77.84, 80.57, 128.0, 128.05, 128.09, 128.58, 128.64, 128.68, 135.45, 135.54, 135.59, 168.51; Anal. Calcd. for C$_{36}$H$_{57}$N$_2$O$_7$P.1H$_2$O.0.5C$_4$H$_8$O$_2$: C, 63.14; H, 8.78; N, 3.88. Found: C, 62.80; H, 8.38; N, 4.21.

Compound 52 tert-Butyl N-[1-{([di(benzyloxy)phosphoryl]oxy) methyl}-2-(octadecylamino)-2-oxoethyl]carbamate To the pyridine-washed starting 26 (270 mg, 0.783 mmol) was added 1H-tetrazole (329 mg, 4.70 mmol). To this mixture was added a 1:1 mixture of freshly distilled THF/CH$_2$Cl$_2$ (50 ml). After 10 mins, dibenzyldiisopropyl phosphoramidate (1.62 gm, 4.70 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and CH$_2$Cl$_2$ were removed under reduced pressure. The concentrate was treated with EtOAc (50 ml), and was washed with Na-metabisulfite (2×25 ml), NaHCO$_3$ (2×25 ml), water (2×25 ml), and brine (2×25 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 135 mg (28%) of 52 as a white solid: mp 52–54° C.; $^1$H NMR (CDCl$_3$) δ 0.87 (t, J=6.4 Hz, 3H), 1.23 (bm, 14H), 1.44 (s, 9H), 1.63 (m, 2H), 3.17–3.24 (m, 2H), 4.01–4.09 (m, 1H), 4.30–4.44 (m, 2H), 5.00–5.05 (m, 4H), 5.56 (bs, 1H), 6.32 (bs, 1H) 7.29–7.39 (m, 10H), $^{13}$C(CDCl$_3$) δ 14.11, 22.68, 26.80, 28.25, 29.26, 29.35, 29.42, 29.52, 29.60, 29.64, 29.69, 31.91, 39.68, 67.00, 67.07, 69.69, 69.74, 77.20, 127.93, 128.06, 128.10, 128.65, 128.70, 128.73, 135.43, 168.51, 170.07; IR (KBr) 3349, 2919, 2852, 1717, 1685, 1654, 1516, 1242, 1163, 1037, 1025, 999 cm$^{-1}$; Anal. Calcd. for C$_{40}$H$_{65}$N$_2$O$_7$P.0.75H$_2$O.1C$_4$H$_8$O$_2$: C, 64.56; H, 9.17; N, 3.42. Found: C, 64.23; H, 9.05; N, 3.78.

Compound 53 tert-Butyl N-{1-{([di(benzyloxy)phosphoryl]oxy) methyl}-2-oxo-2-[4-(tetradecyloxy)anilino] ethyl}carbamate To the pyridine-washed starting 29 (310 mg, 0.647 mmol) was added 1H-tetrazole (450 mg, 6.42 mmol). To this mixture was added a 1:1 mixture of freshly distilled THF/CH$_2$Cl$_2$ (40 ml). After 10 mins, dibenzyldiisopropyl phosphoramidate (2.21 gm, 6.42 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and CH$_2$Cl$_2$ were removed under reduced pressure. The concentrate was treated with EtOAc (70 ml), and was washed with Na-metabisulfite (2×25 ml), NaHCO$_3$ (2×35 ml), water (2×35 ml), and brine (2×35 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 81 mg (17%) of 53 as a white solid: mp 74–76° C.; $^1$H NMR (CDCl$_3$) δ 0.87 (t, J=6.5 Hz, 3H), 1.30 (s, 22H), 1.46 (s, 9H), 1.71–1.80 (m, 2H), 3.91 (t, J=6.5 Hz, 3H), 4.01–4.16 (m, 1H), 4.42–4.49 (m, 2H), 4.96–5.09 (m, 4H), 5.65 (bs, 1H), 6.80–6.86 (m, J$_o$=9.0 Hz, 2H) 7.31–7.39 (m, 12H), 8.82 (bs, 1H); $^{13}$C (CDCl$_3$) δ 14.10, 22.67, 26.02, 28.26, 29.26, 29.34, 29.40, 29.57, 29.64, 31.91, 68.31, 69.84, 77.20, 114.79, 121.72, 128.07, 128.13, 128.65, 128.74, 130.03, 166.71; IR (KBr) 3340, 2920, 2852, 1717, 1677, 1513, 1457, 1237, 1059, 998 cm$^{-1}$; Anal. Calcd. for C$_{42}$H$_{61}$N$_2$O$_8$P.1H$_2$O.0.45C$_6$H$_{14}$: C, 66.31; H, 8.63; N, 3.46. Found: C, 65.92; H, 9.02; N, 3.84.

Compound 54 tert-Butyl N-[1-{([di(benzyloxy)phosphoryl]oxy) methyl}-2-(4-methoxyanilino)-2-oxoethyl]carbamate To the pyridine-washed starting 30 (225 mg, 0.725 mmol) was added 1H-tetrazole (254 mg, 3.625 mmol). To this mixture was added a 1:1 mixture of freshly distilled THF/CH$_2$Cl$_2$ (20 ml). After 10 mins, dibenzyldiisopropyl phosphoramidate (1.25 gm, 3.625 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and CH$_2$Cl$_2$ were removed on a rotary evaporator. The concentrate was treated with EtOAc (50 ml), and was washed with Na-metabisulfite (2×15 ml), NaHCO$_3$ (2×25 ml), water (2×25 ml), and brine (2×25 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 195 mg (47%) of 54 as a white solid: mp 82–84° C.; $^1$H NMR (CDCl$_3$) δ 1.44 (s, 9H), 4.11 (s, 3H), 4.09–4.18 (m, 1H), 4.43–4.51 (m, 2H), 4.98–5.05 (m, 4H), 5.72 (bs, 1H), 6.78–6.82 (m, J$_o$=9.0 Hz, 2H) 7.26–7.33 (m, 10H), 7.36–7.41 (m, J$_o$=9.0 Hz, 2H), 8.41 (bs, 1H); $^{13}$C (CDCl$_3$) δ 28.26, 55.45, 66.93, 67.00, 69.76, 69.83, 69.90, 77.20, 80.91, 114.11, 121.75, 128.06, 128.12, 128.64, 128.72, 128.73, 130.38, 135.28, 135.42, 156.62, 166.75; $^{31}$P NMR (CDCl$_3$) δ 16.72 (1P); IR (KBr) 3337, 2969, 1716, 1689, 1665, 1514, 1457, 1304, 1245, 999 cm$^{-1}$; Anal. Calcd. for C$_{19}$H$_{35}$N$_2$O$_8$P: C, 61.05; H, 6.18; N, 4.91. Found: C, 60.80; H, 6.20; N, 4.88.

Example 5

Synthesis of Compounds 55–59

Compound 55

2-Amino-3-(nonylamino)-3-oxopropyl dihydrogen phosphate

To a solution of 50 (100 mg, 0.165 mmol) in EtOH (15 ml) was added 10% Pd/C (catalytic amount). Hydrogenation was carried out for 4 hrs at 50 psi. After 4 hours TLC determined the completion of the reaction, the reaction mixture was filtered through celite, and the eluate was concentrated under reduced pressure to afford 48 mg (90%) of 55 as a white powder: mp 196–198° C.; $^1$H NMR (CF$_3$COOD) δ 0.81–0.82 (m, 3H), 1.26–1.30 (m, 14H), 1.59 (m, 2H), 3.37–3.38 (m, 2H), 4.54–4.59 (m, 1H), 4.72–4.81 (m, 2H); $^{13}$C NMR (CF$_3$COOD) δ 14.66, 24.39, 28.60, 28.60, 30.46, 30.94, 31.16, 31.30, 31.39, 33.81, 43.53, 57.21, 66.42, 167.86; MS m/z 323 (M–H)$^-$; IR (KBr) 3314, 2920, 2853, 1670, 1575, 1477, 1246, 1063, 1043 cm$^{-1}$; Anal. Calcd. for C$_{13}$H$_{29}$N$_2$O$_5$P.0.5CH$_3$OH: C, 47.64; H, 9.18; N, 8.23. Found: C, 47.24; H, 8.84; N, 8.02.

Compound 56

2-Amino-3-oxo-3-(tetradecylamino)propyl dihydrogen phosphate

To a solution of 51 (145 mg, 0.219 mmol) in EtOH (15 ml) was added 10% Pd/C (catalytic amount). Hydrogenation was carried out for 3 hrs at 45 psi. After 3 hours TLC determined the completion of the reaction, the reaction mixture was filtered through celite, and the eluate was concentrated under reduced pressure to afford 75 mg (90%) of 56 as a white powder: mp 189–190° C.; $^1$H NMR (CF$_3$COOD) δ 0.81 (bs, 3H), 1.24 (s, 23H), 1.57 (m, 2H), 3.37 (m, 2H), 4.54–4.58 (m, 1H), 4.73–4.78 (m, 2H); $^{13}$C NMR (CF$_3$COOD) δ 14.43, 24.16, 28.34, 30.21, 30.69, 31.01, 31.17, 31.22, 31.27, 33.62, 43.27, 56.96, 66.16, 167.60; $^{31}$P NMR (CF$_3$COOD) δ 17.93 (1P); MS m/z 379 (M–H)$^-$; IR (KBr) 3318, 2923, 2852, 1671, 1657, 1563, 1475, 1242, 1055 cm$^{-1}$; Anal. Calcd. for C$_{17}$H$_{37}$N$_2$O$_5$P: C, 53.67; H, 9.80; N, 7.36. Found: C, 53.40; H, 9.73; N, 7.31.

Compound 56a 2-(Acetylamino)-3-oxo-3-(tetradecylamino) propyl dihydrogen phosphate To a sample of 56 (20 mg, 0.052 mmol) in 0.5 ml pyridine was added a large excess of acetic anhydride. The mixture was allowed to stir at r.t. overnight. Excess pyridine and acetic anhydride were on a rotary evaporator. The resultant mixture was stirred with 20 ml of aqueous HCl. The acidic mixture was extracted with EtOAc (2×25 ml). The EtOAc layer was washed with water (2×25 ml) and brine (2×25 ml). The organic portion was dried over NaSO$_4$ and filtered. The eluate was concentrated under reduced pressure to afford 15 mg (71%) of 56a as a gummy solid: $^1$H NMR (CD$_3$OD), δ 0.89 (t, J=6.3 Hz, 3H), 1.27 (s, 22H), 1.99–2.02 (m, 3H), 3.15–3.20 (m, 2H), 4.10–4.28 (m, 2H), 4.54–4.62 (m, 1H); $^{13}$C NMR (CDCl$_3$/CD$_3$OD) 13.48, 16.19, 22.23, 26.50, 28.91, 29.21, 31.48, 30.21, 31.01, 31.17, 31.22, 31.27, 33.62, 43.27, 56.96, 66.16, 163.02, 174.96; IR (KBr) 3316, 2923, 2853, 1671, 1657, 1560, 1467, 1247, 1059 cm$^{-1}$.

Compound 57

2-Amino-3-(octadecylamino)-3-oxopropyl dihydrogen phosphate

To a solution of 52 (117 mg, 0.164 mmol) in EtOH (15 ml) was added 10% Pd/C (catalytic amount). Hydrogenation was carried out for 4 hrs at 50 psi. After 4 hours TLC determined the completion of the reaction, the reaction mixture was filtered through celite, and the eluate was concentrated under reduced pressure to afford 70 mg (98%) of 57 as a white powder: mp 190–192° C.; $^1$H NMR (CF$_3$COOD) δ 0.81 (t, J=6.9 Hz, 3H), 1.25 (s, 31H), 1.58 (m, 2H), 3.34–3.44 (m, 2H), 4.49–4.59 (m, 1H), 4.71–4.81 (m, 2H); $^{13}$C NMR (CF$_3$COOD) δ 14.70, 24.43, 28.60, 30.46, 30.95, 31.28, 31.31, 31.44, 31.48, 31.55, 33.89, 43.53, 57.12, 57.21, 66.35, 167.85; MS m/z 435 (M–H)$^-$; IR (KBr) 3325, 2922, 2852, 1674, 1655, 1560, 1472, 1045 cm$^{-1}$; Anal. Calcd. for C$_{21}$H$_{45}$N$_2$O$_5$P: C, 57.77; H, 10.39; N, 6.42. Found: C, 57.61; H, 10.22; N, 6.25.

Compound 58

2-Amino-3-oxo-3-[4-(tetradecyloxy)anilino]propyl dihydrogen phosphate

To a solution of 53 (40 mg, 0.054 mmol) in EtOH (15 ml) was added 10% Pd/C (catalytic amount). Hydrogenation was carried out for 4 hrs at 50 psi. After 4 hours TLC determined the completion of the reaction, the reaction mixture was filtered through celite, and the eluate was concentrated under reduced pressure to afford 22 mg (88%) of 58 as a white powder: mp 187–190° C.; $^1$H NMR (CF$_3$COOD) δ 0.80–0.82 (m, 3H), 1.25 (m, 20H), 1.77–1.84 (m, 2H), 4.20 (t, J=6.0 Hz, 2H), 4.64–4.74 (m, 1H), 4.90–4.91 (m, 2H), 7.04–7.07 (d, J$_o$=9.0 Hz, 2H), 7.32–7.35 (d, J$_o$=9.0 Hz, 2H); $^{13}$C NMR (CF$_3$COOD) δ 14.81, 24.54, 27.57, 30.62, 31.19, 31.38, 31.46, 31.52, 31.60, 31.65, 33.99, 57.70, 66.53, 73.66, 119.32, 126.55, 131.25, 158.87, 167.06; MS m/z 471 (M–H)$^-$; IR (KBr) 3325, 2923, 2852, 1665, 1553, 1515, 1469, 1240, 1046 cm$^{-1}$; Anal. Calcd. for C$_{23}$H$_{41}$N$_2$O$_6$P.0.5CH$_3$OH.0.5CHCl$_3$: C, 52.58; H, 8.00; N, 5.11. Found: C, 52.89; H, 7.83; N, 5.29.

Compound 59

2-Amino-3-(4-methoxyanilino)-3-oxopropyl dihydrogen phosphate

To a solution of 54 (125 mg, 0.219 mmol) in EtOH (15 ml) was added 10% Pd/C (catalytic amount). Hydrogenation was carried out for 2 hrs at 45 psi. After 2 hours TLC determined the completion of the reaction, the reaction mixture was filtered through celite, and the eluate was concentrated under reduced pressure to afford 82 mg (96%) of 59 as a white powder: mp 199–202° C.; $^1$H NMR (CF$_3$COOD) δ 3.93 (s, 3H), 4.65–4.75 (m, 1H), 4.88–4.94 (m, 2H), 7.01–7.04 (d, J$_o$=9.0 Hz, 2H), 7.31–7.34 (d, J$_o$=9.0 Hz, 2H); $^{13}$C NMR (CDCl$_3$) δ 57.60, 58.00, 66.54, 117.69, 126.64, 131.07, 159.62, 167.07; MS m/z 289 (M–H)$^-$; IR (KBr) 3317, 2961, 1680, 1565, 1515, 1478, 1236, 1045 cm$^{-1}$; Anal. Calcd. for C$_{10}$H$_{15}$N$_2$O$_6$P: C, 41.39; H, 5.21; N, 9.65. Found: C, 41.25; H, 5.35; N, 9.73.

Example 6

Synthesis of Intermediate Compounds 63–65

The glassware used was flame-dried and cooled to room temperature under an argon atmosphere. The starting alcohol was washed with anhydrous pyridine (3 times) and dried on high vacuum for 48 hrs. The reaction was carried out in an argon atmosphere. THF and CH$_2$Cl$_2$ were freshly distilled prior to their use.

Compound 63

1,2-(3-Octadecyloxypropane)-bis(dibenzylphosphate)

To the pyridine-washed starting dl-batyl alcohol (60, 225 mg, 0.652 mmol) was added 1H-tetrazole (229 mg, 3.26 mmol). To this mixture was added a 1:1 mixture of freshly distilled THF/CH$_2$Cl$_2$ (50 ml). After 10 mins, dibenzyldiisopropyl phosphoramidate (1.12 gm, 3.26 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and CH$_2$Cl$_2$ were removed under reduced pressure. The concentrate was treated with EtOAc (70 ml), and was washed with Na-metabisulfite (2×25 ml), NaHCO$_3$ (2×30 ml), water (2×30 ml), and brine (2×30 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 303 mg (53%) of 63 as a clear oil: $^1$H NMR (CDCl$_3$) δ 0.86 (t, J=6.4 Hz, 3H), 1.24 (bm, 28H), 1.33–1.35 (m, 2H), 1.45 (m, 2H), 3.29–3.36 (m, 2H), 3.48–3.50 (d, J=5.2 Hz, 2H), 4.04–4.22 (m, 2H), 4.60 (m, 1H), 5.00 (m, 8H), 7.27–7.33 (m, 20H); $^{13}$C (CDCl$_3$) δ 14.05, 18.96, 22.62, 25.95, 29.29, 29.41, 29.49, 29.53, 29.59, 29.63, 31.85, 46.48, 66.58, 69.20, 69.23, 69.28, 69.36, 71.75, 75.37, 127.76, 127.82, 127.86, 127.88, 127.94, 128.36, 128.45, 128.49, 128.61, 128.62, 135.46, 135.54, 135.59, 135.65, 135.68, 135.75, 135.79; MS m/z 866 (M+H)$^+$.

Compound 64

1,2-(3-Dodecyloxypropane)-bis(dibenzylphosphate)

To the pyridine-washed starting dl-3-O-n-dodecyl-1,2-propanediol (61, 400 mg, 1.5 mmol) was added 1H-tetrazole (645 mg, 9.2 mmol). To this mixture was added a 1:1 mixture of freshly distilled THF/CH$_2$Cl$_2$ (40 ml). After 10 mins, dibenzyldiisopropyl phosphoramidate (3.18 gm, 9.2 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and CH$_2$Cl$_2$ were removed under reduced pressure. The concentrate was treated with EtOAc (80 ml), and was washed with Na-metabisulfite (2×35 ml), NaHCO$_3$ (2×40 ml), water (2×30 ml), and brine (2×30 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 100 mg (<10%) of 64 as a clear oil: $^1$H NMR (CDCl$_3$) δ 0.86 (t, J=6.3 Hz, 3H), 1.23 (bm, 18H), 1.46 (m, 2H), 3.13–3.36 (m, 2H), 3.49–3.51 (d, J=5.2 Hz, 214), 4.03–4.23 (m, 2H), 4.59 (m, 1H), 5.01 (m, 8H), 7.26–7.34 (m, 20H); $^{13}$C (CDCl$_3$) δ 14.11, 22.68, 26.01, 29.35, 29.47, 29.54, 29.59, 29.63, 29.66, 31.91, 69.01, 69.06, 69.26, 69.30, 69.34, 69.42, 69.62, 71.83, 77.21, 127.83, 127.89, 127.94, 127.95, 128.44, 128.52, 128.56, 135.64, 135.74, 135.85; IR (NaCl, neat) 3427, 1276, 1000, 885, 499 cm$^{-1}$; MS m/z 781 (M+H)$^+$, m/z 803 (M+Na)$^+$.

Compound 65

1,2-(3-Hexadecyloxypropane)-bis(dibenzylphosphate)

To the pyridine-washed starting dl-3-O-n-hexadecyl-1,2-propanediol (62, 500 mg, 1.57 mmol) was added 1H-tetrazole (664 mg, 9.47 mmol). To this mixture was added a 1:1 mixture of freshly distilled THF/CH$_2$Cl$_2$ (50 ml). After 10 mins, dibenzyldiisopropyl phosphoramidate (3.27 gm, 9.47 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF and CH$_2$Cl$_2$ were removed under reduced pressure. The concentrate was treated with EtOAc (80 ml), and was washed with Na-metabisulfite (2×35 ml), NaHCO$_3$ (2×40 ml), water (2×30 ml), and brine (2×30 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 205 mg (15%) of 65 as a clear oil: $^1$H NMR (CDCl$_3$) δ 0.87 (t, J=6.3 Hz, 3H), 1.25 (bm, 26H), 1.46 (m, 2H), 3.30–3.42 (m, 2H), 3.49–3.51 (d, J=5.2 Hz, 2H), 3.97–4.23 (m, 2H), 4.60 (m, 1H), 5.01 (m, 8H), 7.26–7.35 (m, 20H); $^{13}$C (CDCl$_3$) δ 14.11, 22.68, 26.00, 29.35, 29.47, 29.54, 29.59, 29.64, 29.68, 31.91, 69.00, 69.06, 69.26, 69.29, 69.34, 69.41, 71.82, 71.74, 75.52, 75.60, 77.20, 126.97, 127.82, 127.88, 127.93, 127.95, 127.99, 128.43, 128.51, 128.55, 128.60, 135.63, 135.73, 135.79, 135.83; IR (NaCl, neat) 3423, 1269, 1016, 736, cm$^{-1}$; MS m/z 837 (M+H)$^+$, m/z 859 (M+Na)$^+$.

Example 7

Synthesis of Compounds 66–68

Compound 66

1,2-(3-Octadecyloxypropane)-bis(dihydrogen phosphate)

To a solution of 63 (135 mg, 0.156 mmol) in EtOH (15 ml) was added 10% Pd/C (catalytic amount). Hydrogenation was carried out for 4 hrs at 60 psi. After 4 hours, TLC determined the completion of the reaction, the reaction mixture was filtered through celite, and the eluate was concentrated under reduced pressure to afford 70 mg (89%) of 66 as a clear wax: $^1$H NMR (CD$_3$OD) δ 0.89 (t, J=6.4 Hz, 3H), 1.28 (s, 30H), 1.55 (m, 2H), 3.45–3.50 (m, 2H), 3.62–3.64 (m, 2H), 4.00–4.16 (m, 2H), 4.47 (m, 1H); $^{13}$C NMR (CD$_3$OD) δ 14.43, 19.30, 23.73, 27.20, 30.47, 30.64, 30.78, 33.07, 72.80; MS m/z 503 (M–H)$^-$; IR (NaCl Neat) 1011 cm$^{-1}$.

Compound 67

1,2-(3-Dodecyloxypropane)-bis(dihydrogen phosphate)

To a solution of 64 (70 mg, 0.089 mmol) in EtOH (15 ml) was added 10% Pd/C (catalytic amount). Hydrogenation was carried out for 4 hrs at 60 psi. After 4 hours, TLC determined the completion of the reaction, the reaction mixture was filtered through celite, and the eluate was concentrated under reduced pressure to afford 35 mg (94%) of 67 as a clear wax: $^1$H NMR (CD$_3$OD) δ 0.79 (t, J=6.7 Hz, 3H), 1.90 (s, 18H), 1.46 (m, 2H), 3.34–3.41 (m, 2H), 3.49–3.73 (m, 2H), 3.78–4.05 (m, 2H), 4.47 (m, 1H); $^{13}$C NMR (CD$_3$OD) δ 14.43, 23.71, 23.74, 27.20, 30.49, 30.64, 30.76, 30.81, 33.08, 66.80, 72.79; MS m/z 419 (M–H)$^-$; IR (NaCl Neat) 1008 cm$^{-1}$.

Compound 68

1,2-(3-Hexadecyloxypropane)-bis(dihydrogen phosphate)

To a solution of 65 (138 mg, 0.164 mmol) in EtOH (15 ml) was added 10% Pd/C (catalytic amount). Hydrogenation was carried out for 4 hrs at 60 psi. After 4 hours, TLC determined the completion of the reaction, the reaction mixture was filtered through celite, and the eluate was concentrated under reduced pressure to afford 75 mg (96%) of 68 as a clear wax: $^1$H NMR (CD$_3$OD) δ 0.89 (t, J=6.4 Hz, 3H), 1.28 (s, 23H), 1.56 (m, 2H), 3.43–3.50 (m, 2H), 3.58–3.65 (m, 2H), 3.89–4.16 (m, 2H), 4.47 (m, 1H); $^{13}$C NMR (CD$_3$OD) δ 14.44, 23.74, 27.20, 30.48, 30.64, 30.80, 33.08, 72.80; MS m/z 475 (M–H)$^-$; IR (NaCl Neat) 1011 cm$^{-1}$.

Example 8

Synthesis of Intermediate Compounds 77–84

The glassware used was flame-dried and cooled to room temperature under an argon atmosphere. The starting alcohol was washed with anhydrous pyridine (3 times) and dried on high vacuum for 48 hrs. The reaction was carried out in an argon atmosphere. THF and CH$_2$Cl$_2$ were freshly distilled prior to their use.

Compound 77

1,2-(3-Tetradecanoyloxypropane)-bis(dibenzylphosphate)

To the pyridine-washed starting monomyristine (69, 800 mg, 2.6 mmol) was added 1H-tetrazole (1.01 gm, 14.5 mmol). To this mixture was added freshly distilled THF (45 ml). After 10 mins, dibenzyldiisopropyl phosphoramidate (5.02 gm, 14.5 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×75 ml), water (2×50 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 600 mg (28%) of 77 as a clear oil: $^1$H NMR (CDCl$_3$) δ 0.87 (t, J=6.3 Hz, 3H), 1.25 (bm, 20H), 1.53 (m, 2H), 2.17–2.32 (m, 2H), 3.96–4.24 (m, 4H), 4.61–4.70 (m, 1H), 4.99–5.08 (m, 8H), 7.29–7.35 (m, 20H); $^{13}$C (CDCl$_3$) δ 14.10, 22.67, 24.70, 29.08, 29.23, 29.33, 29.44, 29.59, 29.62, 29.66, 31.90, 33.86, 64.24, 65.82, 69.41, 69.46, 69.48, 69.53, 69.57, 77.20, 127.85, 127.91, 127.98, 127.99, 128.04, 128.57, 128.59, 128.70, 128.71 135.50, 135.59, 173.09; IR (NaCl, Neat) 3422, 1742, 1457, 1274, 1035, 1001 cm$^{-1}$; MS m/z 8823 (M+H)$^+$, m/z 845 (M+Na)$^+$.

Compound 78

1,2-(3-Pentadecanoyloxypropane)-bis(dibenzylphosphate)

To the pyridine-washed starting monopentadecanoin (70, 800 mg, 2.5 mmol) was added 1H-tetrazole (970 mg, 13.9 mmol). To this mixture was added freshly distilled THF (45 ml). After 10 mins, dibenzyldiisopropyl phosphoramidate (4.80 gm, 13.9 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×100 ml), water (2×50 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 741 mg (35%) of 78 as a clear oil: $^1$H NMR (CDCl$_3$) δ 0.87 (t, J=6.4 Hz, 3H), 1.25 (bm, 22H), 1.53 (m, 2H), 2.17–2.32 (m, 2H), 3.95–4.24 (m, 4H), 4.61–4.70 (m, 1H), 4.99–5.07 (m, 8H), 7.29–7.35 (m, 20H); $^{13}$C (CDCl$_3$) δ 14.09, 22.66, 24.69, 29.08, 29.23, 29.33, 29.44, 29.59, 29.62, 29.65, 31.89, 33.85, 64.23, 65.86, 69.40, 69.46, 69.48, 69.53, 69.56, 77.20, 127.84, 127.90, 127.97, 127.98, 128.03, 128.56, 128.59, 128.69, 128.71 135.50, 135.59, 173.09; IR (NaCl, Neat) 3421, 1742, 1457, 1275, 1035, 1014, 1001 cm$^{-1}$; MS m/z 837 (M+H)$^+$, m/z 859 (M+Na)$^+$.

Compound 79

1,2-(3-Hexadecanoyloxypropane)-bis(dibenzylphosphate)

To the pyridine-washed starting monopalmitin (71, 800 mg, 2.4 mmol) was added 1H-tetrazole (1.00 gm, 14.2 mmol). To this mixture was added freshly distilled THF (45 ml). After 10 mins, dibenzyldiisopropyl phosphoramidate (4.90 gm, 14.2 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×100 ml), water (2×50 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 786 mg (38%) of 79 as a clear oil: $^1$H NMR (CDCl$_3$) δ 0.87 (t, J=6.4 Hz, 3H), 1.25 (bm, 24H), 1.53 (m, 2H), 2.17–2.32 (m, 2H), 3.96–4.24 (m, 4H), 4.61–4.70 (m, 1H), 4.99–5.08 (m, 8H), 7.29–7.35 (m, 20H); $^{13}$C (CDCl$_3$) δ 14.09, 22.66, 24.71, 29.09, 29.23, 29.33, 29.45, 29.60, 29.63, 29.67, 31.90, 33.87, 62.23, 62.30, 65.89, 69.43, 69.48, 69.50, 69.55, 69.58, 77.20, 126.96, 127.85, 127.91, 127.98, 128.04, 128.56, 128.59, 128.64, 128.71 135.52, 135.61, 173.07; IR (NaCl, Neat) 3421, 1742, 1457, 1273, 1035, 1016, 1001 cm$^{-1}$; MS m/z 851 (M+H)$^+$, m/z 873 (M+Na)$^+$.

Compound 80

1,2-(3-Heptadecanoyloxypropane)-bis(dibenzylphosphate)

To the pyridine-washed starting monoheptadecanoin (72, 800 mg, 2.32 mmol) was added 1H-tetrazole (980 mg, 13.9 mmol). To this mixture was added freshly distilled THF (40 ml). After 10 mins, dibenzyldiisopropyl phosphoramidate (4.81 gm, 13.9 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×100 ml), water (2×50 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 1.48 gm (74%) of 80 as a clear oil: $^1$H NMR (CDCl$_3$) δ 0.87 (t, J=6.4 Hz, 3H), 1.23–1.25 (bm, 26H), 1.53 (m, 2H), 2.20 (t, J=7.1 Hz, 2H), 4.02–4.24 (m, 4H), 4.66 (m, 1H), 4.99–5.05 (m, 8H), 7.29–7.35 (m, 20H); $^{13}$C (CDCl$_3$) δ 14.10, 22.66, 24.69, 29.07, 29.23, 29.33, 29.44, 29.59, 29.63, 29.66, 31.89, 33.84, 62.21, 62.27, 65.85, 69.40, 69.45, 69.47, 69.52, 69.56, 74.04, 74.23, 77.20, 127.83, 127.87, 127.96, 127.97, 128.53, 128.55, 128.57, 128.59, 135.47, 135.56, 173.07; IR (NaCl, Neat) 3483, 1743, 1457, 1281, 1035, 1013, 1000 cm$^{-1}$; MS m/z 865 (M+H)$^+$, m/z 887 (M+Na)$^+$.

Compound 81

1,2-(3-Octadecanoyloxypropane)-bis (dibenzylphosphate)

To the pyridine-washed starting monostearine (73, 800 mg, 2.2 mmol) was added 1H-tetrazole (1.00 gm, 14.2 mmol). To this mixture was added freshly distilled THF (40 ml). After 10 mins, dibenzyldiisopropyl phosphoramidate (4.92 gm, 14.2 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×100 ml), water (2×50 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 870 mg (45%) of 81 as a clear oil: $^1$H NMR (CDCl$_3$) δ 0.87 (t, J=6.4 Hz, 3H), 1.23–1.25 (bm, 28H), 1.53 (m, 2H), 2.20 (t, J=7.2 Hz, 2H), 3.97–4.24 (m, 4H), 4.66 (m, 1H), 4.99–5.07 (m, 8H), 7.29–7.35 (m, 20H); $^{13}$C (CDCl$_3$) δ 14.09, 22.66, 24.69, 29.08, 29.23, 29.33, 29.45, 29.59, 29.63, 29.67, 31.89, 33.85, 62.22, 62.28, 64.23, 65.87, 68.69, 69.23, 69.42, 69.50, 69.54, 69.58, 74.07, 74.25, 127.60, 127.84, 127.90, 127.98, 128.03, 128.54, 128.56, 128.58, 128.60, 128.71, 135.47, 135.57, 173.08; IR (NaCl, Neat) 3421, 1742, 1457, 1273, 1251, 1216, 1035, 1016, 1000 cm$^{-1}$; MS m/z 879 (M+H)$^+$, m/z 901 (M+Na)$^+$.

Compound 82

1,2-(3-Nonadecanoyloxypropane)-bis (dibenzylphosphate)

To the pyridine-washed starting Monononadecanoin (74, 800 mg, 2.1 mmol) was added 1H-tetrazole (977 gm, 13.9 mmol). To this mixture was added freshly distilled THF (40 ml). After 10 mins, dibenzyldiisopropyl phosphoramidate (4.81 gm, 13.9 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×125 ml), water (2×75 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 1.47 gm (78%) of 82 as a clear oil: $^1$H NMR (CDCl$_3$) δ 0.87 (t, J=6.3 Hz, 3H), 1.23–1.25 (bm, 30H), 1.53 (m, 2H), 2.20 (t, J=7.2 Hz, 2H), 4.02–4.24 (m, 4H), 4.66 (m, 1H), 4.99–5.03 (m, 8H), 7.29–7.36 (m, 20H); $^{13}$C (CDCl$_3$) δ 14.08, 22.65, 24.67, 29.06, 29.22, 29.32, 29.43, 29.58, 29.61, 29.66, 31.88, 33.83, 62.25, 65.84, 69.38, 69.46, 69.51, 69.54, 74.03, 74.10, 74.15, 74.22, 77.20, 127.82, 127.88, 127.96, 128.53, 128.56, 135.45, 135.55, 173.06; IR (NaCl, Neat) 3483, 1743, 1457, 1273, 1282, 1216, 1035, 1013 cm$^{-1}$; MS m/z 893 (M+H)$^+$, m/z 915 (M+Na)$^+$.

Compound 83

1,2-(3-icosanoyloxypropane)-bis(dibenzylphosphate)

To the pyridine-washed starting Monoarachidin (75, 800 mg, 2.06 mmol) was added 1H-tetrazole (1.00 gm, 14.2 mmol). To this mixture was added freshly distilled THF (40 ml). After 10 mins, dibenzyldiisopropyl phosphoramidate (4.92 gm, 14.2 mmol) was added, and the reaction was stirred under an argon atmosphere for 90 mins. The TLC of the reaction mixture showed the formation of the product. This mixture was cooled to 0° C. (ice bath), and a large excess of peracetic acid was added. The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×125 ml), water (2×75 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 1.39 gm (74%) of 83 as a clear oil: $^1$H NMR (CDCl$_3$) δ 0.87 (t, J=6.4 Hz, 3H), 1.23–1.25 (bm, 32H), 1.53 (m, 2H), 2.20 (t, J=7.2 Hz, 2H), 4.02–4.24 (m, 4H), 4.66 (m, 1H), 4.99–5.05 (m, 8H), 7.29–7.36 (m, 20H); $^{13}$C (CDCl$_3$) δ 14.09, 22.65, 24.69, 29.07, 29.23, 29.33, 29.44, 29.59, 29.63, 29.67, 31.89, 33.84, 62.21, 62.27, 65.86, 69.40, 69.45, 69.48, 69.52, 69.56, 74.05, 74.12, 74.16, 74.24, 77.20, 127.83, 127.89, 127.97, 128.53, 128.55, 128.57, 128.59, 135.47, 135.56, 173.07; IR (NaCl, Neat) 3483, 1743, 1457, 1273, 1282, 1216, 1035, 1012, 1000 cm$^{-1}$; MS m/z 907 (M+H)$^+$, m/z 929 (M+Na)$^+$.

Compound 84

1,2-(3-Docosanoyloxypropane)-bis (dibenzylphosphate)

To the pyridine-washed starting Monobehenin (76, 800 mg, 1.92 mmol) was added 1H-tetrazole (1.00 gm, 14.2 mmol). To this mixture was added freshly distilled THF (40 ml). After 10 mins, dibenzyldiisopropyl phosphoramidate (5.14 gm, 14.8 mmol) was added, and the reaction was stirred under an argon atmosphere for 90 mins. The TLC of the reaction mixture showed the formation of the product. This mixture was cooled to 0° C. (ice bath), and a large excess of peracetic acid was added.

The mixture was stirred for another 35 mins, followed by the addition of Na-metabisulfite to quench the excess peracetic acid. The THF was removed under reduced pressure. The concentrate was treated with EtOAc (100 ml), and was washed with Na-metabisulfite (2×50 ml), NaHCO$_3$ (2×125 ml), water (2×75 ml), and brine (2×50 ml). The organic portion was dried over NaSO$_4$, and concentrated under reduced pressure. The residue was subjected to flash column chromatography, eluting with EtOAc/hexanes of various compositions.

Appropriate fractions were pooled, and concentrated to dryness in vacuo to afford 1.27 gm (71%) of 84 as a white wax like compound: $^1$H NMR (CDCl$_3$) δ 0.87 (t, J=6.4 Hz, 3H), 1.23–1.25 (bm, 36H), 1.53 (m, 2H), 2.20 (t, J=7.2 Hz, 2H), 4.02–4.24 (m, 4H), 4.66 (m, 1H), 4.99–5.03 (m, 8H), 7.29–7.36 (m, 20H); $^{13}$C (CDCl$_3$) δ 14.08, 22.65, 24.68, 29.07, 29.22, 29.32, 29.44, 29.59, 29.62, 29.66, 31.88, 33.84, 62.20, 62.26, 65.85, 69.40, 69.45, 69.48, 69.53, 69.57, 74.05, 74.16, m 74.24, 77.20, 127.83, 127.88, 127.96, 127.97, 128.30, 128.52, 128.54, 128.57, 128.58, 135.46, 135.55, 173.07; MS m/z 935 (M+H)$^+$, m/z 957 (M+Na)$^+$.

Example 9

Synthesis of Compounds 85–92

Compound 85

1,2-(3-Tetradecanoyloxypropane)-bis(dihydrogen phosphate)

To a solution of 77 (385 mg, 0.468 mmol) in EtOH (15 ml) was added 10% Pd/C (catalytic amount). Hydrogenation was carried out for 4 hrs at 60 psi. After 4 hours, TLC determined the completion of the reaction, the reaction mixture was filtered through celite, and the eluate was concentrated under reduced pressure to afford 210 mg (98%) of 85 as a white wax: $^1$H NMR (CD$_3$OD) δ 0.89 (t, J=6.4 Hz, 3H), 1.28 (s, 20H), 1.56–1.63 (m, 2H), 2.24–2.38 (m, 2H), 3.93–4.42 (m, 4H), 4.59 (m, 1H); $^{13}$C NMR (CD$_3$OD) δ 14.44, 23.73, 26.09, 30.71, 30.23, 30.43, 30.47, 30.61, 30.75, 33.07, 34.80, 34.94, 61.90 61.96, 63.96, 63.70, 66.24, 74.33, 77.51, 175.02; MS m/z 461 (M–H)$^-$; IR (NaCl Neat) 3386, 1702, 1216, 1019 cm$^{-1}$.

Compound 86

1,2-(3-Pentadecanoyloxypropane)-bis(dihydrogen phosphate)

To a solution of 78 (451 mg, 0.538 mmol) in EtOH (15 ml) was added 10% Pd/C (catalytic amount). Hydrogenation was carried out for 4 hrs at 60 psi. After 4 hours, TLC determined the completion of the reaction, the reaction mixture was filtered through celite, and the eluate was concentrated under reduced pressure to afford 250 mg (97%) of 86 as a white wax: $^1$H NMR (CD$_3$OD) δ 0.89 (t, J=6.4 Hz, 3H), 1.28 (s, 22H), 1.58 (m, 2H), 2.24–2.38 (m, 2H), 3.97–4.21 (m, 4H), 4.38 (m, 1H); $^{13}$C NMR (CD$_3$OD) δ 14.44, 23.74, 26.05, 30.16, 30.36, 30.48, 30.57, 30.76, 33.08, 35.11, 61.36, 63.70, 63.90 66.24, 67.77, 70.22, 77.33, 77.40, 77.51, 175.63; MS m/z 475 (M–H)$^-$; IR (NaCl Neat) 3380, 1728, 1216, 1031 cm$^{-1}$.

Compound 87

1,2-(3-Hexadecanoyloxypropane)-bis(dihydrogen phosphate)

To a solution of 79 (561 mg, 0.659 mmol) in EtOH (15 ml) was added 10% Pd/C (610 mg). Hydrogenation was carried out for 4 hrs at 60 psi. After 4 hours, TLC determined the completion of the reaction, the reaction mixture was filtered through celite, and the eluate was concentrated under reduced pressure to afford 300 mg (92%) of 87 as a white wax: $^1$H NMR (CD$_3$OD) δ 0.89 (t, J=6.4 Hz, 3H), 1.28 (s, 24H), 1.56–1.63 (m, 2H), 2.24–2.38 (m, 2H), 3.95–4.40 (m, 4H), 4.39 (m, 1H); $^{13}$C NMR (CD$_3$OD) δ 14.43, 23.73, 25.89, 26.05, 26.09, 30.15, 30.23, 30.36, 30.44, 30.47, 30.56, 30.61, 30.67, 30.75, 33.07, 34.08, 34.94, 35.11, 61.36, 64.00, 66.22, 67.74, 70.22, 77.33, 77.40, 77.51, 175.03; MS m/z 489 (M–H)$^-$; IR (NaCl Neat) 3357, 1729, 1216, 1029 cm$^{-1}$.

Compound 88

1,2-(3-Heptadecanoyloxypropane)-bis(dihydrogen phosphate)

To a solution of 80 (636 mg, 0.736 mmol) in EtOH (15 ml) was added 10% Pd/C (724 mg). Hydrogenation was carried out for 4 hrs at 60 psi. After 4 hours, TLC determined the completion of the reaction, the reaction mixture was filtered through celite, and the eluate was concentrated under reduced pressure to afford 365 mg (98%) of 88 as a white wax: $^1$H NMR (CD$_3$OD) δ 0.89 (t, J=6.6 Hz, 3H), 1.28 (s, 26H), 1.56–1.63 (m, 2H), 3.96–4.17 (m, 4H), 4.22–4.42 (m, 1H); $^{13}$C NMR (CD$_3$OD) δ 14.54, 23.73, 25.90, 26.10, 30.16, 30.24, 30.36, 30.43, 30.47, 30.56, 30.61, 30.76, 33.07, 34.81, 34.95, 61.37, 61.92, 63.97, 66.26, 67.70, 67.78, 70.06, 74.42, 77.46, 175.04; MS m/z 503 (M–H)$^-$; IR (NaCl Neat) 3357, 1710, 1216, 1032 cm$^{-1}$; Anal. Calcd. for C$_{20}$H$_{42}$O$_{10}$P$_2$·1H$_2$O: C, 45.97; H, 8.49. Found: C, 46.32; H, 8.73.

Compound 89

1,2-(3-Octadecanoyloxypropane)-bis(dihydrogen phosphate)

To a solution of 81 (530 mg, 0.603 mmol) in EtOH (15 ml) was added 10% Pd/C (617 mg). Hydrogenation was carried out for 4 hrs at 60 psi. After 4 hours, TLC determined the completion of the reaction, the reaction mixture was filtered through celite, and the eluate was concentrated under reduced pressure to afford 305 mg (97%) of 89 as a white wax: $^1$H NMR (CD$_3$OD) δ 0.89 (t, j=6.3 Hz, 3H), 1.28 (s, 28H), 1.56–1.61 (m, 2H), 2.42–2.38 (m, 2H), 3.91–4.17 (m, 4H), 4.24–4.42 9 m, 1H); $^{13}$C NMR (CD$_3$OD) δ 14.43, 23.74, 25.90, 26.06, 26.10, 30.16, 30.24, 30.36, 30.47, 30.57, 30.61, 30.67, 30.76, 33.08, 34.81, 34.95, 35.11, 61.37, 63.72, 66.26, 67.68, 67.75, 70.25, 77.48, 175.04; MS m/z 517 (M–H)$^-$; IR (NaCl Neat) 3388, 1731, 1216, 1020 cm$^{-1}$.

Compound 90

1,2-(3-Nonadecanoyloxypropane)-bis(dihydrogen phosphate)

To a solution of 82 (952 mg, 1.06 mmol) in EtOH (25 ml) was added 10% Pd/C (1.00 gm). Hydrogenation was carried out for 4 hrs at 60 psi. After 4 hours TLC determined the completion of the reaction, the reaction mixture was filtered through celite, and the eluate was concentrated under reduced pressure to afford 555 mg (98%) of 90 as a white wax: $^1$H NMR (CD$_3$OD) δ 0.89 (t, J=6.4 Hz, 3H), 1.27 (s, 29H), 1.56–1.63 (m, 2H), 2.24–2.38 (m, 2H), 4.06–4.17 (m, 2H), 4.22–4.42 (m, 2H), 4.59 (m, 1H); $^{13}$C NMR (CD$_3$OD) δ 14.44, 23.74, 25.90, 26.06, 30.16, 30.24, 30.36, 30.48, 30.57, 30.63, 30.76, 30.79, 33.08, 34.81, 35.12, 63.94, 66.25, 175.03; MS m/z 531 (M−H)$^−$; IR (NaCl Neat) 1735, 1216, 1012 cm$^{-1}$.

Compound 91

1,2-(3-Icosanoyloxypropane)-bis(dihydrogen phosphate)

To a solution of 83 (711 mg, 0.784 mmol) in EtOH (25 ml) was added 10% Pd/C (813 mg). Hydrogenation was carried out for 4 hrs at 60 psi. After 4 hours TLC determined the completion of the reaction, the reaction mixture was filtered through celite, and the eluate was concentrated under reduced pressure to afford 419 mg (97%) of 91 as a white wax: $^1$H NMR (CD$_3$OD) δ 0.89 (t, J=6.4 Hz, 3H), 1.28 (s, 32H), 1.58 (m, 2H), 2.24–2.38 (m, 2H), 3.95–4.42 (m, 4H), 4.58 (m, 1H); $^{13}$C NMR (CD$_3$OD) δ 14.44, 23.74, 25.90, 26.06, 30.16, 30.24, 30.36, 30.48, 30.57, 30.63, 30.67, 30.76, 33.08, 34.81, 35.11, 61.37, 61.98, 66.26, 67.69, 67.77, 77.42, 175.03; MS m/z 545 (M−H)$^−$; IR (NaCl Neat) 3418, 1735, 1261, 1019 cm$^{-1}$.

Compound 92

1,2-(3-Docosanoyloxypropane)-bis(dihydrogen phosphate)

To a solution of 84 (663 mg, 0.709 mmol) in EtOH (25 ml) was added 10% Pd/C (710 mg). Hydrogenation was carried out for 4 hrs at 60 psi. After 4 hours TLC determined the completion of the reaction, the reaction mixture was filtered through celite, and the eluate was concentrated under reduced pressure to afford 400 mg (98%) of 92 as a white wax: $^1$H NMR (CD$_3$OD) δ 0.89 (t, J=6.3 Hz, 3H), 1.27 (s, 36H), 1.58 (m, 2H), 2.24–2.38 (m, 2H), 3.98–4.42 (m, 4H), 4.59 (m, 1H); $^{13}$C NMR (CDCl$_3$/CD$_3$OD) δ 13.72, 22.40, 24.71, 28.84, 28.97, 29.08, 29.18, 29.41, 31.65, 34.1660.15, 60.99, 62.42, 63.17, 65.16, 65.30, 65.98, 73.24, 173,79; MS m/z 573 (M−H)$^−$; IR (NaCl Neat) 3431, 1739, 1254, 1177 cm$^{-1}$.

Example 10

Xenopus Oocyte Assay

Xenopus oocytes which endogenously express PSP24 PLGFR were used to screen the newly designed and synthesized compounds for their LPA inhibitory activity.

Oocytes were obtained from xylazine-anesthetized adult Xenopus laevis frogs (Carolina Scientific, Burlington, N.C.) under aseptic conditions and prepared for experiment. Stage V–VI oocytes were denuded of the the follicular cell layer with type A collagenase treatment (Boehringer, Ind.) at 1.4 mg/ml in a Ca$^{2+}$-free ovarian Ringers-2 solution ((OR-2) 82.5 mM NaCl, 2 mM KCl, 1 mM MgCl$_2$, 5 mM HEPES, pH 7.5, with NaOH). Oocytes were kept in Barth's solution in an incubator between 17–20° C. and were used for 2–7 days after isolation.

Electrophysiological recordings were carried out using a standard two-electrode voltage-clamp amplifier holding the membrane potential at −60 mV (GeneClamp 500, Axon Instruments, Calif.). Test compounds were dissolved in MeOH, complexed with fatty acid free BSA, and diluted with frog Na$^+$-Ringers solution (120 nM NaCl, 2 mM KCl, 1.8 mM CaCl$_2$, 5 mM HEPES; pH 7.0), which were applied through superfusion to the oocyte at a flow rate of 5 ml/min. Membrane currents were recorded with a NIC-310 digital oscilloscope (Nicolet, Madison, Wis.). Applications were made at intervals of 15 mins (minimum) to allow for the appropriate washout and recovery from desensitization.

FIGS. 21–27 show the dose-dependent inhibition of LPA-induced chloride currents by compounds 56, 57, 66, and 92.

Compound 36 was the best inhibitor among the non-phosphorylated derivatives. When compound 36 was injected intracellularly to see whether its inhibitory effects were a result of its actions on the cell surface or whether the inhibition was a result of its actions within the cell, this intracellular application of 36 did not give any information as to its site of action. Hence, moving away from free hydroxy compounds (35–43), phosphorylated compounds (55–59) were synthesized to interact on the cell surface and to prevent the compounds from penetrating into the cell.

Figure 24:
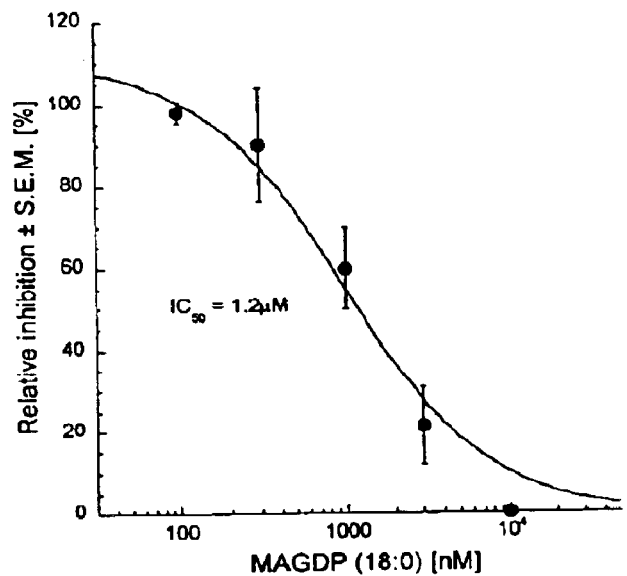
FIG. 24 is a graph illustrating dose-inhibitory effect of 66 (MAGDP, 18:0). A constant amount of LPA (5 nM) was applied to oocytes together with increasing amounts of 66. Data points represent the peak amplitude of the measured chloride currents.
Figure 25:
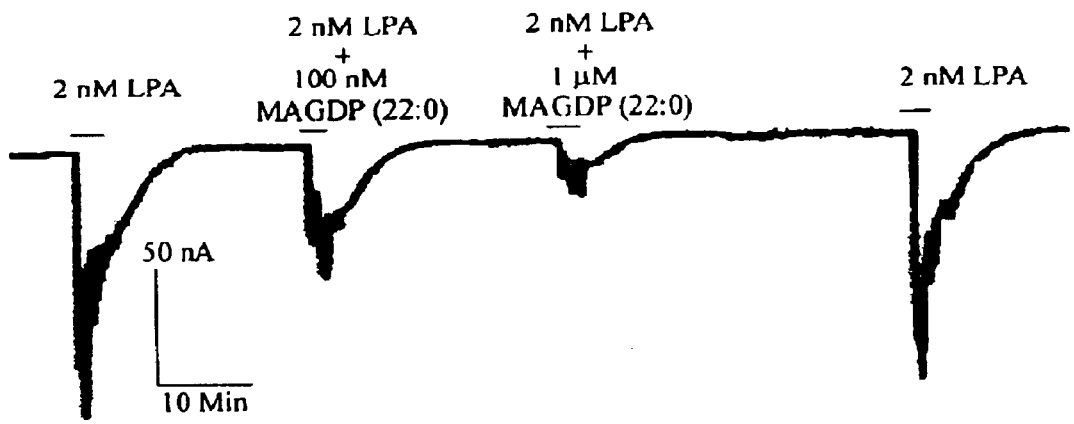
FIG. 25 is a graph illustrating the dose-dependent inhibition of LPA-induced chloride currents in *Xenopus* oocytes by extracellular application of 92 (MAGDP, 22:0).
Figure 26:
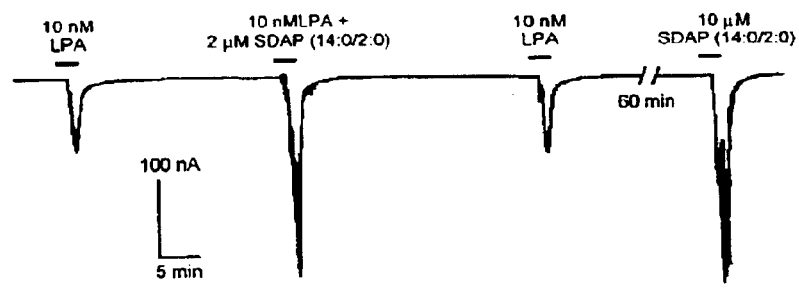
FIG. 26 is a graph illustrating the dose-dependent effect of 56a (SDAP, 14:0/2:0) on *Xenopus* oocytes.

Compounds 56, 57, 66, and 92 were inhibitors of LPA-induced chloride current in Xenopus oocyte. Compounds 56, 57, 66, and 92 were able to block the actions of LPA in a dose-dependent fashion. Moreover, washing the the Xenopus oocyte, there was a complete recovery of the LPA response; that experiment implies that compounds 56, 57, 66, 92 were able to inhibit the LPA-induced chloride currents in a reversible fashion. Compound 66 at 5 µM completely abolished the effect of LPA in Xenopus oocytes, with an IC$_{50}$ of about 1.2 µM (FIGS. 23 and 24). Moreover, when 66 was microinjected inside the cell (arrow, FIG. 23B), followed by the extracellular application of LPA (10 nM), it failed to inhibit the LPA response; that experiment suggests that the inhibitory actions of compound 66 were of an extracellular nature.

Compounds 35, and 37–43 were tested on Xenopus oocytes, but the results were inconclusive. Compound 55 at 1 µM showed slight inhibition (38% against 2 nM LPA). In the SAP series, compounds 58 and 59 remain to be tested in the Xenopus oocyte assay. In the bisphosphate series, compound 89 inhibited the LPA-induced response (59% against 2 nM LPA). However, compounds 67 (threshold ~1 µM), 68 (threshold ~10 nM), and 85 (threshold~100 nM) were able to elicit a response alone; compounds 86, 87, 88, 90, and 91 have yet to be evaluated. Compound 56a was designed and synthesized to test the importance of the free amino group. When 56a was evaluated in the Xenopus oocyte assay, 56a enhanced the LPA response when applied in combination with LPA. Compound 56a did not elicit a response at 2 µM (not shown), but at 10 µM, 56a was able to elicit a response on its own (FIG. 26); that experiment suggests, that a free amino group is necessary for the inhibitory activity.

Example 11

HEY Ovarian Cells Migrations

It is known that two LPA receptors, EDG-2 and EDG-7, are expressed in HEY ovarian cancer cells, so compounds 56, 56a, and 66 were evaluated for their ablity to inhibit LPA-induced cell motility (compound conc: 1 µM against 0.1 µM LPA conc:).

HEY ovarian cells were maintained in RPMI 1640 medium with 2 mM L-glutamine (GIBCO BRL) supplemented with 10% fetal bovine serum (FBS, Hyclone). All cells were synchronized to the $G_o/G_1$ stage by growing them to confluency for 2 days. The cells were replated and harvested for experiments when cells were about 50–60% confluent on the flask. After removal of the cells from the flask, they were exposed for 5 min to 0.53 mM EDTA in PBS at 37° C. EDTA was neutralized with equal volume of RPMI 1640 plus 2 mM L-glutamine and 10% FBS. Cells were centrifuged at 800 rpm for 10 min at room temperature. Harvested cells were washed twice with RPMI 1640 with 2 mM L-glutamine medium and resuspended in the concentration of $1 \times 10^6$ cells/ml, and then rested for 1 hr at 37° C.

A modified quantitative cell migration assay (Cat. # ECM500 from Chemicon, Temecula, Calif.) was used to test cell motility. The Chemicon chamber membrane was coated with fibronectin-containing pores of 8 microns in diameter. A 400 μl RPMI/2 mM L-glutamine containing either no inhibitors or inhibitors (1 μM) were pippetted into the lower chamber. About $5 \times 10^4$ cells in RPMI 1640/2 mM L-glutamine were added to the top chamber. The 24-well plates with inserts were incubated for 4 hours in a 5% $CO_2$ incubator at 37° C. At the end of incubation, the chambers were removed to a fresh 24-well plate, and the cells on the inside chamber were removed by a swab several times and placed in the prepared Cell Stain Solution for 30 minutes at room temperature. At the end of incubation, Cell Stain Solution was removed from the wells. The chambers were washed 3 times with 1 mL PBS per well. After the final PBS wash, the chambers were examined to confirm proper cell morphology, and adherent cells were counted using an inverted microscope.

Figure 27:
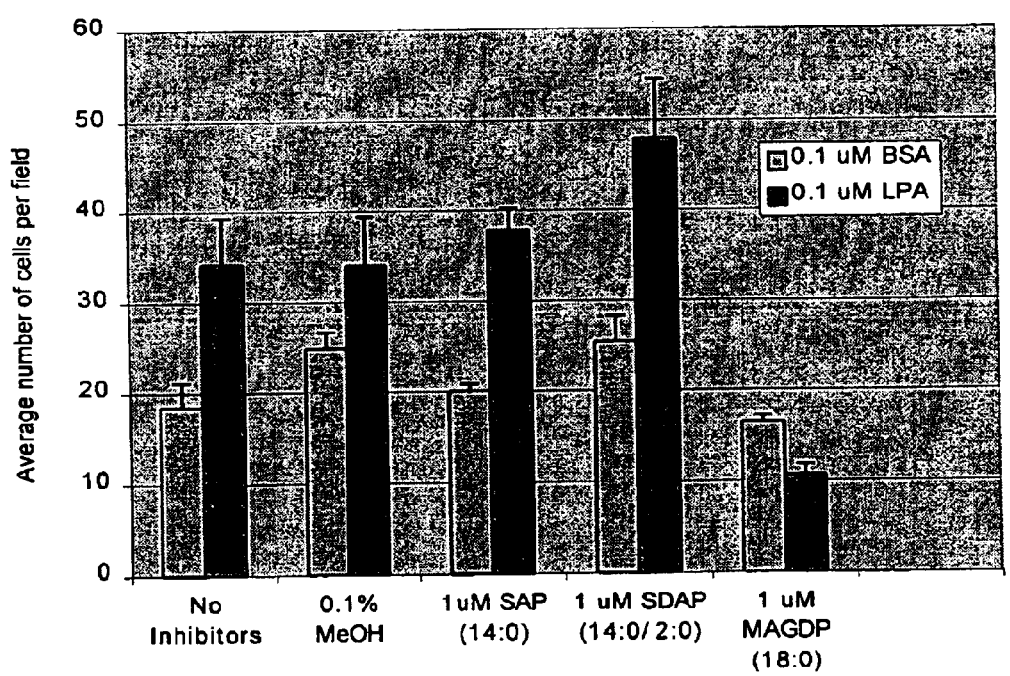
FIG. 27 is a bar graph depicting the effects of compounds 56 (SAP, 14:0), 56a (SDAP, 14:0/2:0), and 66 (MAGDP, 18:0) on LPA-induced HEY cell migration. Test compound concentration was 1 μM; LPA concentration was 0.1 μM.

An effect of the newly synthesized compounds on the LPA-induced migration of HEY ovarian cancer cell is shown in FIG. 27. Compound 66 inhibited the LPA-induced cell motility by about 70%; however, compound 55 (marginally) and 56a potentiated the LPA-induced cell motility.

Example 12

Compound Cytotoxicity

Im et al. (2000) and RT-PCR data showed the presence of PLGFR's in prostate cancer cell lines DU-145, PC-3, and LNCaP. Due to the promising inhibitory activity in *Xenopus* oocyte and the cell motility assay, the growth inhibitory effects of a number of compounds on DU-145, PC-3, and LNCaP prostate cancer cell lines were examined.

DU-145, PC-3, and LNCaP cells were propagated in 150 $cm^2$ flasks, containing RPMI-1640 or Dulbecco's modified Eagle media supplemented with 10% fetal bovine serum (FBS). Cells were removed from stock flasks using trypsin, centrifuged, resuspended in fresh media, and plated at a density of approximately 2,000 cells/well in 96-well culture plates. Final drug concentrations ranged from 0.05 to either 10 or 50 μM. Control experiments with no drug added (negative control) and 5-fluorouracil added (positive control) were performed in parallel. Media was removed and replaced at 48 hours to minimize the effects of drug degradation during the course of the experiment. After 96 hours drug exposure, cells were fixed by the addition of cold 50% trichloroacetic acid (TCA) and incubation at 4° C. for 1 hour. Fixed cells were stained with sulforhodamine B (SRB), and cell number was determined by comparison of absorbance at 540 nm, as compared to a standard curve of cell number versus absorbance. Experiments were performed in duplicate. Cell number as a percentage of control (untreated wells) was plotted versus drug concentration and the concentration that inhibited cell growth by 50% ($IC_{50}$) determined by nonlinear regression (WinNonlin, Pharsight Corporation).

Cytotoxicity studies performed on prostate cancer cell lines DU-145, PC-3, and LNCaP, together with the reference compounds 5F-uracil, LPA (18:1), SPH (13:0), SPP (13:0), and N-palmitoyl L-serine phosphoric acid (15:0), are shown in Table 3 below.

TABLE 3

Cytotoxicity of Synthesized Compounds on Prostate Cancer Cell Lines

| | $IC_{50} \pm SEM\ (\mu M)^x$ | | |
|---|---|---|---|
| Compound | DU145 | PC-3 | LNCaP |
| Fluorouracil | 6.8 ± 3.3 | 10.2 ± 4.1 | 2.8 ± 1.6 |
| LPA (18:1) | WA | 28.5 ± 6.3 | WA |
| SPP (13:0) | >10 | WA | NA |
| SPH (13:0) | 13.9 ± 1.1 | 11.7 ± 2.3 | 5.7 ± 2.1 |
| N-palmitoyl-L-serine (15:0) | WA | WA | WA |
| 27 | 19.7 ± 6.0 | WA | 10.9 ± 2.7 |
| 38 | 38.9 ± 8.9 | ? | ? |
| 51 | 8.1 ± 1.3 | 25.4 ± 3.6 | 19.9 ± 6.4 |
| 55 | 24.9 ± 4.1 | 31.6 ± 9.0 | 4.9 ± 2.6 |
| 56 | 2.3 ± 1.2 | 0.7 ± 0.1 | 13.5 ± 4.7 |
| 56a | 0.7 ± 0.1 | WA | 30.3 ± 7.9 |
| 57 | 9.1 ± 0.8 | WA | 10.7 ± 2.1 |
| 66 | NA | NA | 3.1 ± 3.2 |
| 67 | WA | WA | 25.2 ± 12.3 |
| 68 | WA | WA | 29.3 ± 21.7 |
| 85 | NA | NA | 11.6 ± 10.3 |
| 86 | NA | NA | ? |
| 87 | NA | NA | WA |
| 88 | NA | NA | ? |
| 89 | WA | NA | ? |
| 90 | >50 | WA | WA |
| 91 | 42.2 ± 1.9 | WA | WA |
| 92 | WA | WA | WA |

$^x$Cell number as a percentage of control (untreated wells) was plotted versus drug concentration and the concentration that inhibited cell growth by 50% ($IC_{50}$) determined by nonlinear regression (WinNonlin, Pharsight Corporation).
WA = Weak Activity; NA = No Activity; ? = Maximum inhibition was 50%.

Compounds 55, 56, 56a, 66, and 85 exhibited a range of growth inhibitory activities. Compound 56 was a more potent inhibitor of DU-145 and PC-3 cell growth than 5-fluorouracil. Interestingly, 56a selectively inhibited DU-145 cell growth, but was less potent against PC-3 cells; compound 55 was a more potent inhibitor of LNCaP cell growth as against DU-145 and PC-3 cells. Compound 66 selectively inhibited LNCaP cell growth, but showed no activity on PC-3 and LNCaP cells. Compound 85 was the most active among the bisphosphates (sn-1 acyl).

Discussion of Examples 1–12

Three sets of compounds were specifically synthesized and analyzed (35–43, 55–59, 66–68, and 85–92). The first and the second sets involve the amalgamation of the endogenous inhibitors SPH and SPP with the synthetic inhibitor N-palmitoyl L-serine phosphoric acid, whereas the third series involves the bisphosphates. Compounds 56, 57, 66 and 92 were inhibitors of LPA-induced chloride currents in the *Xenopus* oocyte assay. Also, bisphosphates with shorter chain length at (sn-1) position were able to elicit chloride currents in *Xenopus* oocyte [67 (threshold ~1 μM), 68 (threshold ~10 nM), and 85 (threshold ~100 nM)]. Compound 66 was shown to inhibit the LPA-induced cell motility in HEY ovarian cancer cell lines. On evaluating the growth inhibitory effects of the above-synthesized compounds on DU-145, PC-3, and LNCaP prostate cancer cell lines, three highly potent and selective compounds (56, 56a, and 66) were discovered.

The above data (Table 3) suggests that (i) compounds that contain an alcohol with no phosphate are less active (27 vs.

56), (ii) compounds with the protected phosphate moiety are less active (51 vs. 56), (iii) alkylation of the amine does not reduce activity (56a), (iv) the most potent bisphosphate has an ether linkage at the sn-1 position, (v) decreasing the chain length in the SAP series (55 vs. 56) decreased the potency towards DU-145 and PC-3 (however, it was more potent against LNCaP cells), (vi) on decreasing the chain length for the bisphosphate (sn-1 alkyl) compounds, potency decreased, though selectivity towards LNCaP cell remained, and (vii) substitution at sn-1 position (acyl vs alkyl) did not increase the potency. The target site for these molecules is likely on the cell membrane (e.g., a membrane-spanning receptor), because the polar phosphate derivatives are unlikely to easily cross the cell membrane (although there exists the possibility that an active transport system could exist). These results suggest that differences in PLGFR's or downstream signal transduction events may play a significant role in the growth inhibitory properties of these compounds in prostate cancer cells.

Example 13

Preparation and Characterization of Stable Cell Lines Expressing Edg-2, Edg-4, and Edg-7

In an effort to develop selective antagonists to the Edg-2, -4, and -7 receptors, a system for screening potential compounds was first established. RH7777 cells were chosen as a model system since they have been reported to be non-responsive to LPA in a variety of cellular assays and were found to be devoid of mRNA for any of the known Edg receptors (Fukushima et al., 1998). Stable cells lines transfected with the EDG receptors, as well as control cell lines transfected with empty vector, were established in RH7777 cells.

The resulting clones were screened by monitoring intracellular $Ca^{2+}$ transients, and by RT-PCR. This screening process led to the identification of at least three positive cell lines expressing Edg-2 and -7, while no positive cell lines expressing Edg-4 could be identified. Vector transfected cells were also found to be non-responsive to LPA. Although stable clones expressing Edg-4 were not isolated, the transient expression of Edg-4 resulted in the LPA-mediated activation of intracellular $Ca^{2+}$ transients, demonstrating that the construct was functionally active in these cells. The stable Edg-4 cell line used in these experiments was isolated and characterized by Im et al., who kindly provided us with the same clone (Im et al., 2000).

The cell lines were further characterized in an effort to identify a suitable assay for screening potential antagonists. LPA-elicited activation of ERK 1/2 was seen in Edg-2 and transient Edg-4 expressing cells, whereas ERK 1/2 was not activated in Edg-7 expressing cells. LPA elicited $Ca^{2+}$ transients in all stable cell lines expressing Edg-2, -4, and -7. Dose response curves revealed $EC_{50}$ values of 378±53, 998±67, and 214±26 nM for Edg-2, -4, -7 expressing cells, respectively (FIGS. 28A–C). Because the $EC_{50}$ value determined in the stable Edg-4 clone was different from that previously reported, a dose response curve was also established for cells transiently expressing Edg-4 (FIG. 28B, An et al., 1998a; An et al., 1998b), which yielded an $EC_{50}$ value of 186±39.

The ability of LPA to stimulate DNA synthesis in the stable cell lines was examined by measuring the incorporation of $^3$H-thymidine. Neither wild type, nor the vector transfected RH7777 cells showed an increase in $^3$H-thymidine incorporation following a 24 hr incubation with 10 μM LPA, which is in contrast to a previous report that LPA is mitogenic in these cells. Edg-2 expressing cells showed a 1.8-fold increase in $^3$H-thymidine incorporation, whereas Edg-4 and -7 expressing cells did not show an increase in $^3$H-thymidine incorporation, as compared to control cells.

Example 14

Short Chain Phosphatidates Activity on Edg-2 and Edg-7 Receptors

Since $Ca^{2+}$ transients were elicited in all three stable cell lines expressing Edg-2, -4, and -7 (FIGS. 28A–C), this assay was used for screening potential antagonists. In an effort to identify selective antagonists for the LPA activated members of the Edg receptor family, Edg-2, -4, and -7, the structural features of the LPA pharmacophore were relied upon as a starting point. Short-chain (8:0) LPA or a mixture of LPA (8:0) and LPA (18:1) were tested as inhibitors of Edg-2, -4, or -7. When the cells were challenged with the mixture of LPA 8:0 and LPA 18:1, $Ca^{2+}$ responses were not effected in any of the three stable cell lines (see FIGS. 30A–C, 31A–C, and 32A–B). LPA 8:0, alone, was unable to elicit $Ca^{2+}$ responses in any of the cells, at concentrations as high as 10 μM.

Based on these results, applicants hypothesized that a modification of the LPA pharmacophore, which sterically restricted the mobility of the fatty acid chain, might also effect its ligand properties. For this reason, we tested compounds with a second short-chain fatty acid at the sn-2 position were also tested. Such short-chain phosphatidates have increased hydrophobicity over the corresponding short-chain LPA, which could exert constraints on their interaction with the ligand-binding pocket of the receptor.

Phosphatidic acid (PA) and diacylglycerol pyrophosphate (DGPP) are naturally occurring lipids which share some key chemical properties with the LPA pharmacophore, having an ionic phosphate group(s) and fatty acid chains. Neither is an agonist of the Edg receptors (see below). With this similarity in mind, short-chain DGPP were prepared and tested as an inhibitor of Edg-2, -4, or -7. FIGS. 29A–D show the effect of a 10-fold excess of DGPP (8:0) on the $Ca^{2+}$ responses elicited by LPA in the stable cell lines. The $Ca^{2+}$ responses in Edg-2 expressing cells were inhibited by approximately 50% (FIG. 29A), whereas the responses in Edg-7 expressing cells were completely abolished (FIG. 29C). In contrast, $Ca^{2+}$ responses in Edg-4 expressing cells were unaffected by DGPP 8:0 (FIG. 29B). Because of the discrepancy in $EC_{50}$ values for the stable and transient expression of Edg-4 (FIG. 29B), DGPP 8:0 was similarly tested on cells that were transiently transfected with Edg-4. Consistent with results from experiments in stable cells, $Ca^{2+}$ responses were not effected by DGPP 8:0 in cells transiently expressing Edg-4 (FIG. 29D). Similar observations were obtained with PA 8:0 in each of the assays described above for DGPP 8:0 (see below).

Inhibition curves were determined in cells expressing Edg-2 and -7, using increasing concentrations of DGPP 8:0, while the concentration of LPA was kept constant at the $EC_{50}$ relative to the receptor studied. $IC_{50}$ values of 285±28 nM for Edg-7 (FIG. 30A) and 11.0±0.68 μM for Edg-2 (FIG. 31A) were determined from the curves. Using a constant amount of DGPP 8:0 near to the $IC_{50}$ value (250 nM for Edg-7, 3 μM for Edg-2), the dose response curves for both Edg-7 (FIG. 30B) and Edg-2 (FIG. 31B) were shifted to the right, indicating a competitive mechanism of inhibition.

In order to better define the structure activity relationship for DGPP, short- (8:0) and long-chain (18:1) species of LPA, DGPP, PA, and DAG were tested on Edg-2 and -7 expressing cell lines. FIG. 30C shows the effect of these lipids on the $Ca^{2+}$ responses in Edg-7 expressing cells when exposed to a combination of LPA 18:1 and each of these lipids. For these experiments, the concentration of LPA was chosen to be near the $EC_{50}$, whereas test lipids were applied at a concentration equal to the $IC_{50}$ of DGPP 8:0. LPA 8:0 had no effect on Edg-7, whereas both DGPP 8:0 and PA 8:0 significantly inhibited the $Ca^{2+}$ responses by 50 and 56%, respectively. In contrast DAG 8:0 significantly increased the $Ca^{2+}$ responses. When the chain length of DGPP and PA was increased to 18:1, these analogs were no longer inhibitors of Edg-7 (FIG. 30C). DAG 18:1, likewise, did not have an inhibitory effect on Edg-7.

The same set of lipids was tested on Edg-2 expressing cells (FIG. 31C). Octyl chain length analogs of DGPP, PA, and DAG, when used at 10 $\mu$M, all decreased the responses to 50, 19, and 64% of control, respectively. When the chain length was increased to 18:1, DGPP and DAG no longer had an inhibitory effect, whereas PA 18:1 maintained a modest inhibitory effect, decreasing the $Ca^{2+}$ response by 18%. The panel of lipids was also tested on Edg-4 expressing cells (FIGS. 32A–B). When these lipids were assayed in the stable cell line expressing Edg-4, none of the short- or long-chain lipids had an inhibitory effect, whereas both PA 8:0 and 18:1 significantly increased the $Ca^{2+}$ responses, to 162 and 137% of control, respectively. To confirm the results obtained from the stable clone, the lipid panel was tested on cells transiently expressing Edg-4 (FIG. 32B). Again, neither the short-, nor the long-chain species of DGPP or PA had an inhibitory effect on the $Ca^{2+}$ response, in agreement with the results from the stable cell line. In contrast to the stable Edg-4 clone, neither PA analog enhanced the $Ca^{2+}$ response in cells with transient expression of Edg-4. Neither species of PA when applied alone, elicited a response at concentrations up to 10 $\mu$M, in cells stably or transiently expressing Edg-4.

The effect of DGPP 8:0 on cells that endogenously express LPA receptors was also examined. DGPP 8:0 was found to inhibit the $Ca^{2+}$-mediated, inward $Cl^-$ currents elicited by LPA in *Xenopus* oocytes with an $IC_{50}$ of 96±21 nM (FIG. 33A). In the presence of a 200 nM concentration of DGPP 8:0, the dose response curve for LPA 18:1 was shifted to the right, indicating a competitive mechanism of action as found in Edg-2 and -7 clones (FIG. 33B). To examine whether DGPP 8:0 acts through an intracellular or extracellular mechanism, DGPP 8:0 was injected intracellularly and the oocyte was exposed to LPA 18:1. FIG. 32C shows that following the intracellular injection of DGPP 8:0, estimated to reach a concentration >300 nM, the extracellular application of 5 nM LPA 18:1 elicited a response equal in size to that of the control. In comparison, the response normally elicited by LPA 18:1 was completely inhibited when DGPP 8:0 was applied extracellularly (FIG. 33C). The inhibitory effect of DGPP 8:0 was reversible, as after a 10-min washing the response recovered to control level (FIG. 33C).

To show the specificity of DGPP 8:0 for the LPA receptors expressed in the oocyte, the expression of neurotransmitter receptors was induced by the injection of polyA+ mRNA from rat brain. This resulted in the expression of the G-protein coupled receptors for serotonin and acetycholine, which are not expressed in non-injected oocytes. These neurotransmitters activate the same inositol trisphophate-$Ca^{2+}$ signaling pathway that is activated by LPA (Tigyi et al., 1990). In these oocytes, DGPP 8:0 did not inhibit either serotonin- or carbachol-elicited responses, demonstrating the specificity of DGPP 8:0 for the LPA receptors. PA 8:0 when used at similar concentrations was also effective at inhibiting the LPA-elicited responses in the oocytes.

The effect of DGPP 8:0 on LPA-elicited responses was also examined in mammalian systems that endogenously express LPA receptors. NIH3T3 cells were screened by RT-PCR for the presence of mRNA for the Edg and PSP24 receptors. FIG. 34A shows that in NIH3T3 cells mRNA transcripts for Edg-2, -5, and PSP24 were detected. To show that DGPP 8:0 was specific in inhibiting LPA-elicited but not S1P-elicited $Ca^{2+}$ responses, NIH3T3 cells were exposed to 100 nM LPA or S1P in the presence of 10 $\mu$M DGPP 8:0. As shown in FIG. 34B, DGPP 8:0 significantly inhibited the LPA-elicited $Ca^{2+}$ responses, whereas the S1P-elicited response was not effected.

LPA has been shown to be generated from and play a role in ovarian cancer (Xu et al., 1995a). Therefore, DGPP 8:0 was also tested on HEY ovarian cancer cells to determine if it had an effect on a therapeutically relevant target. FIG. 34D shows that DGPP 8:0 inhibited the LPA-elicited $Ca^{2+}$ response to 12% of control, whereas DGPP 18:1 had no effect. Likewise, PA 8:0 inhibited the $Ca^{2+}$ response to 6% of control, whereas PA 18:1 had no effect. HEY express mRNA transcripts for Edg-1, -2, -5, -7 receptors (FIG. 34C).

Example 15

Inhibition of NIH3T3 Cell Proliferation

Figure 35:
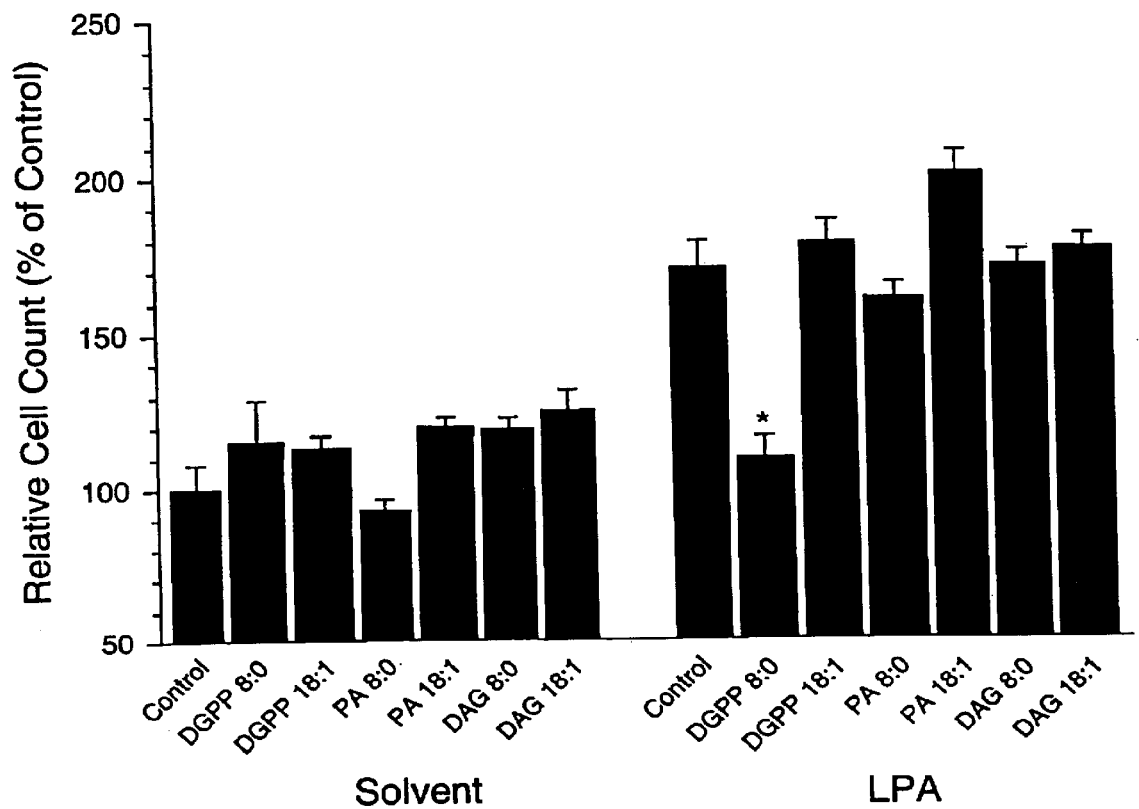
FIG. 35 is a graph illustrating DGPP 8:0 inhibition of LPA-elicited proliferation of NIH3T3 cells. NIH3T3 cells were serum-starved for 6 hr and exposed to a 5 μM concentration of LPA 18:1 mixed with a 10 μM concentration of the indicated lipids. Control cells received solvent (BSA) in place of LPA 18:1. The cells were incubated for 24 hr with the lipids and counted. Data are representative of three experiments.

The hallmark effect of a growth factor is its ability to elicit cell proliferation. Since LPA has been shown to stimulate the proliferation of a variety of different cell types (Goetzl et al., 2000), the ability of DGPP 8:0 to inhibit cell proliferation was examined in NIH3T3 cells. FIG. 35 shows that DGPP 8:0 significantly inhibited the LPA-induced proliferation of NIH3T3 cells, reducing cell number to control levels, whereas it had no effect on the solvent-treated control cells.

To define the structure-activity relationship for the inhibitory effect of DGPP 8:0, the short- and long-chain species of DGPP, PA, and DAG were included in the assay. As shown in FIG. 35, none of the lipids included in the test panel had a significant inhibitory or stimulatory effect on the solvent-treated control cells. Only DGPP 8:0 inhibited the LPA-induced proliferation. Neither DGPP 18:1, nor long- and short-chain PA and DAG had an effect on the LPA-induced proliferation. Interestingly, PA 8:0 had no significant inhibition in this assay.

Discussion of Examples 13–15

RH7777 cells were used for heterologous expression of Edg-2, -4, and -7 receptors to screen potential antagonists. Based on our previous computational modeling of the Edg receptors (Parrill et al. 2000) and the available structure-activity data (Jalink et al., 1995), the above experimental results demonstrate that the short-chain phosphatidate DGPP 8:0 is a selective, competitive antagonist of Edg-7, with an $IC_{50}$ value of 285±28 nM. The same molecule was found to be a poor inhibitor of Edg-2, with an $IC_{50}$ value of 11.0±0.68 $\mu$M, whereas it did not inhibit Edg-4. DGPP 8:0 inhibited the endogenous LPA response in *Xenopus* oocytes with an $IC_{50}$ value of 96±21 nM. PA 8:0 showed similar inhibitory properties. Therefore, these short-chain phosphatidates show a 40–100-fold selectivity for Edg-7 over Edg-2.

The above results with short-chain phosphatidates confirm those of Bandoh et al. (2000) who demonstrated that LPA, with an acyl chain-length of twelve carbons or less, does not elicit responses in insect cells expressing Edg-2, -4, or -7. As demonstrated above, LPA 8:0 was neither an agonist nor an antagonist of Edg-2, -4, or -7 in a mammalian expression system. Edg-7 has a 10-fold preference for LPA with the fatty acid chain esterified to the sn-2, versus the sn-1 position (Bandoh et al., 2000). Therefore, the distance of the hydrocarbon chain relative to the phosphate moiety, does not abolish the binding to and activation of the receptor. Edg-7 also shows a preference for long-chain, unsaturated fatty acids over their saturated counterparts. The presence of an ether linkage or vinyl-ether side chain also decreased the $EC_{50}$ by two orders of magnitude (Bandoh et al., 2000). Moreover, there is an optimal hydrocarbon chain-length of 18 carbons, whereas 20 carbon analogs were weaker agonists. These pharmacological properties of Edg-7 suggest that receptor activation is dependent upon the chain length, as well as the flexibility of the side chain (ester vs. ether linkage).

Computational modeling of the Edg-1 receptor has identified three charged residues that are required for ligand binding. One of these residues, arginine 120, which is predicted to interact with the phosphate group, is conserved in all of the members of the Edg family. The second residue, arginine 292, occurs at a position where all Edg family members except Edg-8 have a nearby cationic residue. The third residue, glutamate 121, is not conserved amongst the LPA-specific Edg receptors, with a glutamine at the corresponding site in Edg-2, -4, and -7. This glutamine residue is predicted to interact with the hydroxyl moiety of LPA. Alanine replacement of this residue has led to a loss of ligand binding and activation of the receptor, suggesting that the ionic interaction between the charged moieties of the PLGF pharmacophore and these three residues is necessary for ligand binding in Edg-1 (Parrill et al., 2000). Moreover, the interaction between the receptor and the hydrocarbon chain, itself, was not sufficient for ligand binding and activation (Parrill et al., 2000). It was hypothesized, therefore, that a combination of interactions, involving both the ionic anchor and the hydrophobic tail, are required for agonist activation. In support of this hypothesis, the above results demonstrate that the short-chain LPA 8:0 was not able to activate Edg-2, -4, or -7, underlying the importance of the interaction between the hydrophobic tail and the ligand binding pocket. As a result, applicants have designated the hydrophobic tail as the "switch" region of the PLGF pharmacophore. Because of the relative tolerance of the sn-1 and sn-2 substitution of the fatty acids by these receptors, applicants focused on short-chain phosphatidates which were believed not to be able to activate the receptors due to their truncated hydrocarbon chains. The structural mobility of the acyl chains in the phosphatidates is also limited by the adjacent fatty acid moiety. Applicants also explored the effects of a pyrophosphate moiety, which does not change the negatively charged character of the anchoring region, but rather increases the charge.

This conceptual drug design was tested on clonal cell lines expressing the Edg-2, -4, and -7 receptors. The pharmacological properties of DGPP 8:0 and PA 8:0 were found to be dramatically different between the three receptors. Both molecules were effective at inhibiting Edg-7, whereas they were more than an order of magnitude less effective on Edg-2. Neither molecule was effective on Edg-4. DGPP 8:0 was also found to be a competitive inhibitor of both Edg-2 and -7, displacing the dose response curves to the right with a subsequent increase in the $EC_{50}$ values for LPA on both receptors. The lack of agonist activity of the corresponding long-chain species of PA and DGPP, highlights the constraints that prevail in the binding pocket. The importance of the ionic anchor, in docking the ligand in the binding pocket, is supported by the lack of inhibition by DAG 8:0, although its cellular effects are likely confounded by its intracellular actions on other molecular targets, such as PKC.

Both PA and DGPP are naturally occurring phospholipids. DGPP (8:0) was discovered in 1993 as a novel lipid in plants and is a product of the phosphorylation of PA by phosphatidate kinase (Wissing and Behrbohm, 1993; Munnik et al., 1996). DGPP has been identified in bacteria, yeast and plants, but not in mammalian cells. Recent studies have shown that DGPP activates macrophages and stimulates prostaglandin production through the activation of cytosolic phospholipase $A_2$, suggesting a role for DGPP in the inflammatory response (Balboa et al., 1999; Balsinde et al., 2000). These authors ruled out the possibility that these effects were mediated through LPA receptors. The above results with the long-chain DGPP and PA analogs confirmed this notion, as these compounds did not possess agonist properties in the Edg receptor expressing cell lines at concentrations up to 10 $\mu$M.

The effect of short chain phosphatidates was also examined on LPA receptors expressed endogenously in three different cell types. DGPP 8:0 and PA 8:0 were found to be effective inhibitors of LPA-elicited $Cl^-$ currents in *Xenopus* oocytes. In order to determine the site of action, DGPP 8:0 was injected into oocytes followed by an extracellular application of LPA. DGPP 8:0 was only effective at inhibiting the LPA-elicited $Cl^-$ currents when applied extracellularly, demonstrating that it exerts its antagonist effect on the cell surface. The specificity of DGPP 8:0 for LPA receptors was demonstrated in oocytes and NIH3T3 cells. In these cells, DGPP 8:0 was only effective at inhibiting the LPA-elicited $Ca^{2+}$ responses and not the responses elicited by S1P, acetycholine, or serotonin.

RT-PCR analysis revealed that only Edg-2, and not Edg-4, or -7 is expressed in NIH3T3 cells. In NIH3T3 cells, DGPP 8:0, at a high 100-fold excess, only inhibited the $Ca^{2+}$ responses by 40%. This degree of inhibition parallels that seen in the stable cell line expressing Edg-2, where it was also a weak inhibitor. When short-chain DGPP and PA were evaluated on HEY ovarian cancer cells, at a 10-fold excess over LPA, both were effective inhibitors, whereas neither long-chain molecule had any effect. RT-PCR revealed that the predominant mRNA was for Edg-7 in HEY cells, whereas only a trace of Edg-2 mRNA was detected. This degree of inhibition parallels that seen in the stable cell line expressing Edg-7, where both DGPP 8:0 and PA 8:0 were effective inhibitors.

Both short chain phosphatidates were evaluated for their ability to block the LPA-induced proliferation of NIH3T3 cells. DGPP 8:0 effectively inhibited the LPA-induced proliferation, while the long-chain DGPP did not. Although PA 8:0 was effective at inhibiting the $Ca^{2+}$ responses, it was not effective at inhibiting cell proliferation. These results are in agreement with a previous report that PA (12:0) did not inhibit the mitogenic effect of PA 18:1 (van Corven et al., 1992). The stability of the molecules in long-term assays is a concern, since lipid phosphatases might inactivate the antagonist. The fact that both PA and DAG failed to inhibit the proliferation suggests that DGPP 8:0 is likely to be more stable for the duration of this assay. The stability of DGPP has also been demonstrated by Balboa et al. (1999), who reported that DGPP was not metabolized during the course of their experiments.

DGPP 8:0 provides an important new tool for the field in studying, not only the Edg receptors but also other PLGF receptors. The concept of an ionic anchor and hydrophobic switch of the PLGF pharmacophore derived from computational modeling of the Edg family should assist the design and synthesis of new inhibitors.

Example 16

Synthesis of Straight-Chain Phosphate Intermediates 101–105

Compound 101

Phosphoric Acid Dibenzyl Ester Butyl Ester 74 mg (1.00 mmol) of anhydrous n-butanol and 365 mg (5.17 mmol) of 1H-tetrazole were dissolved in 34 mL of anhydrous methylene chloride in a 100 mL round-bottom flask. A solution of 0.895 g (2.58 mmol) of dibenzyl-N,N-diisopropyl phosphoramidite in 5 mL of anhydrous methylene chloride was added via a syringe under an argon atmosphere with stirring. The reaction mixture was stirred at room temperature for 2 hrs. The reaction mixture was then cooled in a isopropyl alcohol/dry ice bath at ~38° C. 0.815 g (3.43 mmol) of 32% peracetic acid in 28 mL of anhydrous methylene chloride were added dropwise via an addition funnel. After the addition, the temperature of the reaction mixture was raised to ~0° C. with an ice bath. The reaction mixture was stirred in the ice bath for 1 hr. The reaction mixture was transferred to a separatory funnel and diluted with 200 mL of methylene chloride. The organic layer was washed with 10% sodium metabisulfite (2×40 mL), saturated sodium bicarbonate (2×40 mL), water (30 mL), and brine (40 mL). The organic layer was dried with anhydrous sodium sulfate, filtered, and concentrated under vacuum to dryness. The crude product was then purified by silica gel chromatography using 1:1 hexanes/ethyl acetate as the eluent to afford 101 (309 mg which contained a slight amount of impurity from excess phosphorylating reagent) as a clear oil. $^1$H NMR (CDCl$_3$) 0.88 (t, J=7.2 Hz, 3H, C$\underline{H}_3$), 1.34 (sextet, J=7.2 Hz, 2H, OCH$_2$CH$_2$C$\underline{H}_2$CH$_3$), 1.59 (quintet, J=6.6 Hz, 2H, OCH$_2$C$\underline{H}_2$CH$_2$CH$_3$), 3.99 (dt, J=6.6 Hz, 6.6 Hz, 2H, OC$\underline{H}_2$CH$_2$CH$_2$CH$_3$), 5.02 (d, J=1.8 Hz, 2H, OC$\underline{H}_2$Ar), 5.05 (d, J=2.1 Hz, 2H, OC$\underline{H}_2$Ar), 7.35 (br s, 10H, 2×Ar$\underline{H}$); $^{13}$C NMR (CDCl$_3$) 13.55, 18.60, 32.16 (d, J$_{C,P}$=6.8 Hz), 67.72 (d, J$_{C,P}$=6.1 Hz), 69.13(d, J$_{C,P}$=5.5 Hz), 127.90, 128.47, 128.55, 136.00 (d, J$_{C,P}$=6.8 Hz); $^{31}$P NMR (CDCl$_3$) 16.84; MS (positive mode): [M+$^{23}$Na] at m/z 357.3.

Compound 102

Phosphoric Acid Dibenzyl Ester Octyl Ester 130 mg (1.00 mmol) of anhydrous n-octanol were used and a procedure analogous to that for 101 was performed. The crude product was purified by silica gel chromatography using 7:3 hexanes/ethyl acetate as the eluent to afford 102 (351 mg, 90%) as a clear oil. $^1$H NMR (CDCl$_3$) 0.88 (t, J=6.9 Hz, 3H, C$\underline{H}_3$), 1.24 (br s, 10H, OCH$_2$CH$_2$(C$\underline{H}_2$)$_5$CH$_3$), 1.60 (quintet, J=6.9 Hz, 2H, OCH$_2$C$\underline{H}_2$(CH$_2$)$_5$CH$_3$), 3.98 (dt, J=6.6 Hz, 6.9 Hz, 2H, OC$\underline{H}_2$CH$_2$(CH$_2$)$_5$CH$_3$), 5.02 (d, J=2.1 Hz, 2H, OC$\underline{H}_2$Ar), 5.05 (d, J=2.4 Hz, 2H OC$\underline{H}_2$Ar), 7.34 (br s, 10H, 2×Ar$\underline{H}$); $^{13}$C NMR (CDCl$_3$) 14.09, 22.62, 25.38, 29.06, 29.14, 30.17 (d, J$_{C,P}$=6.9 Hz), 31.75, 68.05 (d, J$_{C,P}$=6.2 Hz), 69.12 (d, J$_{C,P}$=5.5 Hz), 127.90, 128.47, 128.56, 135.97 (d, J$_{C,P}$=6.9 Hz); $^{31}$P NMR (CDCl$_3$) 16.83; MS (positive mode): [M+$^{23}$Na]$^+$ at m/z 413.4.

Compound 103

Phosphoric Acid Dibenzyl Ester Dodecyl Ester 186 mg (1.00 mmol) of anhydrous n-butanol were employed and a procedure analogous to that for 101 was utilized. The crude product was purified by silica gel chromatography using 7:3 hexanes/ethyl acetate as the eluent to afford 103 (361 mg, 81%) as a clear oil. $^1$H NMR (CDCl$_3$) 0.88 (t, J=7.2 Hz, 3H, C$\underline{H}_3$), 1.24 (br s, 18 H, OCH$_2$CH$_2$(C$\underline{H}_2$)$_9$CH$_3$), 1.60 (quintet, J=6.9 Hz, 2H, OCH$_2$C$\underline{H}_2$(CH$_2$)$_9$CH$_3$), 3.98 (td, J=6.9 Hz, 6.6 Hz, 2H, OC$\underline{H}_2$CH$_2$(CH$_2$)$_9$CH$_3$), 5.02 (d, J=2.1 Hz, 2H, OC$\underline{H}_2$Ar), 5.05 (d, J=2.1 Hz, 2H, OC$\underline{H}_2$Ar), 7.34 (br s, 10H, 2×Ar$\underline{H}$); $^{13}$C NMR (CDCl$_3$) 14.13, 22.69, 25.38, 29.12, 29.35, 29.49, 29.56, 29.63, 30.18 (d, J$_{C,P}$=7.0 Hz), 31.92, 68.05 (d, J$_{C,P}$=6.1 Hz), 69.12 (d, J$_{C,P}$=5.4 Hz), 127.89, 128.46, 128.55, 135.97 (d, J$_{C,P}$=6.8 Hz); $^{31}$P NMR (CDCl$_3$) 16.84; MS (positive mode): [M+$^{23}$Na]$^+$ at m/z 469.1.

Compound 104

Phosphoric Acid Dibenzyl Ester Octadecyl Ester 270 mg (1.00 mmol) of octadecanol were used and the same procedure as for 101 was employed. The crude product was purified by silica gel chromatography using 7:3 hexanes/ethyl acetate as the eluent to afford 104 (474 mg, 89%) as a hygroscopic white solid: mp 32–33° C.; $^1$H NMR (CDCl$_3$) 0.88 (t, J=6.9 Hz, 3H, C$\underline{H}_3$), 1.25 (br s, 30H, OCH$_2$CH$_2$(C$\underline{H}_2$)$_{15}$CH$_3$), 1.60 (quintet, J=6.9 Hz, 2H, OCH$_2$C$\underline{H}_2$(CH$_2$)$_{15}$CH$_3$), 3.98 (td, J=6.6 Hz, 6.9 Hz, 2H, OC$\underline{H}_2$CH$_2$(CH$_2$)$_{15}$CH$_3$), 5.02 (d, J=2.1 Hz, 2H, OC$\underline{H}_2$Ar), 5.05 (d, J=2.1 Hz, 2H, OC$\underline{H}_2$Ar), 7.34 (br s, 10H, 2×Ar$\underline{H}$); $^{13}$C NMR (CDCl$_3$) 14.12, 22.70, 25.40, 29.13, 29.38, 29.51, 29.58, 29.68, 29.72, 30.20 (d, J$_{C,P}$=6.9 Hz), 31.94, 68.06 (d, J$_{C,P}$=6.1 Hz), 69.14 (d, J$_{C,P}$=5.4 Hz), 127.90, 128.47, 128.55, 136.00 (d, J$_{C,P}$=6.8 Hz).; $^{31}$P NMR (CDCl$_3$) 16.83; MS (positive mode): [M+$^{23}$Na]$^+$ at m/z 553.3.

Compound 105

Phosphoric Acid Dibenzyl Ester Docosanyl Ester 327 mg (1.00 mmol) of docosanol were employed and an analogous procedure to that for 101 was used. The crude product was purified by silica gel chromatography using 7:3 hexanes/ethyl acetate as the eluent to afford 105 (516 mg, 88%) as a hygroscopic white solid: mp 43.5–44.5° C.; $^1$H NMR (CDCl$_3$) 0.88 (t, J=6.9 Hz, 3H, C$\underline{H}_3$), 1.25 (br s, 38H, OCH$_2$CH$_2$(C$\underline{H}_2$)$_{19}$CH$_3$), 1.60 (quintet, J=6.9 Hz, 2H, OCH$_2$C$\underline{H}_2$(CH$_2$)$_{19}$CH$_3$), 3.98 (td, J=6.6 Hz, 6.6 Hz, 2H, OC$\underline{H}_2$CH$_2$(CH$_2$)$_{19}$CH$_3$), 5.02 (d, J=2.4 Hz, 2H, OC$\underline{H}_2$Ar), 5.05 (d, J=2.4 Hz, 2H, OC$\underline{H}_2$Ar), 7.35 (br s, 10H, 2×ArH); $^{13}$C NMR (CDCl$_3$) 14.13, 22.70, 25.39, 29.12, 29.37, 29.50, 29.57, 29.66, 29.71, 30.18(d, J$_{C,P}$=6.9 Hz), 31.93, 68.06 (d, J$_{C,P}$=6.0 Hz), 69.13 (d, J$_{C,P}$=5.6 Hz), 127.89, 128.47, 128.55, 135.98 (d, J$_{C,P}$=6.9 Hz); $^{31}$P NMR (CDCl$_3$) 16.83; MS (positive mode): [M+$^{23}$Na]$^+$ at m/z 609.3.

Example 17

Synthesis of Straight-Chain Phosphate Compounds 106–110

Compound 106

Phosphoric Acid Monobutyl Ester 200 mg (0.60 mmol) of 101 were dissolved in 30 mL of anhydrous methanol in a thick-walled pressure vessel. The vessel was purged with argon and ~200 mg of 10% Pd/C was added. The vessel was connected to a hydrogenation apparatus and a hydrogen atmosphere of ~50 psi was maintained inside the reaction vessel at room temperature for 8 hrs. The reaction mixture was then filtered by vacuum through a pad of celite which was washed with methanol. The solvent was evaporated under vacuum leaving behind 70 mg (86%) of a yellow oil 106. $^1$H NMR (CDCl$_3$/MeOH-d$_4$) 0.95 (t, J=7.2 Hz, 3H, C$\underline{H}_3$), 1.43 (sextet, J=7.5 Hz, 2H, OCH$_2$CH$_2$C$\underline{H}_2$CH$_3$), 1.66 (quintet, J=6.9, 2H, OCH$_2$C$\underline{H}_2$CH$_2$CH$_3$), 3.99 (td, J=6.6 Hz, 6.6 Hz, 2H, OC$\underline{H}_2$CH$_2$CH$_2$CH$_3$); $^{13}$C NMR (CDCl$_3$/MeOH-d$_4$) 13.71, 19.02, 32.72 (d, J$_{C,P}$=7.2 Hz), 66.86 (d, J$_{C,P}$=5.5 Hz); $^{31}$P NMR (CDCl$_3$/MeOH-d$_4$) 18.84; MS (negative mode): [M–1]$^-$ at m/z 153.0.

Compound 107

Phosphoric Acid Monooctyl Ester 200 mg (0.51 mmol) of 102 were employed and using a procedure analogous to that for 106, 100 mg (93%) of a white/yellow tacky solid 107 was isolated. $^1$H NMR (CDCl$_3$/MeOH-d$_4$) 0.89 (t, J=6.9 Hz, 3H, C$\underline{H}_3$), 1.29 (br s, 10H, OCH$_2$CH$_2$(C$\underline{H}_2$)$_5$CH$_3$), 1.67 (quintet, J=6.9 Hz, 2H, OCH$_2$C$\underline{H}_2$(CH$_2$)$_5$CH$_3$), 3.97 (dt, J=6.6 Hz, 6.6 Hz, 2H, OC$\underline{H}_2$CH$_2$(CH$_2$)$_5$CH$_3$); $^{13}$C NMR (CDCl$_3$/MeOH-d$_4$) 14.18, 22.98, 25.89, 29.57, 29.58, 30.76 (d, J$_{C,P}$=7.3 Hz), 32.18, 67.16 (d, J$_{C,P}$=5.2 Hz); $^{31}$P NMR (CDCl$_3$/MeOH-d$_4$) 20.55; MS (negative mode): [M–1]$^-$ at m/z 209.1.

Compound 108

Phosphoric Acid Monododecyl Ester 200 mg (0.45 mmol) of 103 were employed and a procedure the same as that for 106 was used to afford 112 mg (94%) of a white solid 108. $^1$H NMR (CDCl$_3$/MeOH-d$_4$) 0.88 (t, J=6.6 Hz, 3H, C$\underline{H}_3$), 1.27 (br s, 18 H, OCH$_2$CH$_2$(C$\underline{H}_2$)$_9$CH$_3$), 1.67 (quintet, J=6.6 Hz, 2H, OCH$_2$C$\underline{H}_2$(CH$_2$)$_9$CH$_3$), 3.97 (dt, J=6.6Hz, 6.6Hz, 2H, OC$\underline{H}_2$CH$_2$(CH$_2$)$_9$CH$_3$); $^{13}$C NMR (CDCl$_3$/MeOH-d$_4$) 14.21, 22.98, 25.84, 29.57, 29.67, 29.89, 29.92, 29.96, 29.98, 30.69 (d, J$_{C,P}$=7.4 Hz), 32.25, 67.22 (d, J$_{C,P}$=5.7 Hz); $^{31}$P NMR (CDCl$_3$/MeOH-d$_4$) 21.22; MS (negative mode): [M–1]$^-$ at m/z 265.0.

Compound 109

Phosphoric Acid Monooctadecyl Ester 200 mg (0.38 mmol) of 104 were used and an analogous procedure to that of 106 was employed which yielded 104 mg (79%) of a white solid 109. $^1$H NMR (CDCl$_3$/MeOH-d$_4$) 0.89 (t, J=6.9 Hz, 3H, C$\underline{H}_3$), 1.27 (br s, 30H, OCH$_2$CH$_2$(C$\underline{H}_2$)$_{15}$CH$_3$), 1.68 (quintet, J=6.9 Hz, 2H, OCH$_2$C$\underline{H}_2$(CH$_2$)$_{15}$CH$_3$), 3.98 (dt, J=6.6 Hz, 6.9 Hz, 2H, OC$\underline{H}_2$CH$_2$(CH$_2$)$_{15}$CH$_3$); $^{13}$C NMR (CDCl$_3$/MeOH-d$_4$) 14.26, 23.14, 26.01, 29.74, 29.84, 30.06, 30.09, 30.16, 30.87 (d, J$_{C,P}$=7.2 Hz), 32.42, 67.32 (d, J$_{C,P}$=5.8 Hz); $^{31}$P NMR (CDCl$_3$/MeOH-d$_4$) 21.69; MS (negative mode): [M–1]$^-$ at m/z 349.1.

Compound 110

Phosphoric Acid Monodocosyl Ester 200 mg (0.34 mmol) of 105 were employed and the same procedure as that for 106 was used yielding 98 mg (71%) of a white solid 110. $^1$H NMR (CDCl$_3$/MeOH-d$_4$) 0.88(t, J=6.9 Hz, 3H), 1.26 (br s, 38H, OCH$_2$CH$_2$(C$\underline{H}_2$)$_{19}$CH$_3$), 1.66 (quintet, J=6.9 Hz, 2H, OCH$_2$C$\underline{H}_2$(CH$_2$)$_{19}$CH$_3$), 3.97 (td, J=6.6 Hz, 6.6 Hz, 2H, OC$\underline{H}_2$CH$_2$(CH$_2$)$_{19}$CH$_3$); $^{13}$C NMR (CDCl$_3$/MeOH-d$_4$) 14.22, 23.01, 25.87, 29.61, 29.71, 29.93, 29.97, 30.04, 30.73 (d, J$_{C,P}$=7.4 Hz), 32.29, 67.27 (d, J$_{C,P}$=5.6Hz); $^{31}$P NMR (CDCl$_3$/MeOH-d$_4$) 20.66; MS (negative mode): [M–1]$^-$ at m/z 405.1.

Example 18

Straight-Chain Phosphate Compounds 106–110

*Xenopus* oocytes which endogenously express PSP24 PLGFR were used to screen compounds 106–110 for their LPA inhibitory activity. Oocytes were obtained from xylazine-anesthetized adult *Xenopus laevis* frogs (Carolina Scientific, Burlington, N.C.) under aseptic conditions and prepared for experiment. Stage V–VI oocytes were denuded of the the follicular cell layer with type A collagenase treatment (Boehringer, Ind.) at 1.4 mg/ml in a Ca$^{2+}$-free ovarian Ringers-2 solution ((OR-2) 82.5 mM NaCl, 2 mM KCl, 1 mM MgCl$_2$, 5 mM HEPES, pH 7.5, with NaOH). Oocytes were kept in Barth's solution in an incubator between 17–20° C. and were used for 2–7 days after isolation.

Electrophysiological recordings were carried out using a standard two-electrode voltage-clamp amplifier holding the membrane potential at –60 mV (GeneClamp 500, Axon Instruments, CA). Test compounds were dissolved in MeOH, complexed with fatty acid free BSA, and diluted with frog Na$^+$-Ringers solution (120 nM NaCl, 2 mM KCl, 1.8 mM CaCl$_2$, 5 mM HEPES; pH 7.0), which were applied through superfusion to the oocyte at a flow rate of 5 ml/min. Membrane currents were recorded with a NIC-310 digital oscilloscope (Nicolet, Madison, Wis.). Applications were made at intervals of 15 mins (minimum) to allow for the appropriate washout and recovery from desensitization.

Figure 36:
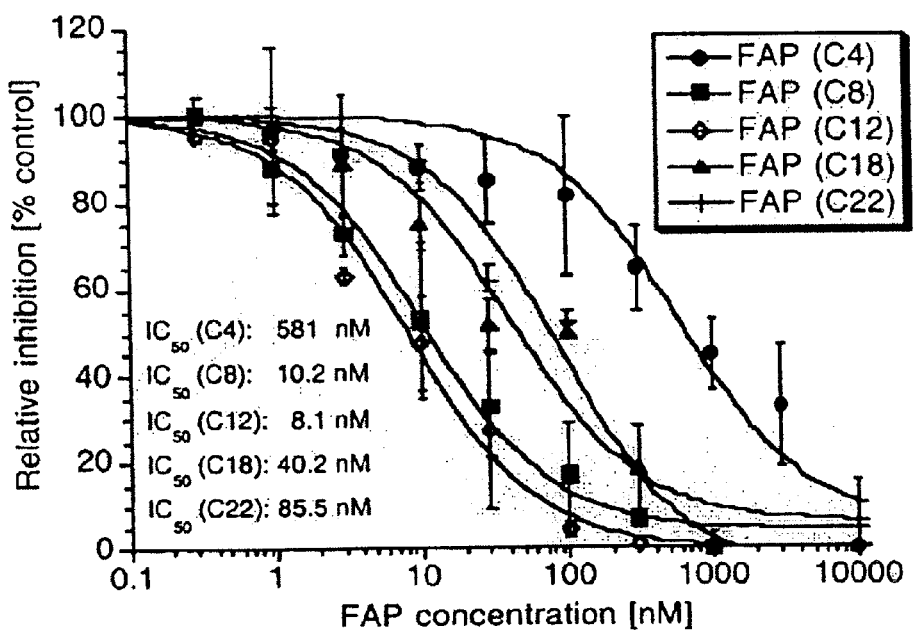
FIG. 36 is a graph which illustrates the pharmacological characterization of the inhibition of the LPA response by straight-chain fatty acid phosphate compounds 106–110 in Xenopus oocytes.
Figure 37:
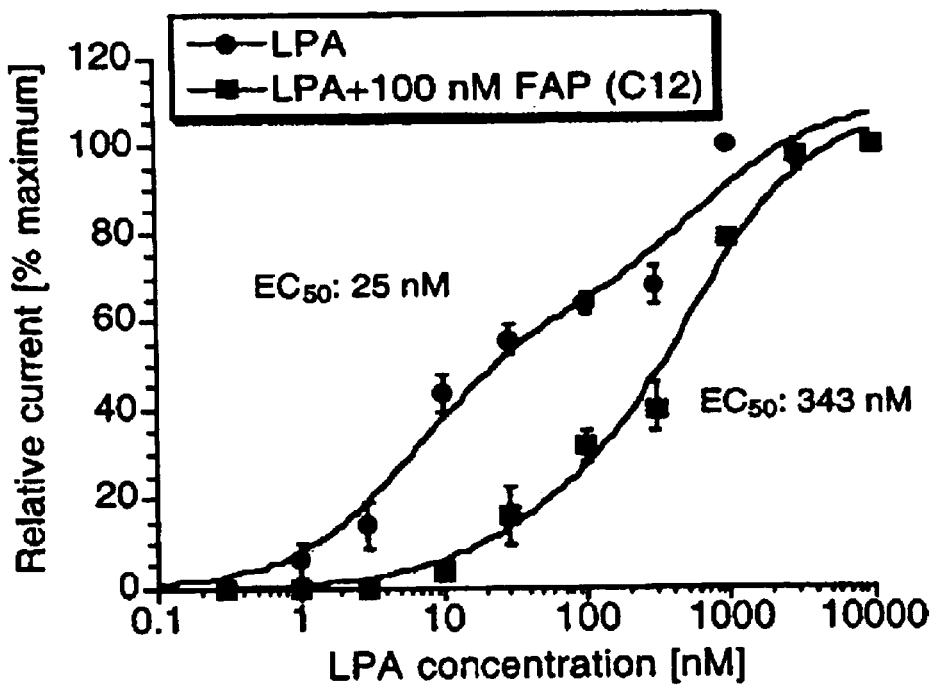
FIG. 37 is a graph which illustrates the pharmacological characterization of the inhibition of the LPA response by straight-chain fatty acid phosphate compound 108 in Xenopus oocytes.

FIG. 36 shows the dose-dependent inhibition of LPA-induced chloride currents by compounds 106–110. Compound 108 was the best inhibitor, having an IC$_{50}$ value of about 8.1 nM. Compounds with shorter or longer straight-chain alkyl groups showed decreasing efficacy in inhibiting LPA-induced chloride currents, although compound 107 displayed a similar efficacy with an IC$_{50}$ value of about 10.2 nM. FIG. 37 compares the EC$_{50}$ values for positive control solution (LPA alone), 25 nm, and a solution containing LPA and 100 nM of compound 108, 343 nM. Thus, compound 108 effectively inhibits LPA signalling of PSP24 receptors in *Xenopus* oocytes.

Based on the above results, compound 108 was also examined for its effectiveness as an antagonist of Edg-2, -4, and -7 receptors in RH7777 cells which heterologously express the individual receptors.

Figure 38:
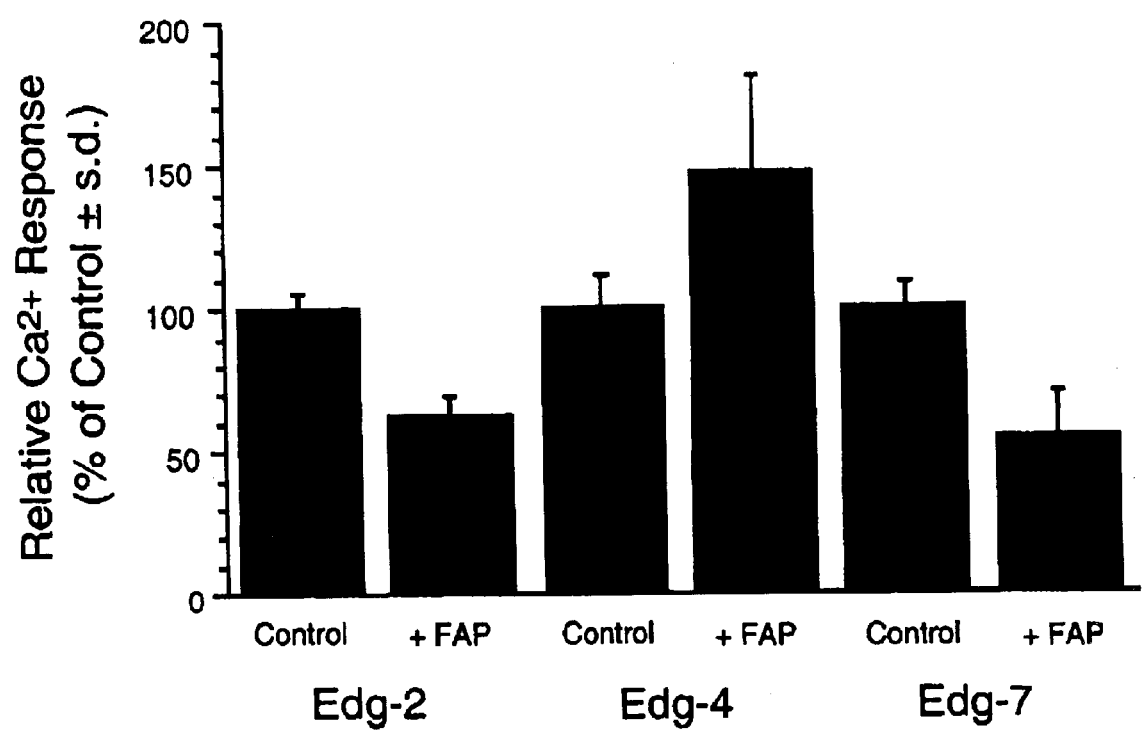
FIG. 38 is a graph illustrating the pharmacological characterization of the antagonist or agonist induced response of RH7777 cells inidividually expressing Edg-2, Edg-4, or Edg-7 receptors, following exposure of the cells to straight-chain fatty acid phosphate compound 108. Peak areas of the $Ca^{2+}$ responses were measured.

FIG. 38 shows the effect of compound 108 on the Ca$^{2+}$ responses in Edg-2, Edg-4, and Edg-7 expressing cells when exposed to a combination of LPA 18:1 and compound 108. For these experiments, the concentration of LPA was chosen to be near the EC$_{50}$. Compound 108 significantly inhibited the Ca$^{2+}$ responses to about 63% and 56% of control, respectively, in Edg-2 and Edg-7 expressing cell lines. In contrast, compound 108 significantly increased the Ca$^{2+}$ responses to about 148% of control in Edg-4 expressing cell lines.

Therefore, the straight-chain phosphates would be expected to selectively inhibit Edg-2 and Edg-7 activity in vivo and selectively enhance Edg-4 activity in vivo.

List of References

Each of the references listed below is hereby incorporated by reference in its entirety into the specification of this application.

Ahn et al., "Src-mediated tyrosine phosphorylation of dynamin is required for beta2-adrenergic receptor internalization and mitogen-activated protein kinase signaling," *J. Biol. Chem.* 274:1185–1188 (1999).

An et al., "Identification of cDNAs encoding two G protein-coupled receptors for lysosphingolipids," *FEBS. Lett.* 417:279–282 (1997a).

An et al., "Molecular cloning of the human Edg2 protein and its identification as a functional cellular receptor for lysophosphatidic acid," *Biochem. Biophys. Res. Commun.*, 231(3):619–622 (1997b).

An et al., "Characterization of a novel subtype of human G protein-coupled receptor for lysophosphatidic acid," *J. Biol. Chem.* 273:7906–7910 (1998a).

An et al., "Recombinant human G protein-coupled lysophosphatidic acid receptors mediate intracellular calcium mobilization," *Mol. Pharmacol.* 54:881–888 (1998b).

Balazs et al., "Topical application of LPA accelerates wound healing," *Ann. N.Y. Acad. Sci.* 905:270–273 (2000).

Balboa et al., "Proinflammatory macrophage-activating properties of the novel phospholipid diacylglycerol pyrophosphate," *J. Biol. Chem.* 274:522–526 (1999).

Balsinde et al., "Group IV cytosolic phospholipase A2 activation by diacylglycerol pyrophosphate in murine P388D1 macrophages," *Ann. NY Acad. Sci.* 905:11–15 (2000).

Bandoh et al., "Molecular cloning and characterization of a novel human G-protein-coupled receptor, EDG7, for lysophosphatidic acid," *J. Biol. Chem.* 274:27776–27785 (1999).

Bandoh et al., "Lysophosphatidic acid (LPA) receptors of the EDG family are differentially activated by LPA species; Structure-activity relationship of cloned LPA receptors," *FEBS Lett.* 478: 159–165 (2000).

Bishop and Bell, "Assembly of phospholipids into cellular membranes: biosynthesis, transmembrane movement and intracellular translocation," *Annu. Rev. Cell Biol.* 4:579–610 (1988).

Bittman et al., "Inhibitors of lipid phosphatidate receptors: N-palmitoyl-serine and N-palmitoyl-tyrosine phosphoric acids," *J. Lipid Res.* 37:391–398 (1996).

Bosch, "Phosphoglyceride metabolism," *Annu. Rev. Biochem.* 43:243–277 (1974).

Cherrick et al., "Effects of topically applied 5-fluorouracil in the Syrian hamster," *J. Invest. Dermatol.*, 63:284–286 (1974).

Cunnick et al., "Role of tyrosine kinase activity of epidermal growth factor receptor in the lysophosphatidic acid-stimulated mitogen-activated protein kinase pathway," *J. Biol. Chem.* 273:14468–14475 (1998).

Durieux et al., "Lysophosphatidic acid induces a pertussis toxin-sensitive Ca$^{2+}$-activated Cl− current in *Xenopus laevis* oocytes," *Am. J. Physiol.* 263:896–900 (1992).

Dyer et al., "The effect of serum albumin on PC12 cells: I. Neurite retraction and activation of the phosphoinositide second messenger system," *Mol. Brain Res.* 14:293–301 (1992).

Eicholtz et al., "The bioactive phospholipid lysophosphatidic acid is released from activated platelets," *Biochem. J.* 291:677–680 (1993).

Fernhout et al., "Lysophosphatidic acid induces inward currents in *Xenopus laevis* oocytes; evidence for an extracellular site of action," *European Journal of Pharmacology* 213:313–315 (1992).

Fischer et al., "Naturally occurring analogs of lysophosphatidic acid elicit different cellular responses through selective activation of multiple receptor subtypes," *Mol. Pharmacol.* 54:979–988 (1998).

Fukami and Takenawa, "Phosphatidic acid that accumulates in platelet-derived growth factor-stimulated Balb/c 3T3 cells is a potential mitogenic signal," *J. Biol. Chem.* 267:10988–10993 (1992).

Fukushima et al., "A single receptor encoded by vzg-1/1pA1/edg-2 couples to G proteins and mediates multiple cellular responses to lysophosphatidic acid," *Proc. Natl. Acad. Sci. USA* 95:6151–6 (1998).

Gerrard et al., "Lysopospatidic acids influence on platelet aggregation and intracellular calcium flux," *Am. J. Path.* 96:423–438 (1979).

Ghosh et al., "Lipid biochemistry: functions of glycerolipids and sphingolipids in cellular signaling," *Faseb. J.* 11:45–50 (1997).

Goetzl et al., "Lysophospholipid Growth Factors," in *Cytokine Reference* (Oppenheim, J, ed.), Academic Press, New York, 1407–1418 (2000).

Gohla et al., "The G-protein G13 but not G12 mediates signaling from lysophosphatidic acid receptor via epidermal growth factor receptor to Rho," *J. Biol. Chem.* 273:4653–4659 (1998).

Gonda et al., "The novel sphingosine 1-phosphate receptor AGR16 is coupled via pertussis toxin-sensitive and -insensitive G-proteins to multiple signaling pathways," *Biochem. J.* 337:67–75 (1999).

Guo et al., "Molecular cloning of a high-affinity receptor for the growth factor-like lipid mediator lysophosphatidic acid from *Xenopus* oocytes," *Proc. Natl. Acad. Sci. USA.* 93:14367–14372 (1996).

Hecht et al., "Ventricular zone gene-1 (vzg-1) encodes a lysophosphatidic acid receptor expressed in neurogenic regions of the developing cerebral cortex," *J. Cell. Biol.* 135:1071–1083 (1996).

Herrlich et al., "Ligand-independent activation of platelet-derived growth factor receptor is a necessary intermediate in lysophosphatidic, acid-stimulated mitogenic activity in L cells," *Proc. Natl. Acad. Sci. USA.* 95:8985–8990 (1998).

Hill et al., "The Rho family GTPases RhoA, Rac1, and CDC42Hs regulate transcriptional activation by SRF," *Cell* 81:1159–1170 (1995).

Hoffmann-Wellenhof et al., "Correlation of melanoma cell motility and invasion in vitro," *Melanoma. Res.* 5:311–319 (1995).

Hooks et al., "Characterization of a receptor subtype-selective lysophosphatidic acid mimetic," *Mol. Pharmacol.* 53:188–194 (1998).

Hunt and Goodson, In: *Current Surgical Diagnosis & Treatment* (Way, Appleton & Lange), pp. 86–98 (1988).

Im et al., "Molecular cloning and characterization of a lysophosphatidic acid receptor, Edg-7, expressed in prostate," *Mol. Pharmacol.* 57:753–759 (2000).

Imamura et al., "Serum requirement for in vitro invasion by tumor cells," *Jpn. J. Cancer Res.* 82:493–496 (1991).

Imamura et al., "Induction of in vitro tumor cell invasion of cellular monolayers by lysophosphatidic acid or phospholipase D," *Biochem. Biophys. Res. Com.* 193:497–503 (1993).

Imamura et al., "rho-Mediated protein tyrosine phosphorylation in lysophosphatidic-acid-induced tumor-cell invasion," *Int. J. Cancer* 65:627–632 (1996).

Jalink et al., "Lysophosphatidic acid, but not phosphatidic acid, is a potent Ca$^{2+}$-mobilizing stimulus for fibroblasts," *J. Biochem.* 265:12232–12239 (1990).

Jalink and Moolenaar, "Thrombin receptor activation causes rapid neural cell rounding and neurite retraction independent of classic second messengers," *J. Cell Biol.* 118:411–419 (1992).

Jalink et al., "Lysophosphatidic Acid is a Chemoattractant for Dictyostelium Discoideum Amoebae," *Proc. Natl. Acad. Sci. USA.* 90:1857–1861 (1993a).

Jalink et al., "Lysophosphatidic acid induces neuronal shape changes via a novel, receptor-mediated signaling pathway: similarity to thrombin action," *Cell Growth Differ.* 4:247–255 (1993b).

Jalink et al., "Growth factor-like effects of lysophasphatidic acid, a novel lipid mediator," *Biochimica. et. Biophysica. Acta.* 1198:185–196 (1994a).

Jalink et al., "Inhibition of lysophosphatidate- and thrombin-induced neurite retraction and neuronal cell rounding by ADP ribosylation of the small GTP-binding protein Rho," *J. Cell Biol.* 126:801–810 (1994b).

Jalink et al., "Lysophosphatidic acid-induced $Ca^{2+}$ mobilization in human A431 cells: structure-activity analysis," *Biochem. J.* 307:609–616 (1995).

Kartha et al., "Adenine nucleotides stimulate migration in wounded cultures of kidney epithelial cells," *J. Clin. Invest.*, 90:288–292 (1992).

Kawasawa et al., "Brain-specific expression of novel G-protein-coupled receptors, with homologies to Xenopus PSP24 and human GPR45," *Biochem. Biophys. Res. Commun.*, 276(3):952–956 (2000).

Kimura et al., "Effect of sphingosine and its N-methyl derivatives on oxidative burst, phagokinetic activity, and trans-endothelial migration of human neutrophils," *Biochem. Pharmacol.* 44:1585–1595 (1992).

Kimura et al., "Regulation of myosin phosphatase by Rho and Rho-associated kinase (Rho-kinase)," *Science* 273:245–248 (1996).

Kobayashi et al., "Existence of a Bioactive Lipid, Cyclic Phosphatidic Acid in Human Serum," *Life Sci.* 56:245–253 (1999).

Liliom et al., "N-palmitoyl-serine and N-palmitoyl-tyrosine phosphoric acids are selective competitive antagonists of the lysophosphatidic acid receptors," *Mol. Pharmacol.* 50:616–623 (1996).

Liliom et al., "Identification of a novel growth factor-like lipid, 1-O-cis-alk-1'-enyl-2-lyso-sn-glycero-3-phosphate (alkenyl-GP) that is present in commercial sphingolipid preparations," *J. Biol. Chem.* 273:13461–13468 (1998).

Lin et al., "Clathrin-mediated endocytosis of the beta-adrenergic receptor is regulated by phosphorylation/dephosphorylation of beta-arrestin1," *J. Biol. Chem.* 272:31051–31057 (1997).

Liotta et al., "Biochemical mechanisms of tumor invasion and metastasis," *Anticancer Drug Des.* 2:195–202 (1987).

Liu et al., "Synthesis, calcium mobilizing, and physico-chemical properties of D-chiroinositol 1,3,4,6-tetrakisphosphate, a novel and potent ligand at the D-myoinositol 1,4,5-trisphosphate receptor," *J. Med. Chem.* 42:1991–1998 (1999).

Luttrell et al., "Beta-arrestin-dependent formation of beta2 adrenergic receptor-Src protein kinase complexes," *Science* 283:655–661 (1999).

Lynch et al., "Structure/activity relationships in lysophosphatidic acid: the 2-hydroxyl moiety," *Mol. Pharmacol.* 52:75–81 (1997).

Machesky and Hall, "Rho: a connection between membrane signaling and cytoskeleton," *Trends Cell Biol.* 6:304–310 (1996).

Macrae et al., "Cloning, characterization, and chromosomal localization of rec1.3, a member of the G-protein-coupled receptor family highly expressed in brain," *Brain Res. Mol. Brain Res.* 42:245–254 (1996).

Mills et al., "A putative new growth factor in ascitic fluid from ovarian cancer patients: identification, characterization, and mechanism of action," *Cancer Res.* 48:1066–1071 (1988).

Mills et al., "Ascitic fluid from human ovarian cancer patients contains growth factors necessary for intraperitoneal growth of human ovarian adenocarcinoma cells," *J. Clin. Invest.* 86:851–855 (1990).

Miyata et al., "New wound-healing model using cultured corneal endothelial cells: Quantitative study of healing process," *Jpn. J. Opthalmol.*, 34:257–266 (1990).

Moolenaar, "G-protein-coupled receptors, phosphoinositide hydrolysis, and cell proliferation," *Cell Growth Differ.* 2:359–364 (1991).

Moolenaar, "A novel lipid mediator with diverse biological actions," *Trends in Cell Biology* 4:213–219 (1994).

Moolenar, "Lysophosphatidic acid, a multifunctional phospholipid messenger," *J. Biol. Chem.*, 270:12949–12952 (1996).

Moolenaar et al., "Lysophosphatidic acid: G-protein signalling and cellular responses," *Curr. Opin. Cell Biol.* 9:168–173 (1997).

Mukai et al., "Mechanism of tumor cell invasion studied by a culture model—modification of invasiveness by host mediators," *Hum. Cell* 6:194–198 (1993).

Muller et al., "Inhibitory action of transforming growth factor beta on endothelial cells," *Proc. Natl. Acad. Sci. USA* 84:5600–5604 (1987).

Munnik et al., "Identification of diacylglycerol pyrophosphate as a novel metabolic product of phosphatidic acid during G-protein activation in plants," *J. Biol. Chem.* 271:15708–15715 (1996).

Murakami-Murofushi et al., "Inhibition of cell proliferation by a unique lysophosphatidic acid, PHYLPA, isolated from Physarum polycephalum: signaling events of anti-proliferative action by PHYLPA," *Cell Struct. Funct.* 18:363–370 (1993).

Myher et al., "Molecular species of glycerophospholipids and sphingomyelins of human plasma: comparison to red blood cells," *Lipids* 24:408–418 (1989).

Ohkawara et al., In: *Biochemistry of Cutaneous Epithelial Differentiation,* Seiji et al., eds., University Park Press, Baltimore, 1977, pp. 274–278.

Parrill et al., "Identification of edg1 receptor residues that recognize sphingosine 1-phosphate," *J. Biol. Chem.* 275:39379–393784 (2000).

Postma et al., "Sphingosine-1-phosphate rapidly induces Rho-dependent neurite retraction: action through a specific cell surface receptor," *Embo. J.* 15:2388–2392 (1996).

Ridley, "Rho: theme and variations," *Curr. Biol.* 6:1256–1264 (1996).

Ridley and Hall, "The small GTP-binding protein rho regulates the assembly of focal adhesions and actin stress fibers in response to growth factors," *Cell* 70:389–399 (1992).

Sato et al., "Autocrine activities of basic fibroblast growth factor: regulation of endothelial cell movement, plasminogen activator synthesis, and DNA synthesis," *J. Cell Biol.*, 107:1199–1205 (1988).

Schumacher et al., "Platelet aggregation evoked in vitro and in vivo by phosphatidic acids and lysodervatives: identity with substances in aged serum (DAS)," *Thrombos. Haemostas.* 42:631–640 (1979).

Simon et al., "Human platelet aggregation induced by 1-alkyl-lysophosphatidic acid and its analogs: a new group of phospholipid mediators?," *Biochem. Biophys. Res. Commun.* 108:1743–1750(1982).

Spiegel and Milstien, "Functions of a new family of sphingosine-1-phosphate receptors," *Biochim. et. Biophys. Acta.* 1484:107–116 (2000).

Sugiura et al., "Biochemical characterization of the interaction of lipid phosphoric acids with human platelets: Comparison with platelet activating factor," *Arch. Biochem. Biophys.* 311:358–368 (1994).

Sun et al., "Synthesis of Chiral 1-(2'-Amino-2'-carboxyethyl)-1,4-dihydro-6,7-quinoxaline-2,3-diones: α-amino-3-hydroxy-5-methyl-4-isoxazolepropionate Receptor Agonists and Antagonists," *J. Med. Chem.* 39:4430–4438 (1996).

Tigyi et al., "A serum factor that activates the phosphatidylinositol phosphate signaling system in *Xenopus* oocytes," *Proc. Natl. Acad. Sci. USA* 87:1521–1525 (1990).

Tigyi et al., "A factor that activates oscillatory chloride currents in *Xenopus* oocytes copurifies with a subfraction of serum albumin," *J. Biol. Chem.* 266:20602–20609 (1991).

Tigyi and Miledi, "Lysophosphatidates bound to serum albumin activate membrane currents in *Xenopus* oocytes and neurite retraction in PC12 pheochromocytoma cells," *J. Biol. Chem.* 267:21360–21367 (1992).

Tigyi et al., "Lysophosphatidic acid possesses dual action in cell proliferation," *Proc. Natl. Acad. Sci. USA.* 91:1908–1912 (1994).

Tigyi et al., "Lysophosphatidic acid-induced neurite retraction in PC12 cells: control by phosphoinositide-$Ca^{2+}$ signaling and Rho," *J. Neurochem.* 66:537–548 (1996).

Tigyi et al., "Pharmacological characterization of phospholipid growth factor receptors," *Ann. NY Acad. Sci.* 905:34–53 (2000).

Tokumura et al., "Effects of synthetic and natural lysophosphatidic acid on the arterial blood pressure of different animal species," *Lipids* 13:572–574 (1978).

Tokumura et al., "Stimulatory effect of lysophosphatidic acids on uterine smooth muscles of non-pregnant rats," *Arch. Int. Pharmacodyn. Ther.* 245:74–83 (1980).

Tokumura et al., "Lysophosphatidic acid-induced aggregation of human and feline platelets: structure-activity relationship," *Biochem. Biophys. Res. Commun.* 99:391–398 (1981).

Tokumura et al., "Involvement of lysophospholipase D in the production of lysophosphatidic acid in rat plasma," *Biochim. et. Biophys. Acta.* 875:31–38 (1986).

Tokumura et al., "Lysophosphatidic acids induce proliferation of cultured vascular smooth muscle cells from rat aorta," *Am. J. Physiol.* 267:204–210 (1994).

Tokumura, "A family of phospholipid autacoids: occurrence, metabolism, and bioactions," *Prog. Lipid Res.* 34:151–184 (1995).

Umansky et al., "Prevention of rat neonatal cardiomyocyte apoptosis induced by stimulated in vitro ischemia and reperfusion," *Cell Death Diff.* 4:608–616 (1997).

van Brocklyn et al., "Dual actions of sphingosine-1-phosphate: extracellular through the Gi-coupled receptor Edg-1 and intracellular to regulate proliferation and survival," *J. Cell. Biol.* 142:229–240 (1998).

van Brocklyn et al., "Sphingosine-1-phosphate is a ligand for the G protein-coupled receptor EDG-6," *Blood* 95:2624–2629 (2000).

van Corven et al., "Lysophosphatidic-induced cell proliferation: identification and dissection of signaling pathways mediated by G proteins," *Cell* 59:45–54 (1989).

van Corven et al., "Mitogenic action of lysophosphatidic acid and phosphatidic acid on fibroblasts: Dependence on acyl-chain length and inhibition by suramin," Biochem. J. 281:163–169 (1992).

van der Bend et al., "The biologically active phospholipid, lysophosphatidic acid, induces phosphatidylcholine breakdown in fibroblasts via activation of phospholipase D: Comparison with the response to endothelin," *Biochem. J.* 285:235–240 (1992a).

van der Bend et al., "Identification of a putative membrane receptor for the bioactive phospholipid, lysophosphatidic acid," *EMBO.* 11:2495–2501 (1992b).

Verrier et al., "Wounding a fibroblast monolayer results in the rapid induction of the c-fos proto-oncogene," *EMBO J.*, 5:913–917 (1986).

Wissing and Behrbohm, "Diacylglycerol pyrophosphate, a novel phospholipid compound," *FEBS Lett.* 315: 95–99 (1993).

Xu et al., "Characterization of an ovarian cancer activating factor in ascites from ovarian cancer patients," *Clin. Cancer Res.* 1:1223–1232 (1995a).

Xu et al., "Effect of lysophospholipids on signaling in the human Jurkat T cell line," *J. Cell. Physiol.*, 163:441–450 (1995b).

Yatomi et al., "Sphingosine-1-phosphate: a platelet-activating sphingolipid released from agonist-stimulated human platelets," *Blood* 86:193–202 (1995).

Zhou et al., "Phosphatidic acid and lysophosphatidic acid induce haptotactic migration of human monocytes," *J. Biol. Chem.* 270:25549–25556 (1995).

Zsiros et al., "Naturally occurring inhibitors of lysophosphatidic acid," *Abstr. 6th. International Congress on Platelet Activating Factor and Related Lipid Mediators,* p.128 (1998).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed is:

1. A compound according to formula (I)

$$CQ^1-\underset{\underset{X^1}{|}}{\overset{\overset{X^3}{|}}{CH}}-\underset{\underset{X^2}{|}}{CQ^2} \quad (I)$$

wherein $X^1$ is $(HO)_2PO\text{-}Z^1\text{-}$;

$X^2$ and $X^3$ are both $R^1R^2N$ -A- with each being the same or different $Z^1$ is $-O(CH_2)_m-$ with m being an integer from 1 to 50, or $-O-$;

$Q^1$ and $Q^2$ are independently $H_2$, $=NR^4$, $=O$, or a combination of H and $-NR^5R^6$;

$R^1$ at $X^2$ is a straight or branched-chain C1 to C30 alkyl, a straight or branched-chain C2 to C30 alkenyl, or an acyl including a C1 to C30 alkyl or an aromatic or heteroaromatic ring $R^1$ at $X^3$ is hydrogen, a straight or branched-chain C1 to C30 alkyl, a straight or branched-chain C2 to C30 alkenyl, or an acyl including a C1 to C30 alkyl or an aromatic or heteroaromatic ring; and $R^2$, $R^4$, $R^5$, and $R^6$ are independently hydrogen, a straight or branched-chain C1 to C30 alkyl, a straight or branched-chain C2 to C30 alkenyl, an aromatic or heteroaromatic ring with or without mono-, di-, or tri-substitutions of the ring, an acyl including a C1 to C30 alkyl or aromatic or heteroaromatic ring, an arylalkyl including straight or branched-chain C1 to C30 alkyl, or an aryloxyalkyl including straight or branched-chain C1 to C30 alkyl;

wherein when $R^2$ at $X^2$ is H and $O^2$ is $=O$, $R^1$ is a straight chain C10 to C18 alkyl group.

2. The compound according to claim 1, wherein the from group (ii) and wherein $Q^1$ is $H_2$;

$Q^2$ is $=O$;

$Z^1$ is O; and $R^2$ at both $X^2$ and $X^3$ is H.

3. The compound according to claim 2, wherein $X^3$ is $-NH_2$ and $R^1$ at $X^2$ is a straight chain C14 to C18 alkyl.

4. The compound according to claim 3, wherein $R^1$ at $X^2$ is a C14alkyl.

5. The compound according to claim 3, wherein $R^1$ is at $X^2$ a C18 alkyl.

6. The compound according to claim 2, wherein $R^1$ at $X^3$ is an acetyl group and $R^1$ at $X^2$ is a C14 alkyl.

7. A pharmaceutical composition comprising:

a pharmaceutically-acceptable carrier and a compound according to claim 1.

* * * * *